(12) United States Patent
Druzgala et al.

(10) Patent No.: US 7,932,405 B2
(45) Date of Patent: *Apr. 26, 2011

(54) HALOGENATED ESTER DERIVATIVES OF COUMARINS FOR THE TREATMENT OF COAGULATION DISORDERS

(75) Inventors: Pascal Druzgala, Santa Rosa, CA (US); Cyrus Becker, Fremont, CA (US)

(73) Assignee: Aryx Therapeutics, Inc., Freemont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/268,109

(22) Filed: Nov. 10, 2008

(65) Prior Publication Data

US 2009/0082430 A1 Mar. 26, 2009

Related U.S. Application Data

(63) Continuation of application No. 11/778,482, filed on Jul. 16, 2007, now Pat. No. 7,666,902.

(51) Int. Cl.
*C07D 311/56* (2006.01)
*A61K 31/352* (2006.01)

(52) U.S. Cl. ........................ 549/402; 514/457
(58) Field of Classification Search .................. 514/457; 549/400, 402
See application file for complete search history.

(56) References Cited

U.S. PATENT DOCUMENTS

| | | | |
|---|---|---|---|
| 5,510,375 A | 4/1996 | Domagala et al. | |
| 5,686,486 A | 11/1997 | Tomich et al. | |
| 6,864,279 B2 | 3/2005 | Druzgala et al. | |
| 7,253,208 B2 * | 8/2007 | Druzgala et al. | 514/457 |
| 7,285,671 B2 * | 10/2007 | Druzgala et al. | 549/286 |
| 2004/0058985 A1 | 3/2004 | Carter | |
| 2004/0220258 A1 | 11/2004 | Druzgala et al. | |

FOREIGN PATENT DOCUMENTS

| | | |
|---|---|---|
| WO | 02/085882 A1 | 10/2002 |
| WO | 2004/058985 | 3/2004 |

OTHER PUBLICATIONS

Wakefield, Basil "Fluorinated Pharmaceuticals" Innovations in Pharmaceutical Technology 2003, 74, 76-78, Online "http://web.archive.org/web/20030905122408/http://www.iptonline.com/articles/public/IPTFOUR74NP.pdf." (accessed via Wayback machine Nov. 20, 2009 showing web availability as of Sep. 2003).*
Patani et. al. "Bioisosterism: A Rational Approach in Drug Design" Chemical Reviews 1996, 96, 3147-3176.*
Wikianswers "http://wiki.answers.com/Q/What_is_a_substituted_hydrocarbon" online accessed Sep. 1, 2010.*
Jones et al., "Solvolysis Mechanisms. Sn1-Like Behavior of Methyl Chloromethyl Ether. Sensitivity to Solvent Ionizing Power and α-Deuterium Isotope Effect, " Journal of the American Chemical Society, 89, 4863-4867 (1967).
DeRuiter, "Resonance and Induction Tutorial," Principles of Drug Action 1, Spring 2005, Resonanec and Induction, Online "http://www.auburn.edu/~deruija/pda1_resonance.pdf" accessed Jun. 22, 2009.
Tou et al., "Kinetic Study of the Stabilities of Chloromethyl Methyl Ether and Bis(Chloromethyl) Ether in Humid Air," Analytical Chemistry, 46, 1866-1869 (1974).
Theopold et al., "Coagulation in arthropods: defence, wound closure and healing," Trends in Immunology, 25(6), 289 (2004).
McMaster Hematology Program online "http://fhs.mcmaster.ca/hemares/designduration.htm" accessed Oct. 17, 2008.
Oldenburg, J. et al., Chapter 3 "The Vitamin K Cycle," Vitamins and Hormones, 78:35-62 (2008).
Mann et al., "Biochemistry and Physiology of Blood Coagulation," Thrombosis and Haemostasis, 82(2):165-174 (1999).
"Coumadin Tablets," Online "http://www.fda.gov/cder/foi/label/2007/009218s105lblv2.pdf," accessed Oct. 20, 2008.
Nurden et al., "Inherited disorders of platelets: an update," Current Opinion in Hematology, 13:157-162 (2006).
Dahl et al., "The Reactivity of Affinity Labels: A Kinetic Study of the Reaction of Alkyl Halides with Thiolate Anions—a Model Reaction for Protein Aklylation," Bioorganic Chemistry, 10:329-341 (1981).
Castro et al., "Biodehalogenation. Reductive Reactivities of Microbial and Mammalian Cytochromes P-450 Compared with Heme and Whole-Cell Models," Journal of Agricultural & Food Chemistry, 36, 915-919 (1988).
Wheeler et al., "Conjugation of Haloalkanes by Bacterial and Mammalian Glutathione Transferases: Mono- and Vicinal Dihaloethanes," Chemical Research in Toxicology, 14, 1107-1117 (2001).
Goodstadt et al., "Vitamin K epoxide reductase: homology, active site and catalytic mechanism," Trends in Biochemical Sciences, 29(6):289-292 (2004).
Johnson, A.W., Invitation to Organic Chemistry, Jones and Bartlett: Mississauga, Canada, p. 24 (1999).
Horton et al., "Reactions with Reactive Alkyl Halides," Methods in Enzymology, 11, 556-565 (1967).

* cited by examiner

*Primary Examiner* — Rita J Desai
*Assistant Examiner* — David K O'Dell
(74) *Attorney, Agent, or Firm* — McDonnell Boehnen Hulbert & Berghoff LLP

(57) ABSTRACT

The subject invention provides anticoagulant compounds of formula I:

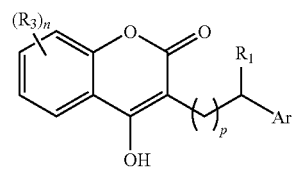

and pharmaceutically acceptable salts thereof, wherein $R_1$, $R_3$, n and Ar are as defined herein. The compounds of the subject invention can be used to treat at-risk populations thereby bringing relief of symptoms, improving the quality of life, preventing acute and long-term complications, reducing mortality and treating accompanying disorders. The invention further comprises pharmaceutical compositions comprising the compounds and salts of the invention, as well as methods of using the compounds, salts, and compositions of the invention.

5 Claims, 8 Drawing Sheets

Figure 1: *VKER inhibitory activity of 3-(4-Hydroxy-2-oxo-2H-chromen-3-yl)-3-(4-trifluoromethoxy-phenyl)-propionic acid*
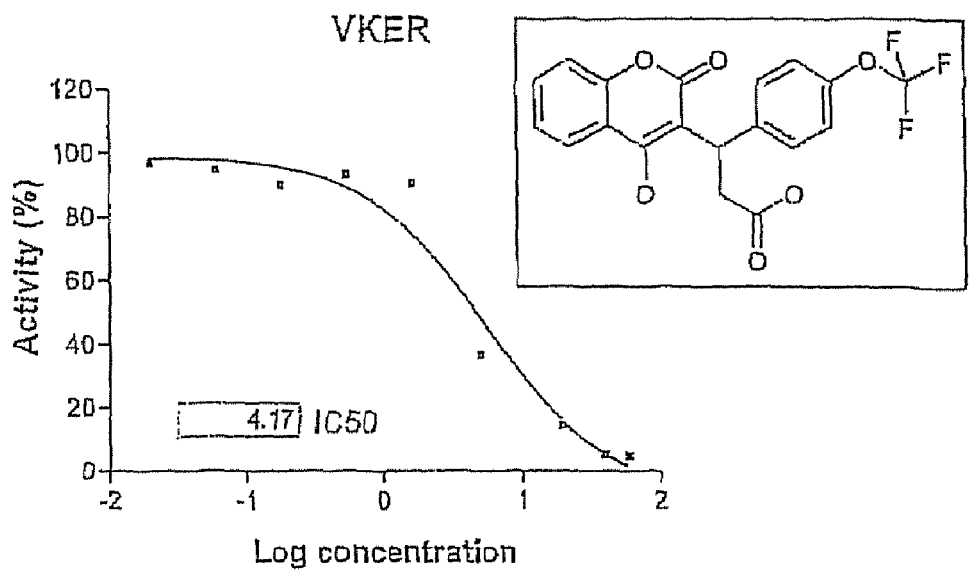
Figure 2: *VKER inhibitory activity of 4-(4-Hydroxy-2-oxo-2H-chromen-3-ylmethyl)-benzoic acid 2,2,3,3,3-pentafluoro-propyl ester*
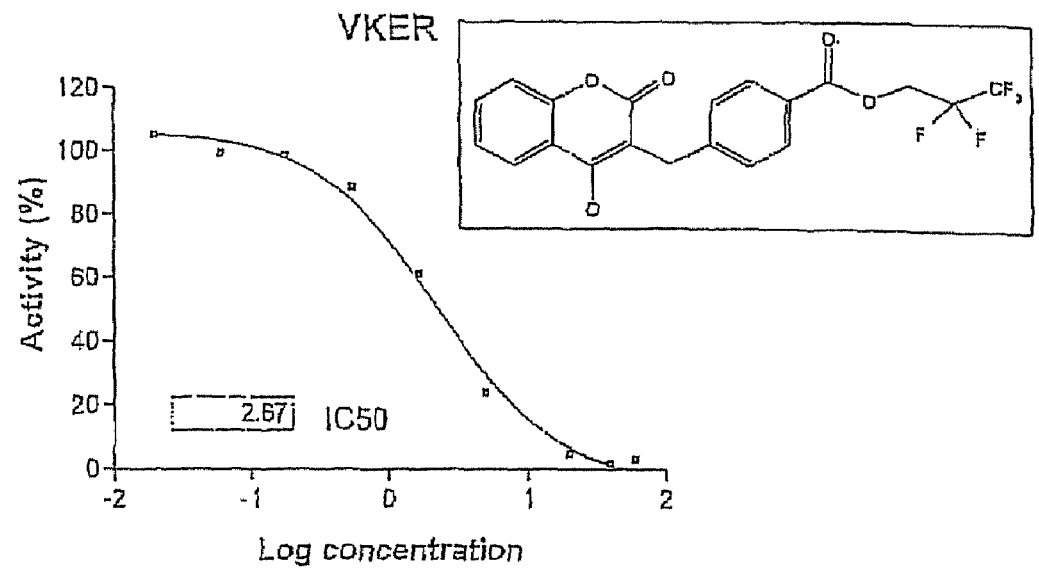

Figure 3: *VKER inhibitory activity of 4-(4-Hydroxy-2-oxo-2H-chromen-3-ylmethyl)-benzoic acid 3,3,3-trifluoro-propyl ester*
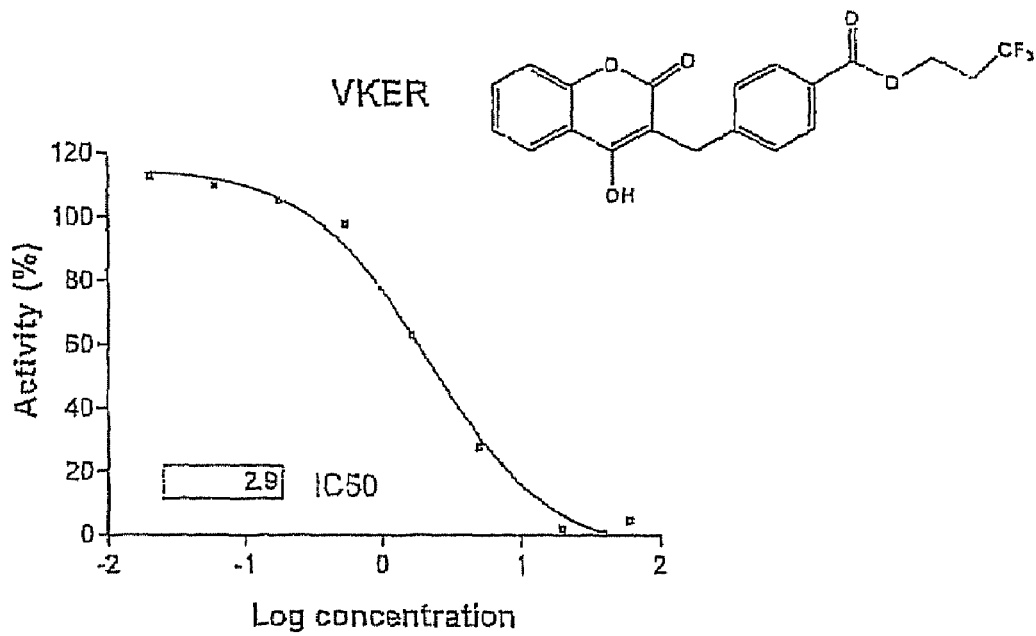
Figure 4: *VKER inhibitory activity of 4-(4-Hydroxy-2-oxo-2H-chromen-3-ylmethyl)-benzoic acid 2,2,3,3,3-pentafluoro-1-methyl-propyl ester*
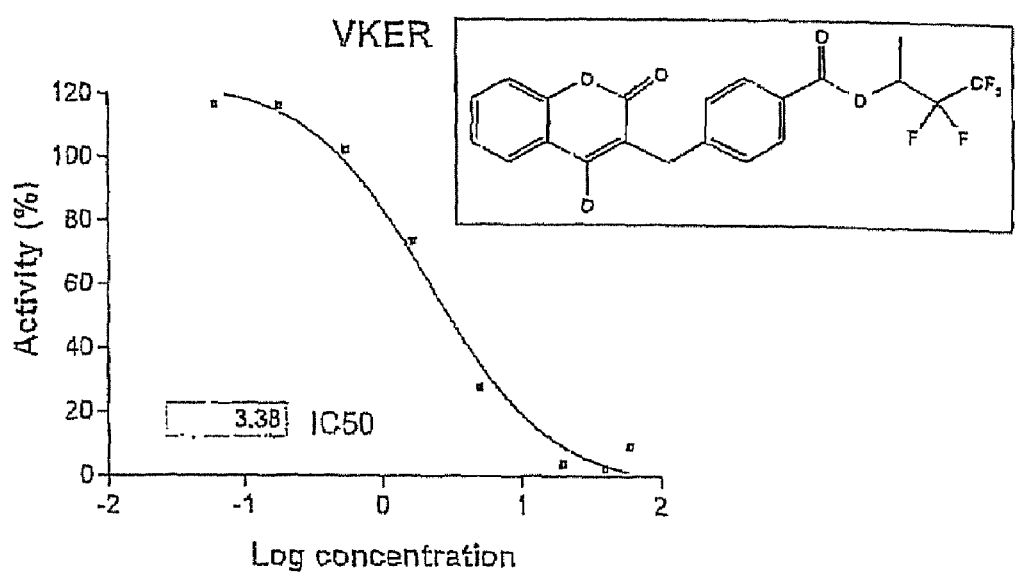

Figure 5: VKER inhibitory activity of 4-(4-Hydroxy-2-oxo-2H-chromen-3-ylmethyl)-benzoic acid 4-fluoro-benzyl ester
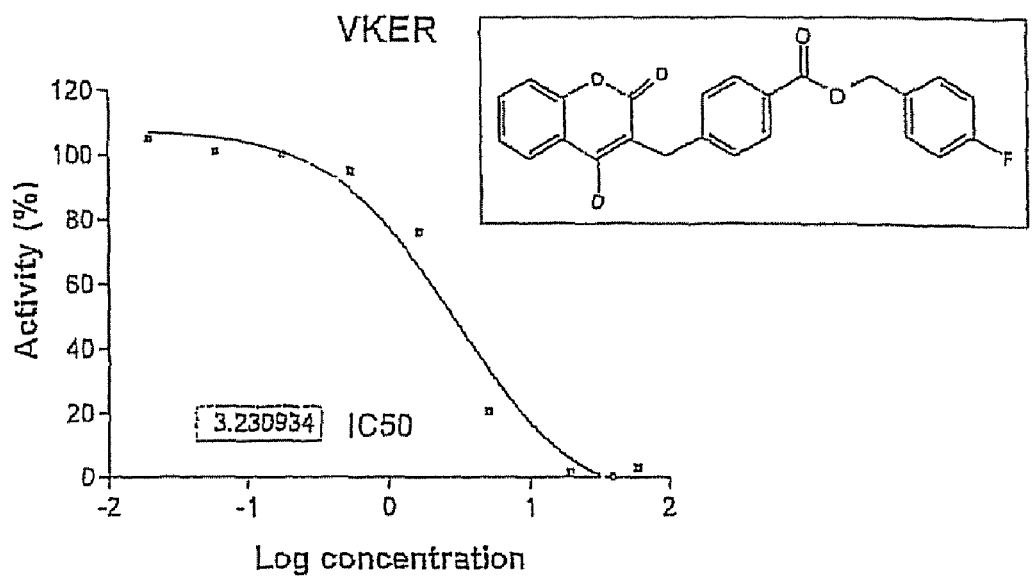
Figure 6: VKER inhibitory activity of 4-(4-Hydroxy-2-oxo-2H-chromen-3-ylmethyl)-benzoic acid 2-(4-fluoro-phenoxy)-ethyl ester
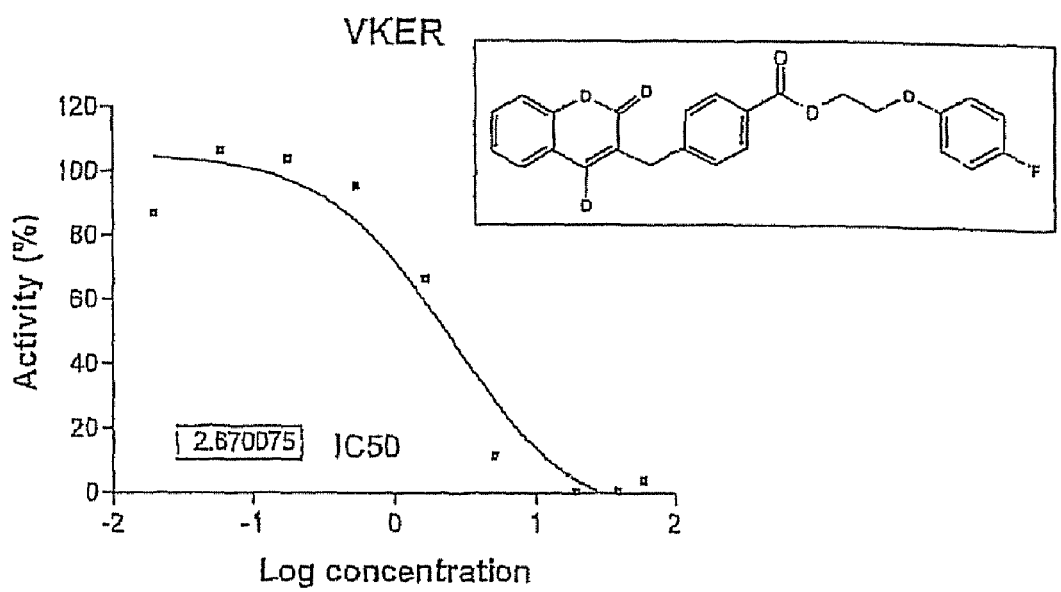

Figure 7: *VKER inhibitory activity of 4-(4-Hydroxy-2-oxo-2H-chromen-3-ylmethyl)-benzoic acid 2,2,2-trifluoro-1-methyl-ethyl ester*
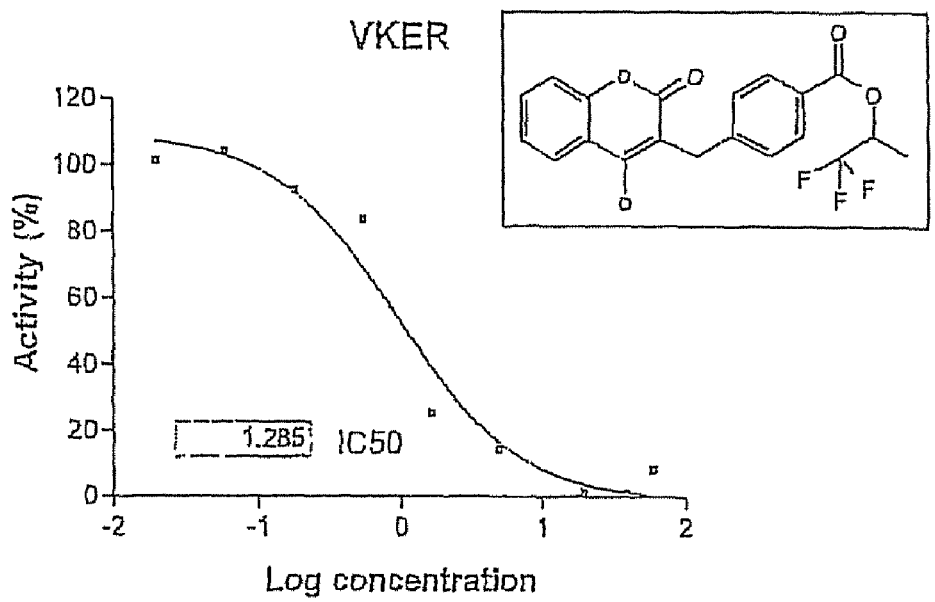
Figure 8: *VKER inhibitory activity of 4-(4-Hydroxy-2-oxo-2H-chromen-3-ylmethyl)-benzoic acid 2,2,2-trifluoro-1-trifluoromethyl-ethyl ester*
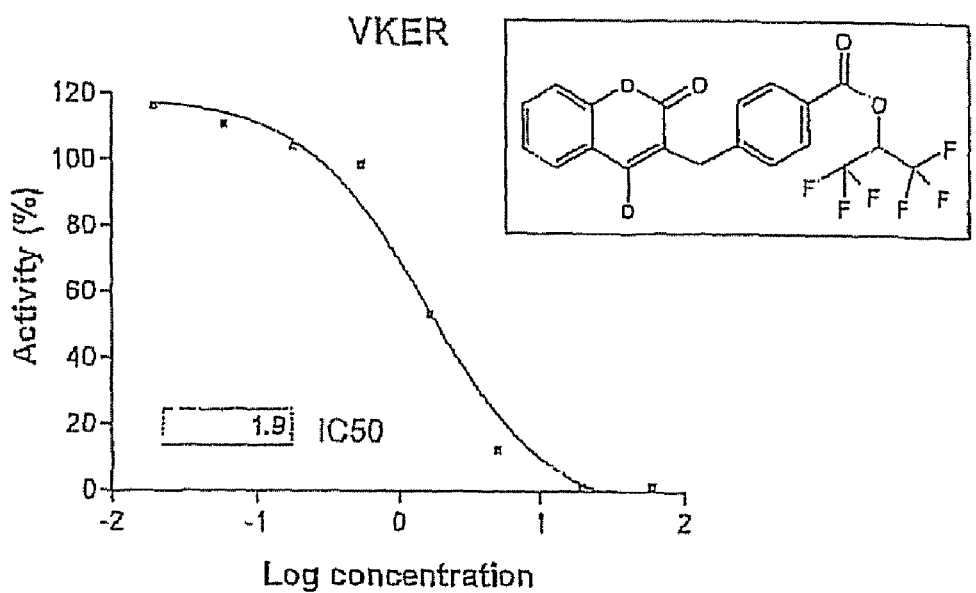

Figure 9: *VKER inhibitory activity of 4-(4-Hydroxy-2-oxo-2H-chromen-3-ylmethyl)-benzoic acid 2,2,2-trifluoro-1-methyl-1-trifluoromethyl-ethyl ester*
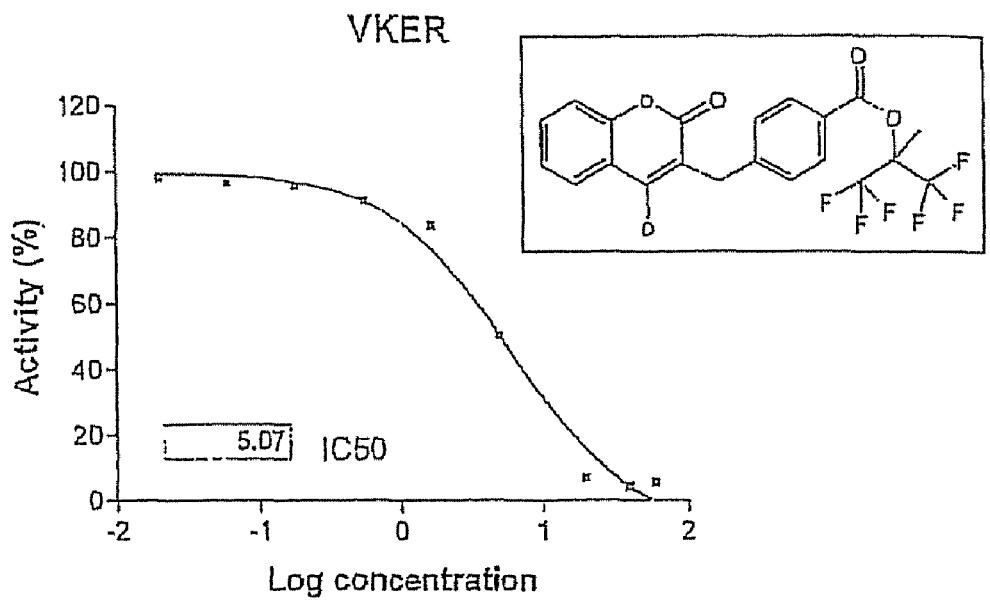
Figure 10 *VKER inhibitory activity of warfarin*
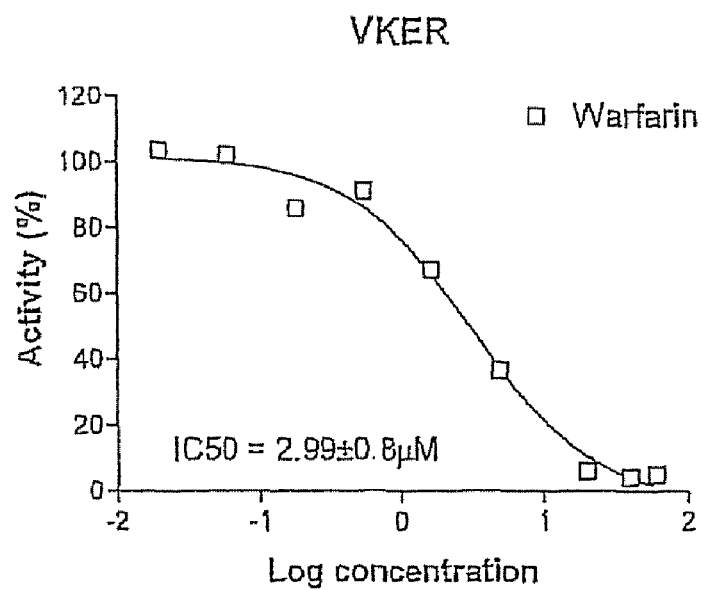

Figure 11 VKER inhibitory activity of 4-[(4-hydroxy-2-oxo-2H-chromen-3-yl)methyl]benzoic acid
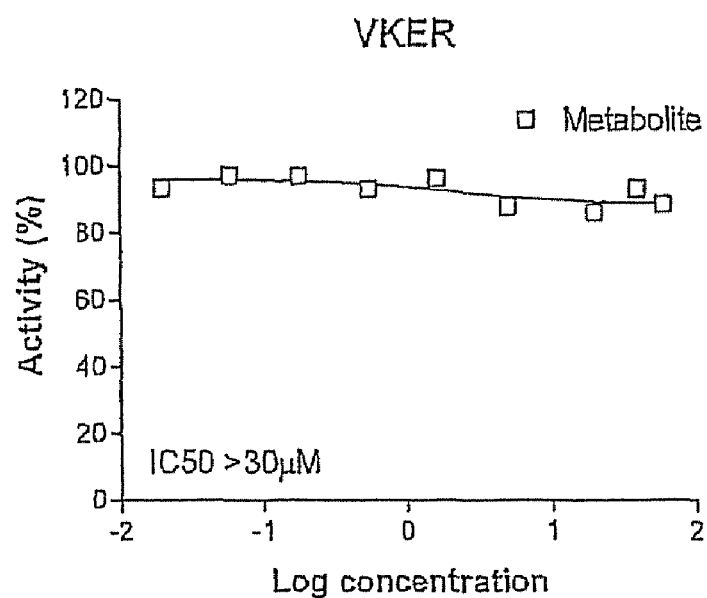
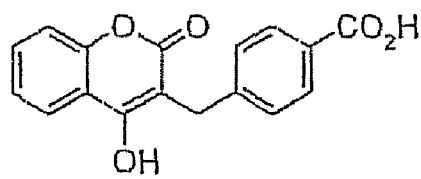

Figure 12 *Effect of fluorination on the metabolism by cytochrome P450 and esterase in pooled human microsomes*
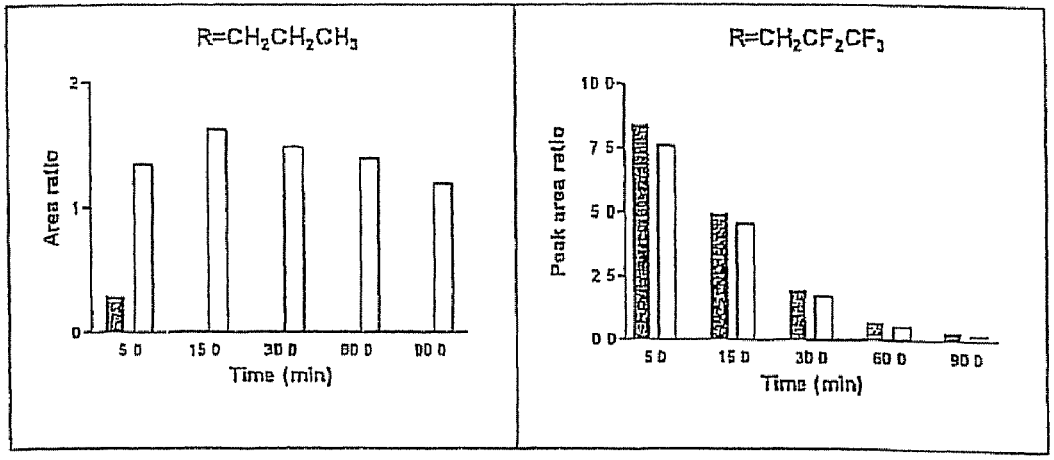
Figure 13 *Effect of fluorination on the metabolism by cytochrome P450 and esterase in pooled human microsomes*
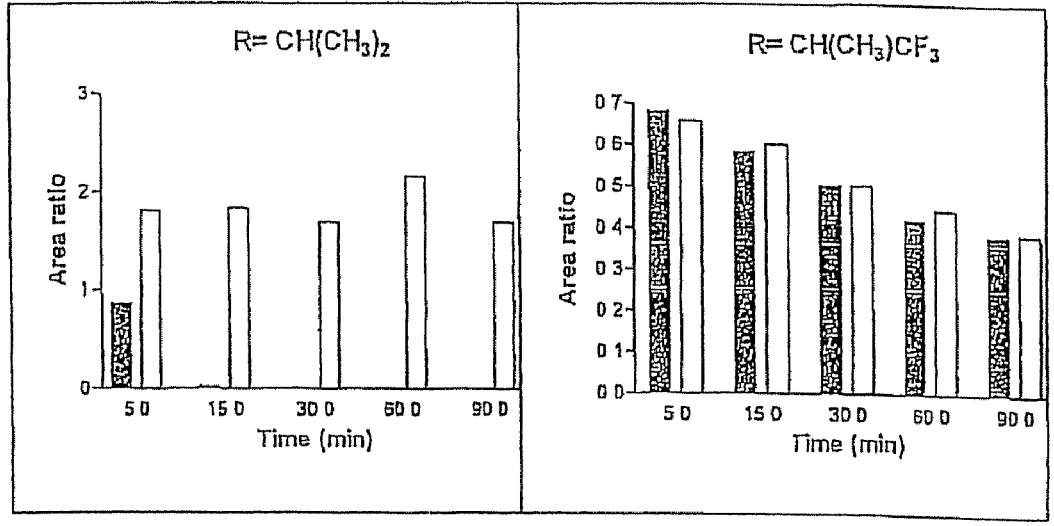

Figure 14 _Control demonstrating compound metabolism by esterase_
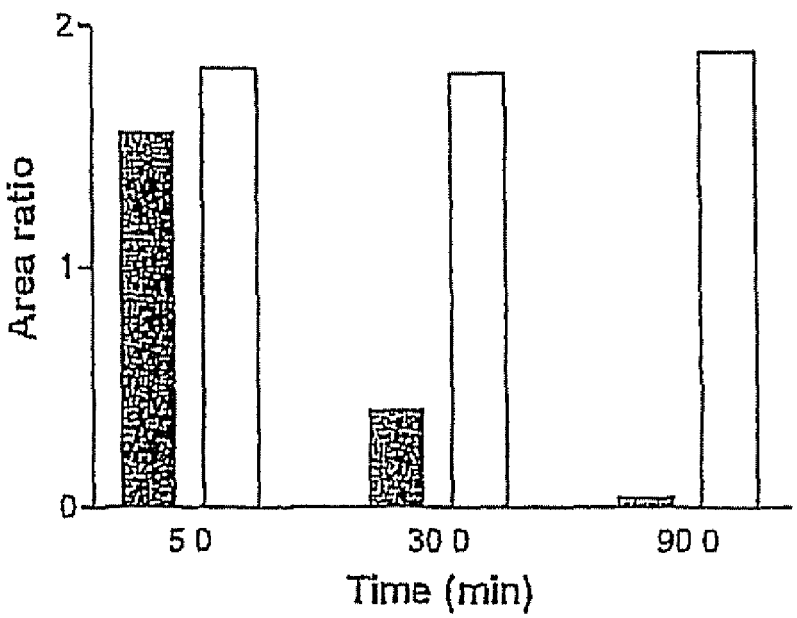

HALOGENATED ESTER DERIVATIVES OF COUMARINS FOR THE TREATMENT OF COAGULATION DISORDERS

CROSS REFERENCE TO RELATED APPLICATIONS

This application is a continuation of U.S. application Ser. No. 11/101,714 filed Apr. 8, 2005, which claims priority from U.S. Provisional Application No. 60/561,121 filed Apr. 8, 2004 and is a continuation of U.S. application Ser. No. 10/822,129 filed Apr. 8, 2004, which are incorporated herein by reference.

BACKGROUND OF INVENTION

Warfarin (coumarin) is an anticoagulant that acts by inhibiting vitamin K-dependent coagulation factors. Warfarin based compounds are, typically, derivatives of 4-hydroxycoumarin, such as 3-α-acetonylbenzyl)-4-hydroxycoumarin (COUMADIN). COUMADIN and other coumarin anticoagulants inhibit the synthesis of vitamin K dependent clotting factors, which include Factors II, VII, IX and X. Anticoagulant proteins C and S are also inhibited by warfarin anticoagulants. Warfarin is believed to interfere with clotting factor synthesis by inhibiting vitamin K epoxide reductase, thereby inhibiting vitamin K regeneration.

An anticoagulation effect is generally seen about 24 hours after administration of a single dose of warfarin and is effective for 2 to 5 days. While anticoagulants have no direct effect on an established thrombus and do not reverse ischemic tissue damage, anticoagulant treatment is intended to prevent the extension of formed clots and/or to prevent secondary thromboembolic complications. These complications may result in serious and possibly fatal sequelae.

The FDA has approved warfarin for the following indications: 1) the treatment or prophylaxis of venous thrombosis and pulmonary embolism, 2) thromboembolic complications associated with atrial fibrillation and/or cardiac valve replacement, and 3) reducing the risk of death, recurring myocardial infarction, and stroke or systemic embolism after myocardial infarction.

A number of adverse effects are associated with the administration of warfarin. These include fatal or nonfatal hemorrhage from any tissue or organ and hemorrhagic complications such as paralysis. Other adverse effects include paresthesia including feeling cold and chills; headache; chest, abdomen, joint, muscle or other pain; dizziness; shortness of breath; difficult breathing or swallowing; unexplained swelling, weakness, hypotension, or unexplained shock. Other adverse reactions reported include hypersensitivity/allergic reactions, systemic cholesterol microembolization, purple toes syndrome, hepatitis, cholestatic hepatic injury, jaundice, elevated liver enzymes, vasculitis, edema, fever, rash, dermatitis, including bullous eruptions, urticaria, abdominal pain including cramping, flatulence/bloating, fatigue, lethargy, malaise, asthenia, nausea, vomiting, diarrhea, pain, headache, dizziness, taste perversion, pruritus, alopecia and cold intolerance.

Drug toxicity is an important consideration in the treatment of humans and animals. Toxic side effects resulting from the administration of drugs include a variety of conditions that range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is the result of metabolic activity upon the drug and the subsequent excretion of the drug from the body. Metabolic activity can take place within the vascular supply and/or within cellular compartments or organs. The liver is a principal site of drug metabolism. The metabolic process can be broken down into primary and secondary metabolism, also called phase-1 and phase-2 metabolism. In phase-1 metabolism, the drug is chemically altered by oxidation, reduction, hydrolysis, or any combination of the aforementioned processes and usually yields a more polar product than the parent drug. In Phase-2 metabolism the products of the phase-1 reaction are combined with endogenous substrates, e.g., glucuronic acid, to yield an addition or conjugation product that is even more hydrophilic than the product of phase-1 and which is readily eliminated in the bile or in the urine. In some cases, a drug can undergo only phase-2 (conjugation) metabolism, in other cases a drug can be eliminated unchanged. The first step in such synthetic reactions is often an oxidative conjugation performed by the cytochrome P450 (CYP450) system. Metabolites formed in phase-2 reactions are typically the product of a conjugation reaction performed by a transferase enzyme. These reactions include glucuronidation, amino acid conjugation, acetylation, sulfoconjugation, and methylation.

Mammalian cytochrome P450 enzymes (CYP450), including human CYP450, are membrane-bound heme-containing proteins that were originally discovered in rat liver microsomes. In order to function, CYP450 enzymes need a source of electrons. There are two different kinds of electron transfer chains for CYP450s. These depend on the location of the enzyme in the cell. Some P450s are found in the mitochondrial inner membrane and some are found in the endoplasmic reticulum (ER). The protein that donates electrons to CYP450s in the ER is called NADPH cytochrome P450 reductase. Ferredoxin is the immediate donor of electrons to the CYP450s in mitochondria (CYP11A1, CYP11B1, CYP11B2, CYP24, CYP27A1, CYP27B1, CYP27C1). NADPH is the source of electrons that flow from ferredoxin reductase to ferredoxin and then to CYP450. A few P450s also can accept electrons from cytochrome b5.

Polymorphisms (differences in DNA sequence found at 1% or higher in a population) can lead to differences in drug metabolism, so they are important features of CYP450 genes in humans. CYP2C19 has a polymorphism that changes the enzyme's ability to metabolize mephenyloin (a marker drug). In Caucasians, the polymorphism for the poor metabolizer phenotype is only seen in 3% of the population. However, it is seen in 20% of the Asian population. Because of this difference, it is important to be aware of a person's race when drugs are given that are metabolized differently by different populations. Some drugs that have a narrow range of effective dose before they become toxic might be overdosed in a poor metabolizer.

CYP2D6 is perhaps the best studied P450 with a drug metabolism polymorphism. This enzyme is responsible for more than 70 different drug oxidations. Since there may be no other way to clear these drugs from the system, poor metabolizers may be at severe risk for adverse drug reactions. CYP2D6 Substrates include antiarrhythmics (Flecainide, Mexiletine, Propafenone), antidepressants (Amitriptyline, Paroxetine, Venlafaxine, Fluoxetine, Trazadone), antipsychotics (Clorpromazine, Haloperidol, Thoridazine), beta-blockers (Labetalol, Timolol, Propanolol, Pindolol, Metoprolol), analgesics (Codeine, Fentanyl, Meperidine, Oxycodone, Propoxyphene), and many other drugs. CYP2E1 is induced in alcoholics. There is a polymorphism associated with this gene that is more common in Chinese people.

The CYP3A subfamily is one of the most important drug metabolizing families in humans. CYP3A4 is "the most abundantly expressed CYP450 in human liver". (Arch. Biochem. Biophys. 369, 11-23 1999) CYP3A4 is known to metabolize more than 120 different drugs, e.g., acetaminophen, codeine, cyclosporin A, diazepam, erythromycin, lidocaine, lovastatin, taxol, cisapride, terfenadine, and warfarin, to name a few.

The number of adverse drug reactions (ADRs) in the United States has risen dramatically in recent years and now represents a critical national health problem. The World Health Organization (WHO) defines an ADR as "a response to a drug that is noxious and unintended and occurs at doses normally used in man for the prophylaxis, diagnosis or therapy of disease, or for modification of physiological function". To highlight the importance of error in the genesis of ADRs and the fact that most (30-80%) ADRs are preventable, a more recent definition of an ADR is "an appreciably harmful or unpleasant reaction, resulting from an intervention related to the use of a medicinal product, which predicts hazard from future administration and warrants prevention or specific treatment, or alteration of the dosage regimen, or withdrawal of the product."

Because ADRs are a major source of morbidity and mortality in our health care system, reducing the incidence of ADRs has become a national priority (FDA, Center for Drug Evaluation and Research). According to formal estimates, greater than 2.5 million ADRs occur each year in hospitals, ambulatory settings and nursing homes, resulting in over 106,000 deaths, and costing the US economy $136B annually in drug-related morbidity and mortality. This expense is greater than the annual cost of cardiovascular disease and diabetes in the United States. In addition, the estimated mortality rate associated with ADRs make them the fourth leading cause of death in this country.

Many ADRs arise from the fact that most drugs developed by the pharmaceutical industry significantly interact with components of the CYP system, either by relying on them for their metabolism and/or by inhibiting or inducing various CYP fractions. In other words, because so many important drug classes (e.g., antihypertensives, antihistamines, antidepressants, immunosuppressants, statins) interact with the CYP system, it can act as a "bottleneck" for the safe metabolism and elimination of these agents and lead to toxic effects. With regard to drug metabolism, two fractions of the CYP system merit special mention: CYP3A4 and CYP2D6. Approximately one half of all known drugs interact with CYP3A4. Likewise, CYP2D6, an enzyme fraction whose activity is highly dependent on genetics (genetic polymorphisms), metabolizes one third of drugs in clinical use. Both of these enzymes are involved in the metabolism of warfarin-like compounds.

The vast majority (70-90%) of ADRs occur as extensions of their expected pharmacological effects (exaggerated pharmacology). This is particularly relevant to the use of warfarin since the extension of the warfarin pharmacological effect is bleeding. Although many different factors can contribute to the development of ADRs, altered drug metabolism leading to elevated drug levels, either due to drug interactions at the enzymatic level, genetic alterations in enzyme activity, and/or organ dysfunction (liver, kidney), play a particularly important role in the genesis of ADRs.

Drug therapy using warfarin is particularly difficult because the metabolism of warfarin is complex and subject to interactions with a host of other drugs, including drugs that are commonly prescribed in patients suffering from atrial fibrillation, such as amiodarone for example. Warfarin is a mixture of enantiomers having different intrinsic activities at the vitamin K epoxide reductase (VKER) enzyme. These enantiomers have different metabolic pathways using different CYP450 isozymes. The CYP450 metabolic system is highly inducible or repressible by a host of external factors such as diet and other medications. Also, the CYP450 system is subject to many genetic variations and has a low capacity and is easily saturable. For these reasons the metabolism of warfarin is subject to unpredictable variations and each enantiomer has a different metabolic fate and different potencies at the VKER enzyme.

In addition, warfarin activity at the VKER enzyme results in inhibition of coagulation factors II, VII, IX, and X, which have different half-lives of their own, ranging from hours (factor VII) to days (factor X). Because of this complex situation, the pharmacological effect (increased coagulation time) of warfarin becomes apparent only 5 to 10 days after a dose. It is therefore easy to understand why warfarin therapy is extremely difficult to predict and why patients are at high risk of bleeding complications including death. In the current state of warfarin therapy, patients on warfarin must report to a coagulation lab once a week in order to be monitored and in order to detect any early risk of bleeding complications. Even with this strict monitoring system, many patients on warfarin die every year from bleeding complications.

The potential clinical problems and business risk associated with developing drugs, which must past through the P450 metabolism "gauntlet", is markedly increased in the United States by the following two facts: 1) the number of prescriptions filled in this country has increased to about 3 billion per year or 10 per person, and 2) patients, particularly those that live longer and have more complex medical problems, tend to take multiple medications. The latter issue is important because the incidence of ADRs rises exponentially when subjects take more than four drugs. Although it is good practice to avoid polypharmacy, in many cases this is not possible because patients require different classes of drugs to effectively treat complex medical conditions.

The landscape of drug R&D is littered by failed drugs that were withdrawn by the FDA because they caused fatal ADRs involving CYP metabolism. These drugs were clinically effective and in many cases commercially successful. Notable drugs that were withdrawn due to ADR-related deaths involving CYP450 metabolism include terfenadine (February 1998), astemizole (July 1999) and cisapride (January 2000). In each of these cases, drug interactions involving CYP3A4 caused concentrations of the pharmaceutical agent to increase to such a degree that it significantly inhibited a particular type of potassium channel in the heart called $I_{Kr}$, which in turn, prolonged the QT interval and caused a potentially fatal form of ventricular tachyarrhythmia called torsades de pointes.

A warfarin analog that has a controllable and a predictable metabolic fate, not depending on CYP450, is therefore highly desirable and would be an important addition to the armamentarium of drugs available for treating atrial fibrillation patients. Certain warfarin analogs have been previously reported. See, for example, WO 02/085882, which is incorporated herein by reference.

SUMMARY OF THE INVENTION

The subject invention provides compounds and pharmaceutical compositions that are useful as anticoagulants or useful in anticoagulant therapy.

In a broad aspect, the invention provides compounds of formula I

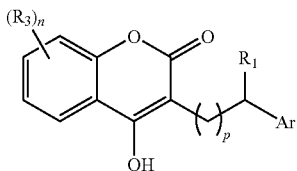

or pharmaceutically acceptable salts thereof, or isomers thereof, wherein $R_1$ is H or —($C_1$-$C_4$ alkyl)-$CO_2R_2$; wherein
$R_2$ is H or $C_1$-$C_6$ alkyl;
$R_3$ at each occurrence is independently halogen, OH, $C_1$-$C_6$ alkyl, $C_1$-$C_6$ alkoxy, $C_1$-$C_4$ haloalkyl, or $C_1$-$C_4$ haloalkoxy;
n is 0, 1, 2, 3, or 4,
p is 0, 1, or 2; and
Ar is an aryl group optionally substituted with at least one group that is —$COR_5$, —($C_1$-$C_6$ alkyl)-$COR_5$, —($C_0$-$C_6$ alkyl)-O—$R_6$, halogen, OH, amino, mono or dialkylamino, hydroxyalkyl, $C_1$-$C_4$ haloalkyl, or $C_1$-$C_4$ haloalkoxy, wherein $R_5$ is $C_1$-$C_8$ alkoxy optionally substituted with 1 or 2 groups that are independently OH, $C_1$-$C_4$ alkoxy, heterocycloalkyl, $C_3$-$C_7$ cycloalkyl, —$SO_2$—($C_1$-$C_4$ alkyl), —$SO_2$—($C_1$-$C_4$ haloalkyl), or —$SO_2$-phenyl, OH, amino, mono or dialkylamino, or $C_1$-$C_6$ haloalkoxy optionally substituted with 1 OH, wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino;
and
$R_6$ is $C_1$-$C_6$ alkanoyl, aryl $C_1$-$C_6$ alkanoyl, aryl $C_1$-$C_6$ alkyl, ($C_1$-$C_6$ alkyl)-O-aryl, or aryl, wherein the alkyl portions of the alkanoyl groups are optionally substituted with one or more halogens and wherein the aryl groups are optionally substituted at each substitutable position with a group that is $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

The compounds of formula I interact with VKER and/or are useful as anticoagulants and/or in anticoagulant therapy. The invention also, encompasses pharmaceutical compositions containing the compounds of Formula I, and methods employing such compounds or compositions in the treatment of coagulation disorders.

The invention also provides a method of treating a patient who has a coagulation disorder or who is at risk of developing a coagulation disorder. and who is in need of such treatment which comprises administration of a therapeutically effective amount of a compound of formula (I).

In another aspect, the invention provides methods of preparing the compounds of interest, as well as intermediates useful in preparing the compounds of interest.

BRIEF DESCRIPTION OF THE FIGURES

FIG. 1 shows VKER inhibitory activity of 3-(4-Hydroxy-2-oxo-2H-chromen-3-yl)-3-(4-trifluoromethoxy-phenyl)-propionic acid.

FIG. 2 shows VKER inhibitory activity of 4-(4-Hydroxy-2-oxo-2H-chromen-3-ylmethyl)-benzoic acid 2,2,3,3,3-pentafluoro-propyl ester.

FIG. 3 shows VKER inhibitory activity of 4-(4-Hydroxy-2-oxo-2H-chromen-3-ylmethyl)-benzoic acid 3,3,3-trifluoro-propyl ester.

FIG. 4 shows VKER inhibitory activity of 4-(4-Hydroxy-2-oxo-2H-chromen-3-ylmethyl)-benzoic acid 2,2,3,3,3-pentafluoro-1-methyl-propyl ester.

FIG. 5 shows VKER inhibitory activity of 4-(4-Hydroxy-2-oxo-2H-chromen-3-ylmethyl)-benzoic acid 4-fluoro-benzyl ester.

FIG. 6 shows VKER inhibitory activity of 4-(4-Hydroxy-2-oxo-2H-chromen-3-ylmethyl)-benzoic acid 2-(4-fluoro-phenoxy)-ethyl ester.

FIG. 7 shows VKER inhibitory activity of 4-(4-Hydroxy-2-oxo-2H-chromen-3-ylmethyl)-benzoic acid 2,2,2-trifluoro-1-methyl-ethyl ester.

FIG. 8 shows VKER inhibitory activity of 4-(4-Hydroxy-2-oxo-2H-chromen-3-ylmethyl)-benzoic acid 2,2,2-trifluoro-1-trifluoromethyl-ethyl ester.

FIG. 9 shows VKER inhibitory activity of 4-(4-Hydroxy-2-oxo-2H-chromen-3-ylmethyl)-benzoic acid 2,2,2-trifluoro-1-methyl-1-trifluoromethyl-ethyl ester.

FIG. 10 shows VKER inhibitory activity of warfarin.

FIG. 11 shows VKER inhibitory activity of 4-[(4-hydroxy-2-oxo-2H-chromen-3-yl)methyl]benzoic acid.

FIG. 12 shows the effect of fluorination on the metabolism by cytochrome P450 and esterase in pooled human microsomes. Peak area ratios are shown for microsomal incubations in the presence (solid bars) or absence (open bars) of NADPH. Solid bars represent CYP450+ esterase and open bars represent esterase alone.

FIG. 13 shows the effect of fluorination on the metabolism by cytochrome P450 and esterase in pooled human microsomes. Peak area ratios are shown for microsomal incubations in the presence (solid bars) or absence (open bars) of NADPH. Solid bars represent CYP450+ esterase and open bars represent esterase alone.

FIG. 14 shows the disappearance of a parent compound in pooled human microsomes containing NADPH, in the absence (solid bars) of paraoxon, or in the presence (open bars) of paraoxon, a known esterase inhibitor.

DETAILED DISCLOSURE

In one aspect, the invention provides compounds of formula I-a, i.e., compounds of formula I, wherein n is 0, 1, 2, or 3.

In another aspect, the invention provides compounds of formula I-b, i.e., compounds of formula I-a, wherein $R_1$ is H or —($C_1$-$C_4$ alkyl)-$CO_2R_2$; wherein $R_2$ is H.

In still another aspect, the invention provides compounds of formula I-c, i.e., compounds of formula I-b, wherein n is 1 and $R_3$ is halogen.

In yet another aspect, the invention provides compounds of formula I-d, i.e., compounds of formula I-b, wherein n is 0.

In still yet another aspect, the invention provides compounds of formula I-e, i.e., compounds of either formulas I-c or I-d, wherein p is 1.

In yet still another aspect, the invention provides compounds and salts of formula II, i.e., compounds of formula I having the formula:

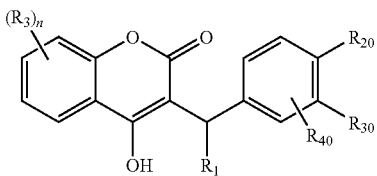

Formula II wherein:
n is 0, 1, or 2;
$R_1$ is H or $CH_2COOH$;
$R_3$ at each occurrence is independently halogen, OH, $C_1$-$C_6$ alkyl, $C_1$-$C_6$ alkoxy, $C_1$-$C_4$ haloalkyl, or $C_1$-$C_4$ haloalkoxy; and
$R_{20}$, $R_{30}$, and $R_{40}$ are independently H, —($C_0$-$C_6$ alkyl)-$COR_5$, —($C_1$-$C_6$ alkyl)-$COR_5$, —($C_0$-$C_6$ alkyl)-O—$R_6$, halogen, OH, amino, mono or dialkylamino, hydroxyalkyl, $C_1$-$C_4$ haloalkyl, or $C_1$-$C_4$ haloalkoxy, wherein
  $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl, OH, amino, mono or dialkylamino, or $C_1$-$C_6$ haloalkoxy optionally substituted with 1 OH, wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino; and
  $R_6$ is $C_1$-$C_6$ alkanoyl, phenyl $C_1$-$C_6$ alkanoyl, ($C_1$-$C_6$ alkyl)-O-phenyl, phenyl $C_1$-$C_6$ alkyl, or phenyl, wherein the alkyl portions of the alkanoyl groups are optionally substituted with one or more halogens and wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula II-a, i.e., compounds of formula II, wherein $R_1$ is H.

In still another aspect, the invention provides compounds of formula II-b, i.e., compounds of formula II-a, wherein $R_{20}$ is —($C_0$-$C_6$ alkyl)-$COR_5$.

In yet another aspect, the invention provides compounds of formula II-c, i.e., compounds of formula II-b, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula II-d, i.e., compounds of formula II-c, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula II-e, i.e., compounds of formula II-c, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula II-f, i.e., compounds of formula II-c, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula II-g, i.e., compounds of formula II-b, wherein $R_5$ is OH, amino, mono or dialkylamino, or $C_1$-$C_6$ haloalkoxy.

In yet another aspect, the invention provides compounds of formula II-h, i.e., compounds of formula II-g, wherein $R_5$ is amino, or mono or di($C_1$-$C_6$ alkyl)amino.

In yet still another aspect, the invention provides compounds of formula II-i, i.e., compounds of formula II-b, wherein $R_5$ is $C_1$-$C_6$ haloalkoxy optionally substituted with 1 OH.

In yet another aspect, the invention provides compounds of formula II-j, i.e., compounds of formula II-i, wherein $R_5$ is —$CH_2$C(halogen)$_2$C(halogen)$_3$, —$CH_2CH_2$C(halogen)$_3$, where each halogen is independently F or Cl.

In still another aspect, the invention provides compounds of formula II-k, i.e., compounds of formula II-j, wherein $R_5$ is —$CH_2CF_2CF_3$, —$CH_2CH_2CF_3$.

In another aspect, the invention provides compounds of formula II-l, i.e., compounds of formula II-i, wherein $R_5$ is —$CH(CH_3)$C(halogen)$_2$C(halogen)$_3$, —$CH(CH_2$halogen)$_2$, —$CH(CH_3)$C(halogen)$_3$, —$CH(C(halogen)_3)_2$, —$C(CH_3)(C$(halogen)$_3)_2$, or —$CH(OH)C$(halogen)$_3$, where each halogen is independently F or Cl.

In yet another aspect, the invention provides compounds of formula II-l1, i.e., compounds of formula II-i, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula II-m, i.e., compounds of formula II-l, wherein $R_5$ is —$C(CH_3)(C$(halogen)$_3)_2$ preferably each halogen is F.

In still yet another aspect, the invention provides compounds of formula II-n, i.e., compounds of formula II-l, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula II-o, i.e., compounds according to any one of formulas II-a, II-b, II-c, II-d, II-e, II-f, II-g, II-h, II-I, II-j, II-k, II-l, II-l1, II-m, or II-n, wherein at least one of $R_{30}$ and $R_{40}$ is H.

In still yet another aspect, the invention provides compounds of formula II-p, i.e., compounds of formula II-o, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula II-q, i.e., compounds of formula II-o, wherein both $R_{30}$ and $R_{40}$ are H.

In yet another aspect, the invention provides compounds of formula II-q1, i.e., compounds according to any one of formulas II-o, II-p, or II-q wherein n is 1.

In yet still another aspect, the invention provides compounds of formula II-q2, i.e., compounds of formula II-q1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula II-q3, i.e., compounds of formula II-q2, wherein $R_3$ is halogen, OH, $C_1$-$C_4$ alkyl, $C_1$-$C_4$ alkoxy, $CF_3$, or $OCF_3$.

In still another aspect, the invention provides compounds of formula II-q4, i.e., compounds of formula II-q3, wherein $R_3$ is halogen.

In yet another aspect, the invention provides compounds of formula II-q5, i.e., compounds of formula II-q3, wherein $R_3$ is OH, $C_1$-$C_4$ alkyl, or $C_1$-$C_4$ alkoxy.

In yet still another aspect, the invention provides compounds of formula II-q6, i.e., compounds of formula II-q3, wherein $R_3$ is $CF_3$ or $OCF_3$.

In still another aspect, the invention provides compounds of formula II-q7, i.e., compounds according to any one of formulas II-o, II-p, or II-q wherein n is 0.

In another aspect, the invention provides compounds of formula II-q8, i.e., compound according to formula II-a, wherein $R_{20}$ is ($C_0$-$C_6$ alkyl)-$OR_6$.

In yet another aspect, the invention provides compounds of formula II-q9, i.e., compounds of formula II-q8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula II-q10, i.e., compound according to formula II-q9, wherein $R_{20}$ is —($C_0$-$C_6$ alkyl)-O—$R_6$.

In still yet another aspect, the invention provides compounds of formula II-q11, i.e., compound according to formula II-q10, wherein $R_{20}$ is —($C_0$-$C_4$ alkyl)-O—$R_6$.

In another aspect, the invention provides compounds of formula II-q12, i.e., compounds according to any one of formulas II-q8, II-q9, II-q10, or II-q11, wherein at least one of $R_{30}$ and $R_{40}$ is H.

In still yet another aspect, the invention provides compounds of formula II-q13, i.e., compounds of formula II-q12, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula II-q14, i.e., compounds of formula II-q12, wherein both $R_{30}$ and $R_{40}$ are H.

In yet another aspect, the invention provides compounds of formula II-q15, i.e., compounds according to any one of formulas II-q8, II-q9, II-q10, II-q11, II-q12, II-q13, or II-q14 wherein n is 1.

In yet another aspect, the invention provides compounds of formula II-q16, i.e., compounds of formula II-q15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula II-q17, i.e., compounds of formula II-q16, wherein $R_3$ is halogen, OH, $C_1$-$C_4$ alkyl, $C_1$-$C_4$ alkoxy, $CF_3$, or $OCF_3$.

In still another aspect, the invention provides compounds of formula II-q18, i.e., compounds of formula II-q17, wherein $R_3$ is halogen.

In yet another aspect, the invention provides compounds of formula II-q19, i.e., compounds of formula II-q17, wherein $R_3$ is OH, $C_1$-$C_4$ alkyl, or $C_1$-$C_4$ alkoxy.

In yet still another aspect, the invention provides compounds of formula II-q20, i.e., compounds of formula II-q17, wherein $R_3$ is $CF_3$ or $OCF_3$.

In still another aspect, the invention provides compounds of formula II-q21, i.e., compounds according to any one of formulas II-q8, II-q9, II-q10, II-q11, II-q12, II-q13, or II-q14 wherein n is 0.

In another aspect, the invention provides compounds of formula II-r, i.e., compounds of formula II, wherein $R_1$ is $CH_2COOH$.

In still another aspect, the invention provides compounds of formula II-s, i.e., compounds of formula II-r, wherein $R_{20}$ is —($C_0$-$C_6$ alkyl)-$COR_5$.

In yet another aspect, the invention provides compounds of formula II-t, i.e., compounds of formula II-s, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula II-u, i.e., compounds of formula II-t, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula II-v, i.e., compounds of formula II-t, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula II-w, i.e., compounds of formula II-t, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula II-x, i.e., compounds of formula II-s, wherein $R_5$ is OH, amino, mono or dialkylamino, or $C_1$-$C_6$ haloalkoxy.

In yet another aspect, the invention provides compounds of formula II-y, i.e., compounds of formula II-x, wherein $R_5$ is amino, or mono or di($C_1$-$C_6$ alkyl)amino.

In yet still another aspect, the invention provides compounds of formula II-z, i.e., compounds of formula II-s, wherein $R_5$ is $C_1$-$C_6$ haloalkoxy optionally substituted with 1 OH.

In yet another aspect, the invention provides compounds of formula II-aa, i.e., compounds of formula II-z, wherein $R_5$ is —CH$_2$C(halogen)$_2$C(halogen)$_3$, —CH$_2$CH$_2$C(halogen)$_3$, where each halogen is independently F or Cl.

In still another aspect, the invention provides compounds of formula II-bb, i.e., compounds of formula II-aa, wherein R$_5$ is —CH$_2$CF$_2$CF$_3$, —CH$_2$CH$_2$CF$_3$.

In another aspect, the invention provides compounds of formula II-cc, i.e., compounds of formula II-z, wherein R$_5$ is —CH(CH$_3$)C(halogen)$_2$C(halogen)$_3$, —CH(CH$_2$halogen)$_2$, —CH(CH$_3$)C(halogen)$_3$, —CH(C(halogen)$_3$)$_2$, —C(CH$_3$)(C(halogen)$_3$)$_2$, or —CH(OH)C(halogen)$_3$, where each halogen is independently F or Cl.

In yet another aspect, the invention provides compounds of formula II-dd, i.e., compounds of formula II-cc, wherein R$_5$ is —CH(CH$_3$)CF$_2$CF$_3$, —CH(CH$_2$F)$_2$, —CH(CH$_3$)CF$_3$, —CH(CF$_3$)$_2$, —C(CH$_3$)(CF$_3$)$_2$, or —CH(OH)CF$_3$.

In still another aspect, the invention provides compounds of formula II-ee, i.e., compounds of formula II-cc wherein R$_5$ is —C(CH$_3$)(C(halogen)$_3$)$_2$ preferably each halogen is F.

In still yet another aspect, the invention provides compounds of formula II-ff, i.e., compounds of formula II-cc, wherein R$_5$ is —CH(OH)C(halogen)$_3$. In one case, the stereogenic center in R$_5$ has the S-configuration. In another case, the stereogenic center in R$_5$ has the R-configuration.

In another aspect, the invention provides compounds of formula II-gg, i.e., compounds according to any one of formulas II-r, II-s, II-t, II-u, II-v, II-w, II-x, II-y, II-z, II-aa, II-bb, II-cc, II-dd, II-ee, or II-ff, wherein at least one of R$_{30}$ and R$_{40}$ is H.

In still yet another aspect, the invention provides compounds of formula II-hh, i.e., compounds of formula II-gg, wherein one of R$_{30}$ and R$_{40}$ is halogen (in one aspect, F or Cl), OH, amino, mono or di(C$_1$-C$_4$)alkylamino, hydroxy(C$_1$-C$_4$)alkyl, CF$_3$, or OCF$_3$.

In yet still another aspect, the invention provides compounds of formula II-ii, i.e., compounds of formula II-gg, wherein both R$_{30}$ and R$_{40}$ are H.

In yet another aspect, the invention provides compounds of formula II-ii1, i.e., compounds according to any one of formulas II-gg, II-hh, or II-ii wherein n is 1.

In yet still another aspect, the invention provides compounds of formula II-ii2, i.e., compounds of formula II-ii1, wherein R$_3$ is halogen, OH, C$_1$-C$_4$ alkyl, C$_1$-C$_4$ alkoxy, C$_1$-C$_2$ haloalkyl, or C$_1$-C$_2$ haloalkoxy.

In still yet another aspect, the invention provides compounds of formula II-ii3, i.e., compounds of formula II-ii2, wherein R$_3$ is halogen, OH, C$_1$-C$_4$ alkyl, C$_1$-C$_4$ alkoxy, CF$_3$, or OCF$_3$.

In still another aspect, the invention provides compounds of formula II-ii4, i.e., compounds of formula II-ii3, wherein R$_3$ is halogen.

In yet another aspect, the invention provides compounds of formula II-ii5, i.e., compounds of formula II-ii2, wherein R$_3$ is OH, C$_1$-C$_4$ alkyl, or C$_1$-C$_4$ alkoxy.

In yet still another aspect, the invention provides compounds of formula II-ii6, i.e., compounds of formula II-ii2, wherein R$_3$ is CF$_3$ or OCF$_3$.

In still another aspect, the invention provides compounds of formula II-ii7, i.e., compounds according to any one of formulas II-gg, II-hh, or II-ii wherein n is 0.

In another aspect, the invention provides compounds of formula II-ii8, i.e., compound according to formula II-r, wherein R$_{20}$ is (C$_0$-C$_6$ alkyl)-OR$_6$.

In yet still another aspect, the invention provides compounds of formula II-ii9, i.e., compounds of formula II-ii8, wherein R$_6$ is C$_1$-C$_6$ alkanoyl, wherein the alkyl portion of the alkanoyl group is substituted with one or more halogens (preferably F or Cl, more preferably, F.) Or R$_6$ can be —(C$_1$-C$_4$ alkyl)-phenyl, —(C$_1$-C$_4$ alkanoyl)-phenyl, or phenyl, wherein the phenyl groups are optionally substituted with 1, 2, 3, 4, or 5 groups that are independently C$_1$-C$_4$ alkyl, C$_1$-C$_4$ alkoxy, halogen, OH, C$_1$-C$_4$ haloalkyl (such as CF$_3$), C$_1$-C$_4$ haloalkoxy (such as OCF$_3$), amino, or mono or di C$_1$-C$_6$ alkylamino.

In still yet another aspect, the invention provides compounds of formula II-ii10, i.e., compound according to formula II-ii9, wherein R$_{20}$ is —(C$_0$-C$_6$ alkyl)-O—R$_6$.

In still yet another aspect, the invention provides compounds of formula II-ii11, i.e., compound according to formula II-ii10, wherein R$_{20}$ is —(C$_0$-C$_4$ alkyl)-O—R$_6$.

In another aspect, the invention provides compounds of formula II-ii12, i.e., compounds according to any one of formulas II-ii8, II-ii9, II-ii10, or II-ii11, wherein at least one of R$_{30}$ and R$_{40}$ is H.

In still yet another aspect, the invention provides compounds of formula II-ii13, i.e., compounds of formula II-ii12, wherein one of R$_{30}$ and R$_{40}$ is halogen (in one aspect, F or Cl), OH, amino, mono or di(C$_1$-C$_4$)alkylamino, hydroxy(C$_1$-C$_4$)alkyl, CF$_3$, or OCF$_3$.

In yet still another aspect, the invention provides compounds of formula II-ii14, i.e., compounds of formula II-ii12, wherein both R$_{30}$ and R$_{40}$ are H.

In yet another aspect, the invention provides compounds of formula II-ii15, i.e., compounds according to any one of formulas II-ii8, II-ii9, II-ii10, II-ii11, II-ii12, II-ii13, or II-ii14 wherein n is 1.

In yet still another aspect, the invention provides compounds of formula II-ii16, i.e., compounds of formula II-ii15, wherein R$_3$ is halogen, OH, C$_1$-C$_4$ alkyl, C$_1$-C$_4$ alkoxy, C$_1$-C$_2$ haloalkyl, or C$_1$-C$_2$ haloalkoxy.

In still yet another aspect, the invention provides compounds of formula II-ii7, i.e., compounds of formula II-ii16, wherein R$_3$ is halogen, OH, C$_1$-C$_4$ alkyl, C$_1$-C$_4$ alkoxy, CF$_3$, or OCF$_3$.

In still another aspect, the invention provides compounds of formula II-ii18, i.e., compounds of formula II-ii17, wherein R$_3$ is halogen.

In yet another aspect, the invention provides compounds of formula II-ii19, i.e., compounds of formula II-ii17, wherein R$_3$ is OH, C$_1$-C$_4$ alkyl, or C$_1$-C$_4$ alkoxy.

In yet still another aspect, the invention provides compounds of formula II-ii20, i.e., compounds of formula II-ii17, wherein R$_3$ is CF$_3$ or OCF$_3$.

In still another aspect, the invention provides compounds of formula II-ii21, i.e., compounds according to any one of formulas II-ii8, II-ii9, II-ii10, II-ii11, II-ii12, II-ii13, or II-ii14 wherein n is 0.

In another aspect, the invention provides compounds of formula II-jj, i.e., compounds of formula II, wherein R$_1$ is H and R$_{30}$ is —(C$_0$-C$_6$ alkyl)-COR$_5$.

In yet another aspect, the invention provides compounds of formula II-kk, i.e., compounds of formula II-jj, wherein R$_5$ is C$_1$-C$_6$ alkoxy optionally substituted with 1 or 2 groups that are independently OH, C$_1$-C$_4$ alkoxy, piperidinyl, pyrrolidinyl, morpholinyl, piperazinyl, C$_3$-C$_7$ cycloalkyl, —SO$_2$—(C$_1$-C$_4$ alkyl), —SO$_2$—(C$_1$-C$_4$ haloalkyl), or —SO$_2$-phenyl wherein the cyclic portions of the above are optionally substituted at a substitutable position with groups that are independently C$_1$-C$_4$ alkyl, C$_1$-C$_4$ alkoxy, halogen, OH, C$_1$-C$_4$ haloalkyl, C$_1$-C$_4$ haloalkoxy, amino, or mono or dialkylamino.

In still yet another aspect, the invention provides compounds of formula II-ll, i.e., compounds of formula II-kk, wherein R$_5$ is C$_1$-C$_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula II-mm, i.e., compounds of formula II-kkc, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula II-nn, i.e., compounds of formula II-kk, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula II-oo, i.e., compounds of formula II-jj, wherein $R_5$ is OH, amino, mono or dialkylamino, or $C_1$-$C_6$ haloalkoxy.

In yet another aspect, the invention provides compounds of formula II-pp, i.e., compounds of formula II-oo, wherein $R_5$ is amino, or mono or di($C_1$-$C_6$ alkyl)amino.

In yet still another aspect, the invention provides compounds of formula II-qq, i.e., compounds of formula II-jj, wherein $R_5$ is $C_1$-$C_6$ haloalkoxy optionally substituted with 1 OH.

In yet another aspect, the invention provides compounds of formula II-rr, i.e., compounds of formula II-qq, wherein $R_5$ is —$CH_2C$(halogen)$_2C$(halogen)$_3$, —$CH_2CH_2C$(halogen)$_3$, where each halogen is independently F or Cl.

In still another aspect, the invention provides compounds of formula II-ss, i.e., compounds of formula II-rr, wherein $R_5$ is —$CH_2CF_2CF_3$, —$CH_2CH_2CF_3$.

In another aspect, the invention provides compounds of formula II-tt, i.e., compounds of formula II-qq, wherein $R_5$ is —$CH(CH_3)C$(halogen)$_2C$(halogen)$_3$, —$CH(CH_2$halogen)$_2$, —$CH(CH_3)C$(halogen)$_3$, —$CH(C$(halogen)$_3)_2$, —$C(CH_3)(C$(halogen)$_3)_2$, or —$CH(OH)C$(halogen)$_3$, where each halogen is independently F or Cl.

In yet another aspect, the invention provides compounds of formula II-uu, i.e., compounds of formula II-tt, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula II-vv, i.e., compounds of formula II-tt, wherein $R_5$ is —$C(CH_3)(C$(halogen)$_3)_2$ preferably each halogen is F.

In still yet another aspect, the invention provides compounds of formula II-ww, i.e., compounds of formula II-tt, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula II-xx, i.e., compounds according to any one of formulas II-jj, II-kk, II-ll, II-mm, II-nn, II-oo, II-pp, II-qq, II-rr, II-ss, II-tt, II-uu, II-vv, or II-ww, wherein at least one of $R_{20}$ and $R_{40}$ is H.

In still yet another aspect, the invention provides compounds of formula II-yy, i.e., compounds of formula II-xx, wherein one of $R_{20}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula II-zz, i.e., compounds of formula II-xx, wherein both $R_{20}$ and $R_{40}$ are H.

In yet another aspect, the invention provides compounds of formula II-zz1, i.e., compounds according to any one of formulas II-xx, II-yy, or II-zz wherein n is 1.

In yet still another aspect, the invention provides compounds of formula II-zz2, i.e., compounds of formula II-zz1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula II-zz3, i.e., compounds of formula II-zz2, wherein $R_3$ is halogen, OH, $C_1$-$C_4$ alkyl, $C_1$-$C_4$ alkoxy, $CF_3$, or $OCF_3$.

In still another aspect, the invention provides compounds of formula II-zz4, i.e., compounds of formula II-zz3, wherein $R_3$ is halogen.

In yet another aspect, the invention provides compounds of formula II-zz5, i.e., compounds of formula II-zz3, wherein $R_3$ is OH, $C_1$-$C_4$ alkyl, or $C_1$-$C_4$ alkoxy.

In yet still another aspect, the invention provides compounds of formula II-zz6, i.e., compounds of formula II-zz3, wherein $R_3$ is $CF_3$ or $OCF_3$.

In still another aspect, the invention provides compounds of formula II-zz7, i.e., compounds according to any one of formulas II-xx, II-yy, or II-zz wherein n is 0.

In another aspect, the invention provides compounds of formula II-zz8, i.e., compound according to formula II, wherein $R_1$ is H, and $R_{30}$ is ($C_0$-$C_6$ alkyl)-$OR_6$.

In yet still another aspect, the invention provides compounds of formula II-zz9, i.e., compounds of formula II-zz8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula II-zz10, i.e., compound according to formula II-zz9, wherein $R_{30}$ is —($C_0$-$C_6$ alkyl)-O—$R_6$.

In still yet another aspect, the invention provides compounds of formula II-zz11, i.e., compound according to formula II-zz10, wherein $R_{30}$ is —($C_0$-$C_4$ alkyl)-O—$R_6$.

In another aspect, the invention provides compounds of formula II-zz12, i.e., compounds according to any one of formulas II-zz8, II-zz9, II-zz10, or II-zz11, wherein at least one of $R_{20}$ and $R_{40}$ is H.

In still yet another aspect, the invention provides compounds of formula II-zz13, i.e., compounds of formula II-zz12, wherein one of $R_{20}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula II-zz14, i.e., compounds of formula II-zz12, wherein both $R_{20}$ and $R_{40}$ are H.

In yet another aspect, the invention provides compounds of formula II-zz15, i.e., compounds according to any one of formulas II-zz8, II-zz9, II-z10, II-zz11, II-zz12, II-zz13, or II-zz14 wherein n is 1.

In yet another aspect, the invention provides compounds of formula II-zz16, i.e., compounds of formula II-zz15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula II-zz17, i.e., compounds of formula II-zz16, wherein $R_3$ is halogen, OH, $C_1$-$C_4$ alkyl, $C_1$-$C_4$ alkoxy, $CF_3$, or $OCF_3$.

In still another aspect, the invention provides compounds of formula II-zz18, i.e., compounds of formula II-zz17, wherein $R_3$ is halogen.

In yet another aspect, the invention provides compounds of formula II-zz19, i.e., compounds of formula II-zz17, wherein $R_3$ is OH, $C_1$-$C_4$ alkyl, or $C_1$-$C_4$ alkoxy.

In yet still another aspect, the invention provides compounds of formula II-zz20, i.e., compounds of formula II-zz17, wherein $R_3$ is $CF_3$ or $OCF_3$.

In still another aspect, the invention provides compounds of formula II-zz21, i.e., compounds according to any one of formulas II-zz8, II-zz9, II-zz10, II-zz11, II-zz12, II-zz13, or II-zz14 wherein n is 0.

In another aspect, the invention provides compounds of formula II-aaa, i.e., compounds of formula II, wherein $R_1$ is $CH_2COOH$ and $R_{30}$ is —($C_0$-$C_6$ alkyl)-$COR_5$.

In yet another aspect, the invention provides compounds of formula II-bbb, i.e., compounds of formula II-aaa, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula II-ccc, i.e., compounds of formula II-bbb, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula II-ddd, i.e., compounds of formula II-bbb, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula II-eee, i.e., compounds of formula II-bbb, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula II-fff, i.e., compounds of formula II-aaa, wherein $R_5$ is OH, amino, mono or dialkylamino, or $C_1$-$C_6$ haloalkoxy.

In yet another aspect, the invention provides compounds of formula II-ggg, i.e., compounds of formula II-fff, wherein $R_5$ is amino, or mono or di($C_1$-$C_6$ alkyl)amino.

In yet still another aspect, the invention provides compounds of formula II-hhh, i.e., compounds of formula II-aaa, wherein $R_5$ is $C_1$-$C_6$ haloalkoxy optionally substituted with 1 OH.

In yet another aspect, the invention provides compounds of formula II-iii, i.e., compounds of formula II-hhh, wherein $R_5$ is —$CH_2C$(halogen)$_2C$(halogen)$_3$, —$CH_2CH_2C$(halogen)$_3$, where each halogen is independently F or Cl.

In still another aspect, the invention provides compounds of formula II-jjj, i.e., compounds of formula II-iii, wherein $R_5$ is —$CH_2CF_2CF_3$, —$CH_2CH_2CF_3$.

In another aspect, the invention provides compounds of formula II-kkk, i.e., compounds of formula II-hhh, wherein $R_5$ is —$CH(CH_3)C$(halogen)$_2C$(halogen)$_3$, —$CH(CH_2$ halogen)$_2$, —$CH(CH_3)C$(halogen)$_3$, —$CH(C$(halogen)$_3)_2$, —$C(CH_3)(C$(halogen)$_3)_2$, or —$CH(OH)C$(halogen)$_3$, where each halogen is independently F or Cl.

In yet another aspect, the invention provides compounds of formula II-lll, i.e., compounds of formula II-kkk, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula II-mmm, i.e., compounds of formula II-kkk wherein $R_5$ is —$C(CH_3)(C$(halogen)$_3)_2$ preferably each halogen is F.

In still yet another aspect, the invention provides compounds of formula II-nnn, i.e., compounds of formula II-kkk, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula II-ooo, i.e., compounds according to any one of formulas II-aaa, II-bbb, II-ccc, II-ddd, II-eee, II-fff, II-ggg, II-hhh, II-iii, II-jjj, II-kkk, II-lll, II-mmm, or II-nnn, wherein at least one of $R_{20}$ and $R_{40}$ is H.

In still yet another aspect, the invention provides compounds of formula II-ppp, i.e., compounds of formula II-ooo, wherein one of $R_{20}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula II-qqq, i.e., compounds of formula II-ooo, wherein both $R_{20}$ and $R_{40}$ are H.

In yet another aspect, the invention provides compounds of formula II-rrr, i.e., compounds according to any one of formulas II-ooo, II-ppp, or II-qqq wherein n is 1.

In yet still another aspect, the invention provides compounds of formula II-sss, i.e., compounds of formula II-rrr, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula II-ttt, i.e., compounds of formula II-sss, wherein $R_3$ is halogen, OH, $C_1$-$C_4$ alkyl, $C_1$-$C_4$ alkoxy, $CF_3$, or $OCF_3$.

In still another aspect, the invention provides compounds of formula II-uuu, i.e., compounds of formula II-ttt, wherein $R_3$ is halogen.

In yet another aspect, the invention provides compounds of formula II-vvv, i.e., compounds of formula I-ttt, wherein $R_3$ is OH, $C_1$-$C_4$ alkyl, or $C_1$-$C_4$ alkoxy.

In yet still another aspect, the invention provides compounds of formula II-www, i.e., compounds of formula II-ttt, wherein $R_3$ is $CF_3$ or $OCF_3$.

In still another aspect, the invention provides compounds of formula II-xxx, i.e., compounds according to any one of formulas II-ooo, II-ppp, or II-qqq wherein n is 0.

In another aspect, the invention provides compounds of formula II-xxx1, i.e., compound according to formula II, wherein $R_1$ is $CH_2CO_2H$, and $R_{30}$ is $(C_0\text{-}C_6\text{ alkyl})\text{-}OR_6$.

In yet still another aspect, the invention provides compounds of formula II-xxx2, i.e., compounds of formula II-xxx1, wherein $R_6$ is $C_1\text{-}C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula II-xxx3, i.e., compound according to formula II-xxx2, wherein $R_{30}$ is —($C_0$-$C_6$ alkyl)-O—$R_6$.

In still yet another aspect, the invention provides compounds of formula II-xxx4, i.e., compound according to formula II-xxx3, wherein $R_{30}$ is —($C_0$-$C_4$ alkyl)-O—$R_6$.

In another aspect, the invention provides compounds of formula II-xxx5, i.e., compounds according to any one of formulas II-xxx1, II-xxx2, II-xxx3, or II-xxx4, wherein at least one of $R_{20}$ and $R_{40}$ is H.

In still yet another aspect, the invention provides compounds of formula II-xxx6, i.e., compounds of formula II-xxx5, wherein one of $R_{20}$ and $R_{40}$ is halogen (in one aspect, F or Cl), OH, amino, mono or di($C_1$-$C_4$)alkylamino, hydroxy($C_1$-$C_4$)alkyl, $CF_3$, or $OCF_3$.

In yet still another aspect, the invention provides compounds of formula II-xxx7, i.e., compounds of formula II-xxx5, wherein both $R_{20}$ and $R_{40}$ are H.

In yet another aspect, the invention provides compounds of formula II-xxx8, i.e., compounds according to any one of formulas II-xxx1, II-xxx2, II-xxx3, II-xxx11, II-xxx4, II-xxx5, or II-xxx6 wherein n is 1.

In yet still another aspect, the invention provides compounds of formula II-xxx9, i.e., compounds of formula II-xxx8, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula II-xxx10, i.e., compounds of formula II-xxx9, wherein $R_3$ is halogen, OH, $C_1$-$C_4$ alkyl, $C_1$-$C_4$ alkoxy, $CF_3$, or $OCF_3$.

In still another aspect, the invention provides compounds of formula II-xxx11, i.e., compounds of formula II-xxx10, wherein $R_3$ is halogen.

In yet another aspect, the invention provides compounds of formula II-xxx12, i.e., compounds of formula II-xxx10, wherein $R_3$ is OH, $C_1$-$C_4$ alkyl, or $C_1$-$C_4$ alkoxy.

In yet still another aspect, the invention provides compounds of formula II-xxx13, i.e., compounds of formula II-xxx10, wherein $R_3$ is $CF_3$ or $OCF_3$.

In still another aspect, the invention provides compounds of formula II-xxx14, i.e., compounds according to any one of formulas II-xxx1, II-xxx2, II-xxx3, II-xxx4, II-xxx5, II-xxx6, or II-xxx7 wherein n is 0.

In another aspect, the invention provides compounds of formula III, i.e., compounds of formula I, where Ar is an optionally substituted naphthyl group of the formula:

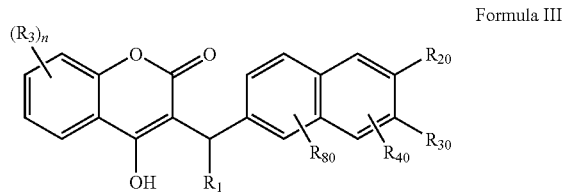

Formula III wherein:

n is 0, 1, or 2;

$R_1$ is H or $CH_2COOH$;

$R_3$ at each occurrence is independently halogen, OH, $C_1$-$C_6$ alkyl, $C_1$-$C_6$ alkoxy, $C_1$-$C_4$ haloalkyl, or $C_1$-$C_4$ haloalkoxy; and $R_{20}$, $R_{30}$, $R_{40}$, and $R_{80}$ are independently H, —($C_0$-$C_6$ alkyl)-$COR_5$, ($C_0$-$C_6$ alkyl)-O—$R_6$, halogen, OH, amino, mono or dialkylamino, hydroxyalkyl, $C_1$-$C_4$ haloalkyl, or $C_1$-$C_4$ haloalkoxy, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl, OH, amino, mono or dialkylamino, or $C_1$-$C_6$ haloalkoxy optionally substituted with 1 OH, wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino; and $R_6$ is $C_1$-$C_6$ alkanoyl, phenyl $C_1$-$C_6$ alkanoyl, ($C_1$-$C_6$ alkyl)-O-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula III-a, i.e., compounds of formula III, wherein $R_1$ is H.

In still another aspect, the invention provides compounds of formula III-b, i.e., compounds of formula III-a, wherein $R_{20}$ is —($C_0$-$C_6$ alkyl)-$COR_5$.

In yet another aspect, the invention provides compounds of formula III-c, i.e., compounds of formula III-b, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula III-d, i.e., compounds of formula III-c, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula III-e, i.e., compounds of formula III-c, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —SO₂-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula III-f, i.e., compounds of formula III-c, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula III-g, i.e., compounds of formula III-b, wherein $R_5$ is OH, amino, mono or dialkylamino, or $C_1$-$C_6$ haloalkoxy.

In yet another aspect, the invention provides compounds of formula III-h, i.e., compounds of formula III-g, wherein $R_5$ is amino, or mono or di($C_1$-$C_6$ alkyl)amino.

In yet still another aspect, the invention provides compounds of formula III-i, i.e., compounds of formula III-b, wherein $R_5$ is $C_1$-$C_6$ haloalkoxy optionally substituted with 1 OH.

In yet another aspect, the invention provides compounds of formula III-j, i.e., compounds of formula III-i, wherein $R_5$ is —CH₂C(halogen)₂C(halogen)₃, —CH₂CH₂C(halogen)₃, where each halogen is independently F or Cl.

In still another aspect, the invention provides compounds of formula III-k, i.e., compounds of formula III-j, wherein $R_5$ is —CH₂CF₂CF₃, —CH₂CH₂CF₃.

In another aspect, the invention provides compounds of formula III-l, i.e., compounds of formula III-i, wherein $R_5$ is —CH(CH₃)C(halogen)₂C(halogen)₃, —CH(CH₂halogen)₂, —CH(CH₃)C(halogen)₃, —CH(C(halogen)₃)₂, —C(CH₃)(C(halogen)₃)₂, or —CH(OH)C(halogen)₃, where each halogen is independently F or Cl.

In yet another aspect, the invention provides compounds of formula III-l1, i.e., compounds of formula III-i, wherein $R_5$ is —CH(CH₃)CF₂CF₃, —CH(CH₂F)₂, —CH(CH₃)CF₃, —CH(CF₃)₂, —C(CH₃)(CF₃)₂, or —CH(OH)CF₃.

In still another aspect, the invention provides compounds of formula III-m, i.e., compounds of formula III-l, wherein $R_5$ is —C(CH₃)(C(halogen)₃)₂ preferably each halogen is F.

In still yet another aspect, the invention provides compounds of formula III-n, i.e., compounds of formula III-l, wherein $R_5$ is —CH(OH)C(halogen)₃. In one case, the stereogenic center in $R_5$ has the S-configuration. In another case, the stereogenic center in $R_5$ has the R-configuration.

In another aspect, the invention provides compounds of formula III-o, i.e., compounds according to any one of formulas III-a, III-b, III-c, III-d, III-e, III-f, III-g, III-h, III-I, III-j, III-k, III-l, III-l1, III-m, or III-n, wherein at least one of $R_{30}$ and $R_{40}$ is H; and $R_{90}$ is H, Cl, or OCF₃.

In still yet another aspect, the invention provides compounds of formula III-p, i.e., compounds of formula III-o, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, CF₃, or OCF₃.

In yet still another aspect, the invention provides compounds of formula III-q, i.e., compounds of formula III-o, wherein both $R_{30}$ and $R_{40}$ are H.

In yet another aspect, the invention provides compounds of formula III-q1, i.e., compounds according to any one of formulas III-o, III-p, or III-q wherein n is 1.

In yet still another aspect, the invention provides compounds of formula III-q2, i.e., compounds of formula III-q1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-q3, i.e., compounds of formula III-q2, wherein $R_3$ is halogen, OH, $C_1$-$C_4$ alkyl, $C_1$-$C_4$ alkoxy, CF₃, or OCF₃.

In still another aspect, the invention provides compounds of formula III-q4, i.e., compounds of formula III-q3, wherein $R_3$ is halogen.

In yet another aspect, the invention provides compounds of formula III-q5, i.e., compounds of formula III-q3, wherein $R_3$ is OH, $C_1$-$C_4$ alkyl, or $C_1$-$C_4$ alkoxy.

In yet still another aspect, the invention provides compounds of formula III-q6, i.e., compounds of formula III-q3, wherein $R_3$ is CF₃ or OCF₃.

In still another aspect, the invention provides compounds of formula III-q7, i.e., compounds according to any one of formulas III-o, III-p, or III-q wherein n is 0.

In another aspect, the invention provides compounds of formula III-q8, i.e., compound according to formula III-a, wherein $R_{20}$ is —($C_0$-$C_6$ alkyl)-O—$R_6$.

In yet still another aspect, the invention provides compounds of formula III-q9, i.e., compounds of formula III-q8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as CF₃), $C_1$-$C_4$ haloalkoxy (such as OCF₃), amino, or mono or di $C_1$-$C_6$ alkylamino.

In still yet another aspect, the invention provides compounds of formula III-q10, i.e., compound according to formula III-q9, wherein $R_{20}$ is —($C_0$-$C_6$ alkyl)-O—$R_6$.

In still yet another aspect, the invention provides compounds of formula III-q11, i.e., compound according to formula III-q10, wherein $R_{20}$ is —($C_0$-$C_4$ alkyl)-O—$R_6$.

In another aspect, the invention provides compounds of formula III-q12, i.e., compounds according to any one of formulas III-q8, III-q9, III-q10, or III-q11, wherein at least one of $R_{30}$ and $R_{40}$ is H; and $R_{80}$ is H, Cl, or OCF₃.

In still yet another aspect, the invention provides compounds of formula III-q13, i.e., compounds of formula III-q12, wherein one of $R_{30}$ and $R_{40}$ is halogen (in one aspect, F or Cl), OH, amino, mono or di($C_1$-$C_4$)alkylamino, hydroxy ($C_1$-$C_4$)alkyl, CF₃, or OCF₃.

In yet still another aspect, the invention provides compounds of formula III-q14, i.e., compounds of formula III-q12, wherein both $R_{30}$ and $R_{40}$ are H.

In yet another aspect, the invention provides compounds of formula III-q15, i.e., compounds according to any one of formulas III-q8, III-q9, III-q10, III-q11, III-q12, III-q13, or III-q14 wherein n is 1.

In yet still another aspect, the invention provides compounds of formula III-q16, i.e., compounds of formula III-q15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-q17, i.e., compounds of formula III-q16, wherein $R_3$ is halogen, OH, $C_1$-$C_4$ alkyl, $C_1$-$C_4$ alkoxy, CF₃, or OCF₃.

In still another aspect, the invention provides compounds of formula III-q18, i.e., compounds of formula III-q17, wherein $R_3$ is halogen.

In yet another aspect, the invention provides compounds of formula III-q19, i.e., compounds of formula III-q17, wherein $R_3$ is OH, $C_1$-$C_4$ alkyl, or $C_1$-$C_4$ alkoxy.

In yet still another aspect, the invention provides compounds of formula III-q20, i.e., compounds of formula III-q17, wherein $R_3$ is $CF_3$ or $OCF_3$.

In still another aspect, the invention provides compounds of formula III-q21, i.e., compounds according to any one of formulas III-q8, III-q9, III-q10, III-q11, III-q12, III-q13, or III-q14 wherein n is 0.

In another aspect, the invention provides compounds of formula III-r, i.e., compounds of formula III, wherein $R_1$ is $CH_2COOH$.

In still another aspect, the invention provides compounds of formula III-s, i.e., compounds of formula III-r, wherein $R_{20}$ is —($C_0$-$C_6$ alkyl)-$COR_5$.

In yet another aspect, the invention provides compounds of formula III-t, i.e., compounds of formula III-s, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula III-u, i.e., compounds of formula III-t, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula III-v, i.e., compounds of formula III-t, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula III-w, i.e., compounds of formula III-t, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula III-x, i.e., compounds of formula III-s, wherein $R_5$ is OH, amino, mono or dialkylamino, or $C_1$-$C_6$ haloalkoxy.

In yet another aspect, the invention provides compounds of formula III-y, i.e., compounds of formula III-x, wherein $R_5$ is amino, or mono or di($C_1$-$C_6$ alkyl)amino.

In yet still another aspect, the invention provides compounds of formula III-z, i.e., compounds of formula III-s, wherein $R_5$ is $C_1$-$C_6$ haloalkoxy optionally substituted with 1 OH.

In yet another aspect, the invention provides compounds of formula III-aa, i.e., compounds of formula III-z, wherein $R_5$ is —$CH_2C(halogen)_2C(halogen)_3$, —$CH_2CH_2C(halogen)_3$, where each halogen is independently F or Cl.

In still another aspect, the invention provides compounds of formula III-bb, i.e., compounds of formula III-aa, wherein $R_5$ is —$CH_2CF_2CF_3$, —$CH_2CH_2CF_3$.

In another aspect, the invention provides compounds of formula III-cc, i.e., compounds of formula III-z, wherein $R_5$ is —$CH(CH_3)C(halogen)_2C(halogen)_3$, —$CH(CH_2halogen)_2$, —$CH(CH_3)C(halogen)_3$, —$CH(C(halogen)_3)_2$, —$C(CH_3)(C(halogen)_3)_2$, or —$CH(OH)C(halogen)_3$, where each halogen is independently F or Cl.

In yet another aspect, the invention provides compounds of formula III-dd, i.e., compounds of formula III-cc, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula III-ee, i.e., compounds of formula III-cc wherein $R_5$ is —$C(CH_3)(C(halogen)_3)_2$ preferably each halogen is F.

In still yet another aspect, the invention provides compounds of formula III-ff, i.e., compounds of formula III-cc, wherein $R_5$ is —$CH(OH)C(halogen)_3$. In one case, the stereogenic center in $R_5$ has the S-configuration. In another case, the stereogenic center in $R_5$ has the R-configuration.

In another aspect, the invention provides compounds of formula III-gg, i.e., compounds according to any one of formulas III-r, III-s, III-t, III-u, III-v, III-w, III-x, III-y, III-z, III-aa, III-bb, III-cc, III-dd, III-ee, or III-ff, wherein at least one of $R_{30}$ and $R_{40}$ is H; and $R_{80}$ is H, Cl, or $OCF_3$.

In still yet another aspect, the invention provides compounds of formula III-hh, i.e., compounds of formula III-gg, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula III-ii, i.e., compounds of formula III-gg, wherein both $R_{30}$ and $R_{40}$ are H.

In yet another aspect, the invention provides compounds of formula III-ii1, i.e., compounds according to any one of formulas III-gg, III-hh, or III-ii wherein n is 1.

In yet still another aspect, the invention provides compounds of formula III-ii2, i.e., compounds of formula III-ii1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-ii3, i.e., compounds of formula III-ii2, wherein $R_3$ is halogen, OH, $C_1$-$C_4$ alkyl, $C_1$-$C_4$ alkoxy, $CF_3$, or $OCF_3$.

In still another aspect, the invention provides compounds of formula III-ii4, i.e., compounds of formula III-ii3, wherein $R_3$ is halogen.

In yet another aspect, the invention provides compounds of formula III-ii5, i.e., compounds of formula III-ii2, wherein $R_3$ is OH, $C_1$-$C_4$ alkyl, or $C_1$-$C_4$ alkoxy.

In yet still another aspect, the invention provides compounds of formula III-ii6, i.e., compounds of formula III-ii2, wherein $R_3$ is $CF_3$ or $OCF_3$.

In still another aspect, the invention provides compounds of formula III-ii7, i.e., compounds according to any one of formulas III-gg, III-hh, or III-ii wherein n is 0.

In another aspect, the invention provides compounds of formula III-ii8, i.e., compound according to formula III, wherein $R_1$ and $CH_2CO_2H$, and $R_{20}$ is —($C_0$-$C_6$ alkyl)-O—$R_6$.

In yet still another aspect, the invention provides compounds of formula III-ii9, i.e., compounds of formula III-ii8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula III-ii10, i.e., compound according to formula III-ii9, wherein $R_{20}$ is —($C_0$-$C_6$ alkyl)-O—$R_6$.

In still yet another aspect, the invention provides compounds of formula III-ii11, i.e., compound according to formula III-ii10, wherein $R_{20}$ is —($C_0$-$C_4$ alkyl)-O—$R_6$.

In another aspect, the invention provides compounds of formula III-ii12, i.e., compounds according to any one of formulas III-ii8, III-ii9, III-ii10, or III-ii11, wherein at least one of $R_{30}$ and $R_{40}$ is H; and $R_{80}$ is H, Cl, or $OCF_3$.

In still yet another aspect, the invention provides compounds of formula III-ii13, i.e., compounds of formula III-ii12, wherein one of $R_{30}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula III-ii14, i.e., compounds of formula III-ii12, wherein both $R_{30}$ and $R_{40}$ are H.

In yet another aspect, the invention provides compounds of formula III-ii15, i.e., compounds according to any one of formulas III-ii8, III-ii9, III-ii10, III-ii11, III-ii12, III-ii13, or III-ii14 wherein n is 1.

In yet still another aspect, the invention provides compounds of formula III-ii 6, i.e., compounds of formula III-ii15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-ii17, i.e., compounds of formula III-ii16, wherein $R_3$ is halogen, OH, $C_1$-$C_4$ alkyl, $C_1$-$C_4$ alkoxy, $CF_3$, or $OCF_3$.

In still another aspect, the invention provides compounds of formula III-ii18, i.e., compounds of formula III-ii17, wherein $R_3$ is halogen.

In yet another aspect, the invention provides compounds of formula III-ii19, i.e., compounds of formula III-ii17, wherein $R_3$ is OH, $C_1$-$C_4$ alkyl, or $C_1$-$C_4$ alkoxy.

In yet still another aspect, the invention provides compounds of formula III-ii20, i.e., compounds of formula III-ii17, wherein $R_3$ is $CF_3$ or $OCF_3$.

In still another aspect, the invention provides compounds of formula III-ii21, i.e., compounds according to any one of formulas III-ii8, III-ii9, III-ii10, III-ii11, III-ii12, III-ii13, or III-ii14 wherein n is 0.

In another aspect, the invention provides compounds of formula III-jj, i.e., compounds of formula III, wherein $R_1$ is H and $R_{30}$ is —($C_0$-$C_6$ alkyl)-$COR_5$.

In yet another aspect, the invention provides compounds of formula III-kk, i.e., compounds of formula III-jj, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula III-ll, i.e., compounds of formula III-kk, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula III-mm, i.e., compounds of formula III-kk, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula III-nn, i.e., compounds of formula III-kk, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula III-oo, i.e., compounds of formula III-jj, wherein $R_5$ is OH, amino, mono or dialkylamino, or $C_1$-$C_6$ haloalkoxy.

In yet another aspect, the invention provides compounds of formula III-pp, i.e., compounds of formula III-oo, wherein $R_5$ is amino, or mono or di($C_1$-$C_6$ alkyl)amino.

In yet still another aspect, the invention provides compounds of formula III-qq, i.e., compounds of formula III-jj, wherein $R_5$ is $C_1$-$C_6$ haloalkoxy optionally substituted with 1 OH.

In yet another aspect, the invention provides compounds of formula III-rr, i.e., compounds of formula III-qq, wherein $R_5$ is —$CH_2C(halogen)_2C(halogen)_3$, —$CH_2CH_2C(halogen)_3$, where each halogen is independently F or Cl.

In still another aspect, the invention provides compounds of formula III-ss, i.e., compounds of formula III-rr, wherein $R_5$ is —$CH_2CF_2CF_3$, —$CH_2CH_2CF_3$.

In another aspect, the invention provides compounds of formula III-tt, i.e., compounds of formula III-qq, wherein $R_5$ is —$CH(CH_3)C(halogen)_2C(halogen)_3$, —$CH(CH_2halogen)_2$, —$CH(CH_3)C(halogen)_3$, —$CH(C(halogen)_3)_2$, —$C(CH_3)(C(halogen)_3)_2$, or —$CH(OH)C(halogen)_3$, where each halogen is independently F or Cl.

In yet another aspect, the invention provides compounds of formula III-uu, i.e., compounds of formula III-tt, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula III-vv, i.e., compounds of formula III-tt, wherein $R_5$ is —$C(CH_3)(C(halogen)_3)_2$ preferably each halogen is F.

In still yet another aspect, the invention provides compounds of formula III-ww, i.e., compounds of formula III-tt, wherein $R_5$ is —$CH(OH)C(halogen)_3$. In one case, the stereogenic center in $R_5$ has the S-configuration. In another case, the stereogenic center in $R_5$ has the R-configuration.

In another aspect, the invention provides compounds of formula III-xx, i.e., compounds according to any one of formulas III-jj, III-kk, III-ll, III-mm, III-nn, III-oo, III-pp, III-qq, III-rr, III-ss, III-tt, III-uu, III-vv, or III-ww, wherein at least one of $R_{20}$ and $R_{40}$ is H; and $R_{80}$ is H, Cl, or $OCF_3$.

In still yet another aspect, the invention provides compounds of formula III-yy, i.e., compounds of formula III-xx, wherein one of $R_{20}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula III-zz, i.e., compounds of formula III-xx, wherein both $R_{20}$ and $R_{40}$ are H.

In yet another aspect, the invention provides compounds of formula III-zz1, i.e., compounds according to any one of formulas III-xx, III-yy, or III-zz wherein n is 1.

In yet still another aspect, the invention provides compounds of formula III-zz2, i.e., compounds of formula III-zz1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-zz3, i.e., compounds of formula III-zz2, wherein $R_3$ is halogen, OH, $C_1$-$C_4$ alkyl, $C_1$-$C_4$ alkoxy, $CF_3$, or $OCF_3$.

In still another aspect, the invention provides compounds of formula III-zz4, i.e., compounds of formula III-zz3, wherein $R_3$ is halogen.

In yet another aspect, the invention provides compounds of formula III-zz5, i.e., compounds of formula III-zz3, wherein $R_3$ is OH, $C_1$-$C_4$ alkyl, or $C_1$-$C_4$ alkoxy.

In yet still another aspect, the invention provides compounds of formula III-zz6, i.e., compounds of formula III-zz3, wherein $R_3$ is $CF_3$ or $OCF_3$.

In still another aspect, the invention provides compounds of formula III-zz7, i.e., compounds according to any one of formulas III-xx, III-yy, or III-zz wherein n is 0.

In another aspect, the invention provides compounds of formula III-zz8, i.e., compound according to formula III, wherein $R_1$ is H and $R_{30}$ is —($C_0$-$C_6$ alkyl)-O—$R_6$.

In yet still another aspect, the invention provides compounds of formula III-zz9, i.e., compounds of formula III-zz8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula III-zz10, i.e., compound according to formula III-zz9, wherein $R_{30}$ is —($C_0$-$C_6$ alkyl)-O—$R_6$.

In still yet another aspect, the invention provides compounds of formula III-zz11, i.e., compound according to formula III-zz10, wherein $R_{30}$ is —($C_0$-$C_4$ alkyl)-O—$R_6$.

In another aspect, the invention provides compounds of formula III-zz12, i.e., compounds according to any one of formulas III-zz8, III-zz9, III-zz10, or III-zz11, wherein at least one of $R_{20}$ and $R_{40}$ is H; and $R_{80}$ is H, Cl, or $OCF_3$.

In still yet another aspect, the invention provides compounds of formula III-zz13, i.e., compounds of formula III-zz12, wherein one of $R_{20}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula III-zz14, i.e., compounds of formula III-zz12, wherein both $R_{20}$ and $R_{40}$ are H.

In yet another aspect, the invention provides compounds of formula III-zz15, i.e., compounds according to any one of formulas III-zz8, III-zz9, III-z10, III-zz11, III-zz12, III-zz13, or III-zz14 wherein n is 1.

In yet still another aspect, the invention provides compounds of formula III-zz16, i.e., compounds of formula III-zz15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-zz17, i.e., compounds of formula III-zz16, wherein $R_3$ is halogen, OH, $C_1$-$C_4$ alkyl, $C_1$-$C_4$ alkoxy, $CF_3$, or $OCF_3$.

In still another aspect, the invention provides compounds of formula III-zz18, i.e., compounds of formula III-zz17, wherein $R_3$ is halogen.

In yet another aspect, the invention provides compounds of formula III-zz19, i.e., compounds of formula III-zz17, wherein $R_3$ is OH, $C_1$-$C_4$ alkyl, or $C_1$-$C_4$ alkoxy.

In yet still another aspect, the invention provides compounds of formula III-zz20, i.e., compounds of formula III-zz17, wherein $R_3$ is $CF_3$ or $OCF_3$.

In still another aspect, the invention provides compounds of formula III-zz21, i.e., compounds according to any one of formulas III-zz8, III-zz9, III-zz10, III-zz11, III-zz12, III-zz13, or III-zz14 wherein n is 0.

In another aspect, the invention provides compounds of formula III-aaa, i.e., compounds of formula III, wherein $R_1$ is $CH_2COOH$ and $R_{30}$ is —($C_0$-$C_6$ alkyl)-$COR_5$.

In yet another aspect, the invention provides compounds of formula III-bbb, i.e., compounds of formula III-aaa, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula III-ccc, i.e., compounds of formula III-bbb, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula III-ddd, i.e., compounds of formula III-bbb, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula III-eee, i.e., compounds of formula III-bbb, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula III-fff, i.e., compounds of formula III-aaa, wherein $R_5$ is OH, amino, mono or dialkylamino, or $C_1$-$C_6$ haloalkoxy.

In yet another aspect, the invention provides compounds of formula III-ggg, i.e., compounds of formula III-fff, wherein $R_5$ is amino, or mono or di($C_1$-$C_6$ alkyl)amino.

In yet still another aspect, the invention provides compounds of formula III-hhh, i.e., compounds of formula III-aaa, wherein $R_5$ is $C_1$-$C_6$ haloalkoxy optionally substituted with 1 OH.

In yet another aspect, the invention provides compounds of formula III-iii, i.e., compounds of formula III-hhh, wherein $R_5$ is —$CH_2C$(halogen)$_2C$(halogen)$_3$, —$CH_2CH_2C$(halogen)$_3$, where each halogen is independently F or Cl.

In still another aspect, the invention provides compounds of formula III-jjj, i.e., compounds of formula III-iii, wherein $R_5$ is —$CH_2CF_2CF_3$, —$CH_2CH_2CF_3$.

In another aspect, the invention provides compounds of formula III-kkk, i.e., compounds of formula III-hhh, wherein $R_5$ is —$CH(CH_3)C$(halogen)$_2C$(halogen)$_3$, —$CH(CH_2$ halogen)$_2$, —$CH(CH_3)C$(halogen)$_3$, —$CH(C$(halogen)$_3)_2$, —$C(CH_3)(C$(halogen)$_3)_2$, or —$CH(OH)C$(halogen)$_3$, where each halogen is independently F or Cl.

In yet another aspect, the invention provides compounds of formula III-lll, i.e., compounds of formula III-kkk, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula III-mmm, i.e., compounds of formula III-kkk wherein $R_5$ is —$C(CH_3)(C$(halogen)$_3)_2$ preferably each halogen is F.

In still yet another aspect, the invention provides compounds of formula III-nnn, i.e., compounds of formula III-kkk, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula III-ooo, i.e., compounds according to any one of formulas III-aaa, III-bbb, III-ccc, III-ddd, III-eee, III-fff, III-ggg, III-hhh, III-iii, III-jjj, III-kkk, III-lll, III-mmm, or III-nnn, wherein at least one of $R_{20}$ and $R_{40}$ is H; and $R_{80}$ is H, Cl, or $OCF_3$.

In still yet another aspect, the invention provides compounds of formula III-ppp, i.e., compounds of formula III-ooo, wherein one of $R_{20}$ and $R_{40}$ is halogen (in one aspect, F or Cl), OH, amino, mono or di($C_1$-$C_4$)alkylamino, hydroxy($C_1$-$C_4$)alkyl, $CF_3$, or $OCF_3$.

In yet still another aspect, the invention provides compounds of formula III-qqq, i.e., compounds of formula III-ooo, wherein both $R_{20}$ and $R_{40}$ are H.

In yet another aspect, the invention provides compounds of formula III-rrr, i.e., compounds according to any one of formulas III-ooo, III-ppp, or III-qqq wherein n is 1.

In yet still another aspect, the invention provides compounds of formula III-sss, i.e., compounds of formula III-rrr, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-ttt, i.e., compounds of formula III-sss, wherein $R_3$ is halogen, OH, $C_1$-$C_4$ alkyl, $C_1$-$C_4$ alkoxy, $CF_3$, or $OCF_3$.

In still another aspect, the invention provides compounds of formula III-uuu, i.e., compounds of formula III-ttt, wherein $R_3$ is halogen.

In yet another aspect, the invention provides compounds of formula III-vvv, i.e., compounds of formula III-ttt, wherein $R_3$ is OH, $C_1$-$C_4$ alkyl, or $C_1$-$C_4$ alkoxy.

In yet still another aspect, the invention provides compounds of formula III-www, i.e., compounds of formula III-ttt, wherein $R_3$ is $CF_3$ or $OCF_3$.

In still another aspect, the invention provides compounds of formula III-xxx, i.e., compounds according to any one of formulas III-ooo, III-ppp, or III-qqq wherein n is 0.

In another aspect, the invention provides compounds of formula III-xxx1, i.e., compound according to formula III, wherein $R_1$ is $CH_2CO_2H$ and $R_{30}$ is —($C_0$-$C_6$ alkyl)-O—$R_6$.

In yet still another aspect, the invention provides compounds of formula III-xxx2, i.e., compounds of formula III-xxx1, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula III-xxx3, i.e., compound according to formula III-xxx2, wherein $R_{30}$ is —($C_0$-$C_6$ alkyl)-O—$R_6$.

In still yet another aspect, the invention provides compounds of formula III-xxx4, i.e., compound according to formula III-xxx3, wherein $R_{30}$ is —($C_0$-$C_4$ alkyl)-O—$R_6$.

In another aspect, the invention provides compounds of formula III-xxx5, i.e., compounds according to any one of formulas III-xxx1, III-xxx2, III-xxx3, or III-xxx4, wherein at least one of $R_{20}$ and $R_{40}$ is H; and $R_{80}$ is H, Cl, or $OCF_3$.

In still yet another aspect, the invention provides compounds of formula III-xxx6, i.e., compounds of formula III-xxx5, wherein one of $R_{20}$ and $R_{40}$ is halogen (in one aspect, F or Cl), OH, amino, mono or di($C_1$-$C_4$)alkylamino, hydroxy($C_1$-$C_4$)alkyl, $CF_3$, or $OCF_3$.

In yet still another aspect, the invention provides compounds of formula III-xxx7, i.e., compounds of formula III-xxx5, wherein both $R_{20}$ and $R_{40}$ are H.

In yet another aspect, the invention provides compounds of formula III-xxx8, i.e., compounds according to any one of formulas III-xxx1, III-xxx2, III-xxx3, III-xxx4, III-xxx5, III-xxx6, or III-xxx7, wherein n is 1.

In yet still another aspect, the invention provides compounds of formula III-xxx9, i.e., compounds of formula III-xxx8, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula III-xxx10, i.e., compounds of formula III-xxx9, wherein $R_3$ is halogen, OH, $C_1$-$C_4$ alkyl, $C_1$-$C_4$ alkoxy, $CF_3$, or $OCF_3$.

In still another aspect, the invention provides compounds of formula III-xxx11, i.e., compounds of formula III-xxx10, wherein $R_3$ is halogen.

In yet another aspect, the invention provides compounds of formula III-xxx12, i.e., compounds of formula III-xxx10, wherein $R_3$ is OH, $C_1$-$C_4$ alkyl, or $C_1$-$C_4$ alkoxy.

In yet still another aspect, the invention provides compounds of formula III-xxx13, i.e., compounds of formula III-xxx10, wherein $R_3$ is $CF_3$ or $OCF_3$.

In still another aspect, the invention provides compounds of formula III-xxx10, i.e., compounds according to any one of formulas III-xxx1, III-xxx2, III-xxx3, III-xxx4, III-xxx5, III-xxx6, or III-xxx7 wherein n is 0.

In another aspect, the invention provides compounds and salts of formula IV, i.e., compounds of formula I having the formula:

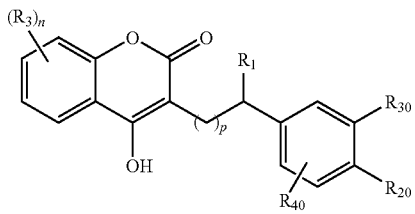

Formula IV wherein:
n is 0, 1, or 2;
p is 1 or 2;
$R_1$ is H or $CH_2COOH$;
$R_3$ at each occurrence is independently halogen, OH, $C_1$-$C_6$ alkyl, $C_1$-$C_6$ alkoxy, $C_1$-$C_4$ haloalkyl, or $C_1$-$C_4$ haloalkoxy; and
$R_{20}$, $R_{30}$, and $R_{40}$ are independently H, —($C_0$-$C_6$ alkyl)-$COR_5$, —($C_1$-$C_6$ alkyl)-$COR_5$, ($C_0$-$C_6$ alkyl)-O—$R_6$, halogen, OH, amino, mono or dialkylamino, hydroxyalkyl, $C_1$-$C_4$ haloalkyl, or $C_1$-$C_4$ haloalkoxy, wherein
$R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl, OH, amino, mono or dialkylamino, or $C_1$-$C_6$ haloalkoxy optionally substituted with 1 OH, wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino; and
$R_6$ is $C_1$-$C_6$ alkanoyl, phenyl $C_1$-$C_6$ alkanoyl, ($C_1$-$C_6$ alkyl)-O-phenyl, phenyl $C_1$-$C_6$ alkyl, or phenyl, wherein the alkyl portions of the alkanoyl groups are optionally substituted with one or more halogens and wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula IV-a, i.e., compounds of formula IV, wherein $R_1$ is H.

In still another aspect, the invention provides compounds of formula IV-b, i.e., compounds of formula IV-a, wherein $R_{20}$ is —($C_0$-$C_6$ alkyl)-$COR_5$.

In yet another aspect, the invention provides compounds of formula IV-c, i.e., compounds of formula IV-b, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula IV-d, i.e., compounds of formula IV-c, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula IV-e, i.e., compounds of formula IV-c, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula IV-f, i.e., compounds of formula IV-c, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula IV-g, i.e., compounds of formula IV-b, wherein $R_5$ is OH, amino, mono or dialkylamino, or $C_1$-$C_6$ haloalkoxy.

In yet another aspect, the invention provides compounds of formula IV-h, i.e., compounds of formula IV-g, wherein $R_5$ is amino, or mono or di($C_1$-$C_6$ alkyl)amino.

In yet still another aspect, the invention provides compounds of formula IV-i, i.e., compounds of formula IV-b, wherein $R_5$ is $C_1$-$C_6$ haloalkoxy optionally substituted with 1 OH.

In yet another aspect, the invention provides compounds of formula IV-j, i.e., compounds of formula IV-i, wherein $R_5$ is —$CH_2C(halogen)_2C(halogen)_3$, —$CH_2CH_2C(halogen)_3$, where each halogen is independently F or Cl.

In still another aspect, the invention provides compounds of formula IV-k, i.e., compounds of formula IV-j, wherein $R_5$ is —$CH_2CF_2CF_3$, —$CH_2CH_2CF_3$.

In another aspect, the invention provides compounds of formula IV-l, i.e., compounds of formula IV-i, wherein $R_5$ is —$CH(CH_3)C(halogen)_2C(halogen)_3$, —$CH(CH_2halogen)_2$, —$CH(CH_3)C(halogen)_3$, —$CH(C(halogen)_3)_2$, —$C(CH_3)(C(halogen)_3)_2$, or —$CH(OH)C(halogen)_3$, where each halogen is independently F or Cl.

In yet another aspect, the invention provides compounds of formula IV-ll, i.e., compounds of formula IV-i, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula IV-m, i.e., compounds of formula IV-l, wherein $R_5$ is —$C(CH_3)(C(halogen)_3)_2$ preferably each halogen is F.

In still yet another aspect, the invention provides compounds of formula IV-n, i.e., compounds of formula IV-l, wherein $R_5$ is —$CH(OH)C(halogen)_3$. In one case, the stereogenic center in $R_5$ has the S-configuration. In another case, the stereogenic center in $R_5$ has the R-configuration.

In another aspect, the invention provides compounds of formula IV-o, i.e., compounds according to any one of formulas IV-a, IV-b, IV-c, IV-d, IV-e, IV-f, IV-g, IV-h, IV-I, IV-j, IV-k, IV-l, IV-ll, IV-m, or IV-n, wherein at least one of $R_{30}$ and $R_{40}$ is H.

In still yet another aspect, the invention provides compounds of formula IV-p, i.e., compounds of formula IV-o, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula IV-q, i.e., compounds of formula IV-o, wherein both $R_{30}$ and $R_{40}$ are H.

In yet another aspect, the invention provides compounds of formula IV-q1, i.e., compounds according to any one of formulas IV-o, IV-p, or IV-q wherein n is 1.

In yet still another aspect, the invention provides compounds of formula IV-q2, i.e., compounds of formula IV-q1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-q3, i.e., compounds of formula IV-q2, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-q4, i.e., compounds of formula IV-q3, wherein $R_3$ is halogen.

In yet another aspect, the invention provides compounds of formula IV-q5, i.e., compounds of formula IV-q3, wherein $R_3$ is OH, $C_1$-$C_4$ alkyl, or $C_1$-$C_4$ alkoxy.

In yet still another aspect, the invention provides compounds of formula IV-q6, i.e., compounds of formula IV-q3, wherein $R_3$ is $CF_3$ or $OCF_3$.

In still another aspect, the invention provides compounds of formula IV-q7, i.e., compounds according to any one of formulas IV-o, IV-p, or IV-q wherein n is 0.

In another aspect, the invention provides compounds of formula IV-q8, i.e., compound according to formula IV-a, wherein $R_{20}$ is ($C_0$-$C_6$ alkyl)-$OR_6$.

In yet still another aspect, the invention provides compounds of formula IV-q9, i.e., compounds of formula IV-q8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula IV-q10, i.e., compound according to formula IV-q9, wherein $R_{20}$ is —($C_0$-$C_6$ alkyl)-O—$R_6$.

In still yet another aspect, the invention provides compounds of formula IV-q11, i.e., compound according to formula IV-q10, wherein $R_{20}$ is —($C_0$-$C_4$ alkyl)-O—$R_6$.

In another aspect, the invention provides compounds of formula IV-q12, i.e., compounds according to any one of formulas IV-q8, IV-q9, IV-q10, or IV-q11, wherein at least one of $R_{30}$ and $R_{40}$ is H.

In still yet another aspect, the invention provides compounds of formula IV-q13, i.e., compounds of formula IV-q12, wherein one of $R_{30}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula IV-q14, i.e., compounds of formula IV-q12, wherein both $R_{30}$ and $R_{40}$ are H.

In yet another aspect, the invention provides compounds of formula IV-q15, i.e., compounds according to any one of formulas IV-q8, IV-q9, IV-q10, IV-q11, IV-q12, IV-q13, or IV-q14 wherein n is 1.

In yet still another aspect, the invention provides compounds of formula IV-q16, i.e., compounds of formula IV-q15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-q17, i.e., compounds of formula IV-q16, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-q18, i.e., compounds of formula IV-q17, wherein $R_3$ is halogen.

In yet another aspect, the invention provides compounds of formula IV-q19, i.e., compounds of formula IV-q17, wherein $R_3$ is OH, $C_1$-$C_4$ alkyl, or $C_1$-$C_4$ alkoxy.

In yet still another aspect, the invention provides compounds of formula IV-q20, i.e., compounds of formula IV-q17, wherein $R_3$ is $CF_3$ or $OCF_3$.

In still another aspect, the invention provides compounds of formula IV-q21, i.e., compounds according to any one of formulas IV-q8, IV-q9, IV-q10, IV-q11, IV-q12, IV-q13, or IV-q14 wherein n is 0.

In another aspect, the invention provides compounds of formula IV-r, i.e., compounds of formula IV, wherein $R_1$ is $CH_2COOH$.

In still another aspect, the invention provides compounds of formula IV-s, i.e., compounds of formula IV-r, wherein $R_{20}$ is —($C_0$-$C_6$ alkyl)-$COR_5$.

In yet another aspect, the invention provides compounds of formula IV-t, i.e., compounds of formula IV-s, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula IV-u, i.e., compounds of formula IV-t, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula IV-v, i.e., compounds of formula IV-t, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula IV-w, i.e., compounds of formula IV-t, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula IV-x, i.e., compounds of formula IV-s, wherein $R_5$ is OH, amino, mono or dialkylamino, or $C_1$-$C_6$ haloalkoxy.

In yet another aspect, the invention provides compounds of formula IV-y, i.e., compounds of formula IV-x, wherein $R_5$ is amino, or mono or di($C_1$-$C_6$ alkyl)amino.

In yet still another aspect, the invention provides compounds of formula IV-z, i.e., compounds of formula IV-s, wherein $R_5$ is $C_1$-$C_6$ haloalkoxy optionally substituted with 1 OH.

In yet another aspect, the invention provides compounds of formula IV-aa, i.e., compounds of formula IV-z, wherein $R_5$ is —$CH_2C(halogen)_2C(halogen)_3$, —$CH_2CH_2C(halogen)_3$, where each halogen is independently F or Cl.

In still another aspect, the invention provides compounds of formula IV-bb, i.e., compounds of formula IV-aa, wherein $R_5$ is —$CH_2CF_2CF_3$, —$CH_2CH_2CF_3$.

In another aspect, the invention provides compounds of formula IV-cc, i.e., compounds of formula IV-z, wherein $R_5$ is —$CH(CH_3)C(halogen)_2C(halogen)_3$, —$CH(CH_2halogen)_2$, —$CH(CH_3)C(halogen)_3$, —$CH(C(halogen)_3)_2$, —$C(CH_3)(C(halogen)_3)_2$, or —$CH(OH)C(halogen)_3$, where each halogen is independently F or Cl.

In yet another aspect, the invention provides compounds of formula IV-dd, i.e., compounds of formula IV-cc, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula IV-ee, i.e., compounds of formula IV-cc wherein $R_5$ is —$C(CH_3)(C(halogen)_3)_2$ preferably each halogen is F.

In still yet another aspect, the invention provides compounds of formula IV-ff, i.e., compounds of formula IV-cc, wherein $R_5$ is —$CH(OH)C(halogen)_3$. In one case, the stereogenic center in $R_5$ has the S-configuration. In another case, the stereogenic center in $R_5$ has the R-configuration.

In another aspect, the invention provides compounds of formula IV-gg, i.e., compounds according to any one of formulas IV-r, IV-s, IV-t, IV-u, IV-v, IV-w, IV-x, IV-y, IV-z, IV-aa, IV-bb, IV-cc, IV-dd, IV-ee, or IV-ff, wherein at least one of $R_{30}$ and $R_{40}$ is H.

In still yet another aspect, the invention provides compounds of formula IV-hh, i.e., compounds of formula IV-gg, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula IV-ii, i.e., compounds of formula IV-gg, wherein both $R_{30}$ and $R_{40}$ are H.

In yet another aspect, the invention provides compounds of formula IV-ii1, i.e., compounds according to any one of formulas IV-gg, IV-hh, or IV-ii wherein n is 1.

In yet still another aspect, the invention provides compounds of formula IV-ii2, i.e., compounds of formula IV-ii1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-ii3, i.e., compounds of formula IV-ii2, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-ii4, i.e., compounds of formula IV-ii3, wherein $R_3$ is halogen.

In yet another aspect, the invention provides compounds of formula IV-ii5, i.e., compounds of formula IV-ii2, wherein $R_3$ is OH, $C_1$-$C_4$ alkyl, or $C_1$-$C_4$ alkoxy.

In yet still another aspect, the invention provides compounds of formula IV-ii6, i.e., compounds of formula IV-ii2, wherein $R_3$ is $CF_3$ or $OCF_3$.

In still another aspect, the invention provides compounds of formula IV-ii7, i.e., compounds according to any one of formulas IV-gg, IV-hh, or IV-ii wherein n is 0.

In another aspect, the invention provides compounds of formula IV-ii8, i.e., compound according to formula IV, wherein $R_1$ is $CH_2CO_2H$ and $R_{20}$ is ($C_0$-$C_6$ alkyl)-$OR_6$.

In yet still another aspect, the invention provides compounds of formula IV-ii9, i.e., compounds of formula IV-ii8, wherein R6 is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula IV-ii10, i.e., compound according to formula IV-ii9, wherein $R_{20}$ is —($C_0$-$C_6$ alkyl)-O—$R_6$.

In still yet another aspect, the invention provides compounds of formula IV-ii11, i.e., compound according to formula IV-ii10, wherein $R_{20}$ is —($C_0$-$C_4$ alkyl)-O—$R_6$.

In another aspect, the invention provides compounds of formula IV-ii12, i.e., compounds according to any one of formulas IV-ii8, IV-ii9, IV-ii10, or IV-ii11, wherein at least one of $R_{30}$ and $R_{40}$ is H.

In still yet another aspect, the invention provides compounds of formula IV-ii13, i.e., compounds of formula IV-ii12, wherein one of $R_{30}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula IV-ii14, i.e., compounds of formula IV-ii12, wherein both $R_{30}$ and $R_{40}$ are H.

In yet another aspect, the invention provides compounds of formula IV-ii15, i.e., compounds according to any one of formulas IV-ii8, IV-ii9, IV-ii10, IV-ii11, IV-ii12, IV-ii13, or IV-ii14 wherein n is 1.

In yet still another aspect, the invention provides compounds of formula IV-ii16, i.e., compounds of formula IV-ii15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-ii17, i.e., compounds of formula IV-ii16, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-ii18, i.e., compounds of formula IV-ii17, wherein $R_3$ is halogen.

In yet another aspect, the invention provides compounds of formula IV-ii19, i.e., compounds of formula IV-ii17, wherein $R_3$ is OH, $C_1$-$C_4$ alkyl, or $C_1$-$C_4$ alkoxy.

In yet still another aspect, the invention provides compounds of formula IV-ii20, i.e., compounds of formula IV-ii17, wherein $R_3$ is $CF_3$ or $OCF_3$.

In still another aspect, the invention provides compounds of formula IV-ii21, i.e., compounds according to any one of formulas IV-ii8, IV-ii9, IV-ii10, IV-ii11, IV-ii12, IV-ii13, or IV-ii14 wherein n is 0.

In another aspect, the invention provides compounds of formula IV-jj, i.e., compounds of formula IV, wherein $R_1$ is H and $R_{30}$ is —($C_0$-$C_6$ alkyl)-$COR_5$.

In yet another aspect, the invention provides compounds of formula IV-kk, i.e., compounds of formula IV-jj, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula IV-ll, i.e., compounds of formula IV-kk, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula IV-mm, i.e., compounds of formula IV-kk, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula IV-nn, i.e., compounds of formula IV-kk, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula IV-oo, i.e., compounds of formula IV-jj, wherein $R_5$ is OH, amino, mono or dialkylamino, or $C_1$-$C_6$ haloalkoxy.

In another aspect, the invention provides compounds of formula IV-pp, i.e., compounds of formula IV-oo, wherein $R_5$ is amino, or mono or di($C_1$-$C_6$ alkyl)amino.

In yet still another aspect, the invention provides compounds of formula IV-qq, i.e., compounds of formula IV-jj, wherein $R_5$ is $C_1$-$C_6$ haloalkoxy optionally substituted with 1 OH.

In yet another aspect, the invention provides compounds of formula IV-rr, i.e., compounds of formula IV-qq, wherein $R_5$ is —$CH_2C(halogen)_2C(halogen)_3$, —$CH_2CH_2C(halogen)_3$, where each halogen is independently F or Cl.

In still another aspect, the invention provides compounds of formula IV-ss, i.e., compounds of formula IV-rr, wherein $R_5$ is —$CH_2CF_2CF_3$, —$CH_2CH_2CF_3$.

In another aspect, the invention provides compounds of formula IV-tt, i.e., compounds of formula IV-qq, wherein $R_5$ is —$CH(CH_3)C(halogen)_2C(halogen)_3$, —$CH(CH_2halogen)_2$, —$CH(CH_3)C(halogen)_3$, —$CH(C(halogen)_3)_2$, —$C(CH_3)(C(halogen)_3)_2$, or —$CH(OH)C(halogen)_3$, where each halogen is independently F or Cl.

In yet another aspect, the invention provides compounds of formula IV-uu, i.e., compounds of formula IV-tt, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula IV-vv, i.e., compounds of formula IV-tt, wherein $R_5$ is —$C(CH_3)(C(halogen)_3)_2$ preferably each halogen is F.

In still yet another aspect, the invention provides compounds of formula IV-ww, i.e., compounds of formula IV-tt, wherein $R_5$ is —$CH(OH)C(halogen)_3$. In one case, the stereogenic center in $R_5$ has the S-configuration. In another case, the stereogenic center in $R_5$ has the R-configuration.

In another aspect, the invention provides compounds of formula IV-xx, i.e., compounds according to any one of formulas IV-jj, IV-kk, IV-ll, IV-mm, IV-nn, IV-oo, IV-pp, IV-qq, IV-rr, IV-ss, IV-tt, IV-uu, IV-vv, or IV-ww, wherein at least one of $R_{20}$ and $R_{40}$ is H.

In still yet another aspect, the invention provides compounds of formula IV-yy, i.e., compounds of formula IV-xx, wherein one of $R_{20}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula IV-zz, i.e., compounds of formula IV-xx, wherein both $R_{20}$ and $R_{40}$ are H.

In yet another aspect, the invention provides compounds of formula IV-zz1, i.e., compounds according to any one of formulas IV-xx, IV-yy, or IV-zz wherein n is 1.

In yet still another aspect, the invention provides compounds of formula IV-zz2, i.e., compounds of formula IV-zz1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-zz3, i.e., compounds of formula IV-zz2, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-zz4, i.e., compounds of formula IV-zz3, wherein $R_3$ is halogen.

In yet another aspect, the invention provides compounds of formula IV-zz5, i.e., compounds of formula IV-zz3, wherein $R_3$ is OH, $C_1$-$C_4$ alkyl, or $C_1$-$C_4$ alkoxy.

In yet still another aspect, the invention provides compounds of formula IV-zz6, i.e., compounds of formula IV-zz3, wherein $R_3$ is $CF_3$ or $OCF_3$.

In still another aspect, the invention provides compounds of formula IV-zz7, i.e., compounds according to any one of formulas IV-xx, IV-yy, or IV-zz wherein n is 0.

In another aspect, the invention provides compounds of formula IV-zz8, i.e., compound according to formula IV, wherein $R_1$ is H and $R_{30}$ is ($C_0$-$C_6$ alkyl)-$OR_6$.

In yet still another aspect, the invention provides compounds of formula IV-zz9, i.e., compounds of formula IV-zz8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula IV-zz10, i.e., compound according to formula IV-zz9, wherein $R_{30}$ is —($C_0$-$C_6$ alkyl)-O—$R_6$.

In still yet another aspect, the invention provides compounds of formula IV-zz11, i.e., compound according to formula IV-zz10, wherein $R_{30}$ is —($C_0$-$C_4$ alkyl)-O—$R_6$.

In another aspect, the invention provides compounds of formula IV-zz12, i.e., compounds according to any one of formulas IV-zz8, IV-zz9, IV-zz10, or IV-zz11, wherein at least one of $R_{20}$ and $R_{40}$ is H.

In still yet another aspect, the invention provides compounds of formula IV-zz13, i.e., compounds of formula IV-zz12, wherein one of $R_{20}$ and $R_{40}$ is halogen (in one aspect, F or Cl), OH, amino, mono or di($C_1$-$C_4$)alkylamino, hydroxy($C_1$-$C_4$)alkyl, $CF_3$, or $OCF_3$.

In yet still another aspect, the invention provides compounds of formula IV-zz14, i.e., compounds of formula IV-zz12, wherein both $R_{20}$ and $R_{40}$ are H.

In yet another aspect, the invention provides compounds of formula IV-zz15, i.e., compounds according to any one of formulas IV-zz8, IV-zz9, IV-z10, IV-zz11, IV-zz12, IV-zz13, or IV-zz14 wherein n is 1.

In yet still another aspect, the invention provides compounds of formula IV-zz16, i.e., compounds of formula IV-zz15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-zz17, i.e., compounds of formula IV-zz16, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-zz18, i.e., compounds of formula IV-zz17, wherein $R_3$ is halogen.

In yet another aspect, the invention provides compounds of formula IV-zz19, i.e., compounds of formula IV-zz17, wherein $R_3$ is OH, $C_1$-$C_4$ alkyl, or $C_1$-$C_4$ alkoxy.

In yet still another aspect, the invention provides compounds of formula IV-zz20, i.e., compounds of formula IV-zz17, wherein $R_3$ is $CF_3$ or $OCF_3$.

In still another aspect, the invention provides compounds of formula IV-zz21, i.e., compounds according to any one of formulas IV-zz8, IV-zz9, IV-zz10, IV-zz11, IV-zz12, IV-zz13, or IV-zz14 wherein n is 0.

In another aspect, the invention provides compounds of formula IV-aaa, i.e., compounds of formula IV, wherein $R_1$ is $CH_2COOH$ and $R_{30}$ is —($C_0$-$C_6$ alkyl)-$COR_5$.

In yet another aspect, the invention provides compounds of formula IV-bbb, i.e., compounds of formula IV-aaa, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula IV-ccc, i.e., compounds of formula IV-bbb, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula IV-ddd, i.e., compounds of formula IV-bbb, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula IV-eee, i.e., compounds of formula IV-bbb, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula IV-fff, i.e., compounds of formula IV-aaa, wherein $R_5$ is OH, amino, mono or dialkylamino, or $C_1$-$C_6$ haloalkoxy.

In yet another aspect, the invention provides compounds of formula IV-ggg, i.e., compounds of formula IV-fff, wherein $R_5$ is amino, or mono or di($C_1$-$C_6$ alkyl)amino.

In yet still another aspect, the invention provides compounds of formula IV-hhh, i.e., compounds of formula IV-aaa, wherein $R_5$ is $C_1$-$C_6$ haloalkoxy optionally substituted with 1 OH.

In yet another aspect, the invention provides compounds of formula IV-iii, i.e., compounds of formula IV-hhh, wherein $R_5$ is —$CH_2C$(halogen)$_2$C(halogen)$_3$, —$CH_2CH_2C$(halogen)$_3$, where each halogen is independently F or Cl.

In still another aspect, the invention provides compounds of formula IV-jjj, i.e., compounds of formula IV-iii, wherein $R_5$ is —$CH_2CF_2CF_3$, —$CH_2CH_2CF_3$.

In another aspect, the invention provides compounds of formula IV-kkk, i.e., compounds of formula IV-hhh, wherein $R_5$ is —$CH(CH_3)C$(halogen)$_2$C(halogen)$_3$, —$CH(CH_2$ halogen)$_2$, —$CH(CH_3)C$(halogen)$_3$, —$CH(C$(halogen)$_3)_2$, —$C(CH_3)(C$(halogen)$_3)_2$, or —$CH(OH)C$(halogen)$_3$, where each halogen is independently F or Cl.

In yet another aspect, the invention provides compounds of formula IV-lll, i.e., compounds of formula IV-kkk, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula IV-mmm, i.e., compounds of formula IV-kkk wherein $R_5$ is —$C(CH_3)(C$(halogen)$_3)_2$ preferably each halogen is F.

In still yet another aspect, the invention provides compounds of formula IV-nnn, i.e., compounds of formula IV-kkk, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula IV-ooo, i.e., compounds according to any one of formulas IV-aaa, IV-bbb, IV-ccc, IV-ddd, IV-eee, IV-fff, IV-ggg, IV-hhh, IV-iii, IV-jjj, IV-kkk, IV-lll, IV-mmm, or IV-nnn, wherein at least one of $R_{20}$ and $R_{40}$ is H.

In still yet another aspect, the invention provides compounds of formula IV-ppp, i.e., compounds of formula IV-ooo, wherein one of $R_{20}$ and $R_{40}$ is halogen (in one aspect, F or Cl), OH, amino, mono or di($C_1$-$C_4$)alkylamino, hydroxy($C_1$-$C_4$)alkyl, $CF_3$, or $OCF_3$.

In yet still another aspect, the invention provides compounds of formula IV-qqq, i.e., compounds of formula IV-ooo, wherein both $R_{20}$ and $R_{40}$ are H.

In yet another aspect, the invention provides compounds of formula IV-rrr, i.e., compounds according to any one of formulas IV-ooo, IV-ppp, or IV-qqq wherein n is 1.

In yet still another aspect, the invention provides compounds of formula IV-sss, i.e., compounds of formula IV-rrr, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula IV-ttt, i.e., compounds of formula IV-sss, wherein $R_3$ is halogen, OH, $C_1$-$C_4$ alkyl, $C_1$-$C_4$ alkoxy, $CF_3$, or $OCF_3$.

In still another aspect, the invention provides compounds of formula IV-uuu, i.e., compounds of formula IV-ttt, wherein $R_3$ is halogen.

In yet another aspect, the invention provides compounds of formula IV-vvv, i.e., compounds of formula IV-ttt, wherein $R_3$ is OH, $C_1$-$C_4$ alkyl, or $C_1$-$C_4$ alkoxy.

In yet still another aspect, the invention provides compounds of formula IV-www, i.e., compounds of formula IV-ttt, wherein $R_3$ is $CF_3$ or $OCF_3$.

In still another aspect, the invention provides compounds of formula IV-xxx, i.e., compounds according to any one of formulas IV-ooo, IV-ppp, or IV-qqq wherein n is 0.

In another aspect, the invention provides compounds of formula IV-xxx1, i.e., compound according to formula IV, wherein $R_1$ is $CH_2CO_2H$ and $R_{30}$ is $(C_0-C_6\ alkyl)-OR_6$.

In yet still another aspect, the invention provides compounds of formula IV-xxx2, i.e., compounds of formula IV-xxx1, wherein $R_6$ is $C_1-C_6$ alkanoyl, wherein the alkyl portion of the alkanoyl group is substituted with one or more halogens (preferably F or Cl, more preferably, F.) Or $R_6$ can be $—(C_1-C_4\ alkyl)$-phenyl, $—(C_1-C_4\ alkanoyl)$-phenyl, or phenyl, wherein the phenyl groups are optionally substituted with 1, 2, 3, 4, or 5 groups that are independently $C_1-C_4$ alkyl, $C_1-C_4$ alkoxy, halogen, OH, $C_1-C_4$ haloalkyl (such as $CF_3$), $C_1-C_4$ haloalkoxy (such as $OCF_3$), amino, or mono or di $C_1-C_6$ alkylamino.

In still yet another aspect, the invention provides compounds of formula IV-xxx3, i.e., compound according to formula IV-xxx2, wherein $R_{30}$ is $—(C_0-C_6\ alkyl)-O—R_6$.

In still yet another aspect, the invention provides compounds of formula IV-xxx4, i.e., compound according to formula IV-xxx3, wherein $R_{30}$ is $—(C_0-C_4\ alkyl)-O—R_6$.

In another aspect, the invention provides compounds of formula IV-xxx5, i.e., compounds according to any one of formulas IV-xxx1, IV-xxx2, IV-xxx3, or IV-xxx4, wherein at least one of $R_{20}$ and $R_{40}$ is H.

In still yet another aspect, the invention provides compounds of formula IV-xxx6, i.e., compounds of formula IV-xxx5, wherein one of $R_{20}$ and $R_{40}$ is halogen (in one aspect, F or Cl), OH, amino, mono or di($C_1-C_4$)alkylamino, hydroxy($C_1-C_4$)alkyl, $CF_3$, or $OCF_3$.

In yet still another aspect, the invention provides compounds of formula IV-xxx7, i.e., compounds of formula IV-xxx5, wherein both $R_{20}$ and $R_{40}$ are H.

In yet another aspect, the invention provides compounds of formula IV-xxx8, i.e., compounds according to any one of formulas IV-xxx1, IV-xxx2, IV-xxx3, IV-xxx11, IV-xxx4, IV-xxx5, or IV-xxx6 wherein n is 1.

In yet still another aspect, the invention provides compounds of formula IV-xxx9, i.e., compounds of formula IV-xxx8, wherein $R_3$ is halogen, OH, $C_1-C_4$ alkyl, $C_1-C_4$ alkoxy, $C_1-C_2$ haloalkyl, or $C_1-C_2$ haloalkoxy.

In still yet another aspect, the invention provides compounds of formula IV-xxx10, i.e., compounds of formula IV-xxx9, wherein $R_3$ is halogen, OH, $C_1-C_4$ alkyl, $C_1-C_4$ alkoxy, $CF_3$, or $OCF_3$.

In still another aspect, the invention provides compounds of formula IV-xxx11, i.e., compounds of formula IV-xxx10, wherein $R_3$ is halogen.

In yet another aspect, the invention provides compounds of formula IV-xxx12, i.e., compounds of formula IV-xxx10, wherein $R_3$ is OH, $C_1-C_4$ alkyl, or $C_1-C_4$ alkoxy.

In yet still another aspect, the invention provides compounds of formula IV-xxx13, i.e., compounds of formula IV-xxx10, wherein $R_3$ is $CF_3$ or $OCF_3$.

In still another aspect, the invention provides compounds of formula IV-xxx14, i.e., compounds according to any one of formulas IV-xxx1, IV-xxx2, IV-xxx3, IV-xxx4, IV-xxx5, IV-xxx6, or IV-xxx7 wherein n is 0.

In another aspect, the invention provides compounds of formula V, i.e., compounds of formula I, where Ar is an optionally substituted naphthyl group of the formula:

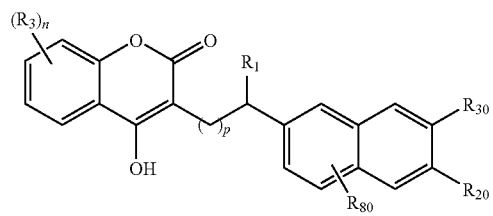

Formula V wherein:
n is 0, 1, or 2;
p is 1 or 2;
$R_1$ is H or $CH_2COOH$;
$R_3$ at each occurrence is independently halogen, OH, $C_1-C_6$ alkyl, $C_1-C_6$ alkoxy, $C_1-C_4$ haloalkyl, or $C_1-C_4$ haloalkoxy; and
$R_{20}$, $R_{30}$, $R_{40}$, and $R_{80}$ are independently H, $—(C_0-C_6\ alkyl)-COR_5$, $—(C_1-C_6\ alkyl)-COR_5$, $(C_0-C_6\ alkyl)-O—R_6$, halogen, OH, amino, mono or dialkylamino, hydroxyalkyl, $C_1-C_4$ haloalkyl, or $C_1-C_4$ haloalkoxy, wherein
  $R_5$ is $C_1-C_6$ alkoxy optionally substituted with 1 or 2 groups that are independently OH, $C_1-C_4$ alkoxy, piperidinyl, pyrrolidinyl, morpholinyl, piperazinyl, $C_3-C_7$ cycloalkyl, $—SO_2—(C_1-C_4\ alkyl)$, $—SO_2—(C_1-C_4\ haloalkyl)$, or $—SO_2$-phenyl, OH, amino, mono or dialkylamino, or $C_1-C_6$ haloalkoxy optionally substituted with 1 OH, wherein the cyclic portions of the above are optionally substituted at a substitutable position with groups that are independently $C_1-C_4$ alkyl, $C_1-C_4$ alkoxy, halogen, OH, $C_1-C_4$ haloalkyl, $C_1-C_4$ haloalkoxy, amino, or mono or dialkylamino;
and
  $R_6$ is $C_1-C_6$ alkanoyl, phenyl $C_1-C_6$ alkanoyl, $(C_1-C_6\ alkyl)$-O-phenyl, or phenyl, wherein the phenyl groups are optionally substituted with 1, 2, 3, 4, or 5 groups that are independently $C_1-C_4$ alkyl, $C_1-C_4$ alkoxy, halogen, OH, $C_1-C_4$ haloalkyl, $C_1-C_4$ haloalkoxy, amino, or mono or dialkylamino.

In another aspect, the invention provides compounds of formula V-a, i.e., compounds of formula V, wherein $R_1$ is H.

In still another aspect, the invention provides compounds of formula V-b, i.e., compounds of formula V-a, wherein $R_{20}$ is $—(C_0-C_6\ alkyl)-COR_5$.

In yet another aspect, the invention provides compounds of formula V-c, i.e., compounds of formula V-b, wherein $R_5$ is $C_1-C_6$ alkoxy optionally substituted with 1 or 2 groups that are independently OH, $C_1-C_4$ alkoxy, piperidinyl, pyrrolidinyl, morpholinyl, piperazinyl, $C_3-C_7$ cycloalkyl, $—SO_2—(C_1-C_4\ alkyl)$, $—SO_2—(C_1-C_4\ haloalkyl)$, or $—SO_2$-phenyl wherein the cyclic portions of the above are optionally substituted at a substitutable position with groups that are independently $C_1-C_4$ alkyl, $C_1-C_4$ alkoxy, halogen, OH, $C_1-C_4$ haloalkyl, $C_1-C_4$ haloalkoxy, amino, or mono or dialkylamino.

In still yet another aspect, the invention provides compounds of formula V-d, i.e., compounds of formula V-c, wherein $R_5$ is $C_1-C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1-C_4$ alkyl, $C_1-C_4$ alkoxy, halogen, OH, $C_1-C_4$ haloalkyl, $C_1-C_4$ haloalkoxy, amino, or mono or dialkylamino.

In still another aspect, the invention provides compounds of formula V-e, i.e., compounds of formula V-c, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula V-f, i.e., compounds of formula V-c, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula V-g, i.e., compounds of formula V-b, wherein $R_5$ is OH, amino, mono or dialkylamino, or $C_1$-$C_6$ haloalkoxy.

In yet another aspect, the invention provides compounds of formula V-h, i.e., compounds of formula V-g, wherein $R_5$ is amino, or mono or di($C_1$-$C_6$ alkyl)amino.

In yet still another aspect, the invention provides compounds of formula V-i, i.e., compounds of formula V-b, wherein $R_5$ is $C_1$-$C_6$ haloalkoxy optionally substituted with 1 OH.

In yet another aspect, the invention provides compounds of formula V-j, i.e., compounds of formula V-i, wherein $R_5$ is —$CH_2$C(halogen)$_2$C(halogen)$_3$, —$CH_2CH_2$C(halogen)$_3$, where each halogen is independently F or Cl.

In still another aspect, the invention provides compounds of formula V-k, i.e., compounds of formula V-j, wherein $R_5$ is —$CH_2CF_2CF_3$, —$CH_2CH_2CF_3$.

In another aspect, the invention provides compounds of formula V-l, i.e., compounds of formula V-i, wherein $R_5$ is —$CH(CH_3)$C(halogen)$_2$C(halogen)$_3$, —$CH(CH_2$halogen)$_2$, —$CH(CH_3)$C(halogen)$_3$, —$CH(C(halogen)_3)_2$, —$C(CH_3)(C$(halogen)$_3)_2$, or —$CH(OH)$C(halogen)$_3$, where each halogen is independently F or Cl.

In yet another aspect, the invention provides compounds of formula V-ll, i.e., compounds of formula V-i, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula V-m, i.e., compounds of formula V-l, wherein $R_5$ is —$C(CH_3)(C$(halogen)$_3)_2$ preferably each halogen is F.

In still yet another aspect, the invention provides compounds of formula V-n, i.e., compounds of formula V-l, wherein $R_5$ is —$CH(OH)$C(halogen)$_3$. In one case, the stereogenic center in $R_5$ has the S-configuration. In another case, the stereogenic center in $R_5$ has the R-configuration.

In another aspect, the invention provides compounds of formula V-o, i.e., compounds according to any one of formulas V-a, V-b, V-c, V-d, V-e, V-f, V-g, V-h, V-l, V-j, V-k, V-l, V-ll, V-m, or V-n, wherein at least one of $R_{30}$ and $R_{40}$ is H; and $R_{80}$ is H, Cl, or $OCF_3$.

In still yet another aspect, the invention provides compounds of formula V-p, i.e., compounds of formula V-o, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula V-q, i.e., compounds of formula V-o, wherein both $R_{30}$ and $R_{40}$ are H.

In yet another aspect, the invention provides compounds of formula V-q1, i.e., compounds according to any one of formulas V-o, V-p, or V-q wherein n is 1.

In yet still another aspect, the invention provides compounds of formula V-q2, i.e., compounds of formula V-q1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-q3, i.e., compounds of formula V-q2, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-q4, i.e., compounds of formula V-q3, wherein $R_3$ is halogen.

In yet another aspect, the invention provides compounds of formula V-q5, i.e., compounds of formula V-q3, wherein $R_3$ is OH, $C_1$-$C_4$ alkyl, or $C_1$-$C_4$ alkoxy.

In yet still another aspect, the invention provides compounds of formula V-q6, i.e., compounds of formula V-q3, wherein $R_3$ is $CF_3$ or $OCF_3$.

In still another aspect, the invention provides compounds of formula V-q7, i.e., compounds according to any one of formulas V-o, V-p, or V-q wherein n is 0.

In another aspect, the invention provides compounds of formula V-q8, i.e., compound according to formula V-a, wherein $R_{20}$ is —($C_0$-$C_6$ alkyl)-O—$R_6$.

In yet still another aspect, the invention provides compounds of formula V-q9, i.e., compounds of formula V-q8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula V-q10, i.e., compound according to formula V-q9, wherein $R_{20}$ is —($C_0$-$C_6$ alkyl)-O—$R_6$.

In still yet another aspect, the invention provides compounds of formula V-q11, i.e., compound according to formula V-q10, wherein $R_{20}$ is —($C_0$-$C_4$ alkyl)-O—$R_6$.

In another aspect, the invention provides compounds of formula V-q12, i.e., compounds according to any one of formulas V-q8, V-q9, V-q10, or V-q11, wherein at least one of $R_{30}$ and $R_{40}$ is H; and $R_{50}$ is H, Cl, or $OCF_3$.

In still yet another aspect, the invention provides compounds of formula V-q13, i.e., compounds of formula V-q12, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula V-q14, i.e., compounds of formula V-q12, wherein both $R_{30}$ and $R_{40}$ are H.

In yet another aspect, the invention provides compounds of formula V-q15, i.e., compounds according to any one of formulas V-q8, V-q9, V-q10, V-q11, V-q12, V-q13, or V-q14 wherein n is 1.

In yet still another aspect, the invention provides compounds of formula V-q16, i.e., compounds of formula V-q15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-q17, i.e., compounds of formula V-q16, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-q18, i.e., compounds of formula V-q17, wherein $R_3$ is halogen.

In yet another aspect, the invention provides compounds of formula V-q19, i.e., compounds of formula V-q17, wherein $R_3$ is OH, $C_1$-$C_4$ alkyl, or $C_1$-$C_4$ alkoxy.

In yet still another aspect, the invention provides compounds of formula V-q20, i.e., compounds of formula V-q17, wherein $R_3$ is $CF_3$ or $OCF_3$.

In still another aspect, the invention provides compounds of formula V-q21, i.e., compounds according to any one of formulas V-q8, V-q9, V-q10, V-q11, V-q12, V-q13, or V-q14 wherein n is 0.

In another aspect, the invention provides compounds of formula V-r, i.e., compounds of formula V, wherein $R_1$ is $CH_2COOH$.

In still another aspect, the invention provides compounds of formula V-s, i.e., compounds of formula V-r, wherein $R_{20}$ is —($C_0$-$C_6$ alkyl)-$COR_5$.

In yet another aspect, the invention provides compounds of formula V-t, i.e., compounds of formula V-s, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula V-u, i.e., compounds of formula V-t, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula V-v, i.e., compounds of formula V-t, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula V-w, i.e., compounds of formula V-t, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula V-x, i.e., compounds of formula V-s, wherein $R_5$ is OH, amino, mono or dialkylamino, or $C_1$-$C_6$ haloalkoxy.

In yet another aspect, the invention provides compounds of formula V-y, i.e., compounds of formula V-x, wherein $R_5$ is amino, or mono or di($C_1$-$C_6$ alkyl)amino.

In yet still another aspect, the invention provides compounds of formula V-z, i.e., compounds of formula V-s, wherein $R_5$ is $C_1$-$C_6$ haloalkoxy optionally substituted with 1 OH.

In yet another aspect, the invention provides compounds of formula V-aa, i.e., compounds of formula V-z, wherein $R_5$ is —$CH_2C$(halogen)$_2C$(halogen)$_3$, —$CH_2CH_2C$(halogen)$_3$, where each halogen is independently F or Cl.

In still another aspect, the invention provides compounds of formula V-bb, i.e., compounds of formula V-aa, wherein $R_5$ is —$CH_2CF_2CF_3$, —$CH_2CH_2CF_3$.

In another aspect, the invention provides compounds of formula V-cc, i.e., compounds of formula V-z, wherein $R_5$ is —$CH(CH_3)C$(halogen)$_2C$(halogen)$_3$, —$CH(CH_2$halogen)$_2$, —$CH(CH_3)C$(halogen)$_3$, —$CH(C$(halogen)$_3)_2$, —$C(CH_3)(C$(halogen)$_3)_2$, or —$CH(OH)C$(halogen)$_3$, where each halogen is independently F or Cl.

In yet another aspect, the invention provides compounds of formula V-dd, i.e., compounds of formula V-cc, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula V-ee, i.e., compounds of formula V-cc wherein $R_5$ is —$C(CH_3)(C$(halogen)$_3)_2$ preferably each halogen is F.

In still yet another aspect, the invention provides compounds of formula V-ff, i.e., compounds of formula V-cc, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula V-gg, i.e., compounds according to any one of formulas V-r, V-s, V-t, V-u, V-v, V-w, V-x, V-y, V-z, V-aa, V-bb, V-cc, V-dd, V-ee, or V-ff, wherein at least one of $R_{30}$ and $R_{40}$ is H; and $R_{80}$ is H, Cl, or $OCF_3$.

In still yet another aspect, the invention provides compounds of formula V-hh, i.e., compounds of formula V-gg, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula V-ii, i.e., compounds of formula V-gg, wherein both $R_{30}$ and $R_{40}$ are H.

In yet another aspect, the invention provides compounds of formula V-ii1, i.e., compounds according to any one of formulas V-gg, V-hh, or V-ii wherein n is 1.

In yet still another aspect, the invention provides compounds of formula V-ii2, i.e., compounds of formula V-ii1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-ii3, i.e., compounds of formula V-ii2, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-ii4, i.e., compounds of formula V-ii3, wherein $R_3$ is halogen.

In yet another aspect, the invention provides compounds of formula V-ii5, i.e., compounds of formula V-ii2, wherein $R_3$ is OH, $C_1$-$C_4$ alkyl, or $C_1$-$C_4$ alkoxy.

In yet still another aspect, the invention provides compounds of formula V-ii6, i.e., compounds of formula V-ii2, wherein $R_3$ is $CF_3$ or $OCF_3$.

In still another aspect, the invention provides compounds of formula V-ii7, i.e., compounds according to any one of formulas V-gg, V-hh, or V-ii wherein n is 0.

In another aspect, the invention provides compounds of formula V-ii8, i.e., compound according to formula V, wherein $R_1$ is $CH_2CO_2H$ and $R_{20}$ is —($C_0$-$C_6$ alkyl)-O—$R_6$.

In yet still another aspect, the invention provides compounds of formula V-ii9, i.e., compounds of formula V-ii8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula V-ii10, i.e., compound according to formula V-ii9, wherein $R_{20}$ is —($C_0$-$C_6$ alkyl)-O—$R_6$.

In still yet another aspect, the invention provides compounds of formula V-ii11, i.e., compound according to formula V-ii10, wherein $R_{20}$ is —($C_0$-$C_4$ alkyl)-O—$R_6$.

In another aspect, the invention provides compounds of formula V-ii12, i.e., compounds according to any one of formulas V-ii8, V-ii9, V-ii10, or V-ii11, wherein at least one of $R_{30}$ and $R_{40}$ is H; and $R_{80}$ is H, Cl, or $OCF_3$.

In still yet another aspect, the invention provides compounds of formula V-ii13, i.e., compounds of formula V-ii12, wherein one of $R_{30}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula V-ii14, i.e., compounds of formula V-ii12, wherein both $R_{30}$ and $R_{40}$ are H.

In yet another aspect, the invention provides compounds of formula V-ii15, i.e., compounds according to any one of formulas V-ii8, V-ii9, V-ii10, V-ii11, V-ii12, V-ii13, or V-ii14 wherein n is 1.

In yet still another aspect, the invention provides compounds of formula V-ii16, i.e., compounds of formula V-ii15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-ii17, i.e., compounds of formula V-ii16, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-ii18, i.e., compounds of formula V-ii17, wherein $R_3$ is halogen.

In yet another aspect, the invention provides compounds of formula V-ii19, i.e., compounds of formula V-ii17, wherein $R_3$ is OH, $C_1$-$C_4$ alkyl, or $C_1$-$C_4$ alkoxy.

In yet still another aspect, the invention provides compounds of formula V-ii20, i.e., compounds of formula V-ii17, wherein $R_3$ is $CF_3$ or $OCF_3$.

In still another aspect, the invention provides compounds of formula V-ii21, i.e., compounds according to any one of formulas V-ii8, V-ii9, V-ii10, V-ii11, V-ii12, V-ii13, or V-ii14 wherein n is 0.

In another aspect, the invention provides compounds of formula V-jj, i.e., compounds of formula V, wherein $R_1$ is H and $R_{30}$ is —($C_0$-$C_6$ alkyl)-$COR_5$.

In yet another aspect, the invention provides compounds of formula V-kk, i.e., compounds of formula V-jj, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula V-ll, i.e., compounds of formula V-kk, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula V-mm, i.e., compounds of formula V-kk, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula V-nn, i.e., compounds of formula V-kk, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula V-oo, i.e., compounds of formula V-jj, wherein $R_5$ is OH, amino, mono or dialkylamino, or $C_1$-$C_6$ haloalkoxy.

In yet another aspect, the invention provides compounds of formula V-pp, i.e., compounds of formula V-oo, wherein $R_5$ is amino, or mono or di($C_1$-$C_6$ alkyl)amino.

In yet still another aspect, the invention provides compounds of formula V-qq, i.e., compounds of formula V-jj, wherein $R_5$ is $C_1$-$C_6$ haloalkoxy optionally substituted with 1 OH.

In yet another aspect, the invention provides compounds of formula V-rr, i.e., compounds of formula V-qq, wherein $R_5$ is —$CH_2C$(halogen)$_2C$(halogen)$_3$, —$CH_2CH_2C$(halogen)$_3$, where each halogen is independently F or Cl.

In still another aspect, the invention provides compounds of formula V-ss, i.e., compounds of formula V-rr, wherein $R_5$ is —$CH_2CF_2CF_3$, —$CH_2CH_2CF_3$.

In another aspect, the invention provides compounds of formula V-tt, i.e., compounds of formula V-qq, wherein $R_5$ is —$CH(CH_3)C$(halogen)$_2C$(halogen)$_3$, —$CH(CH_2$halogen)$_2$, —$CH(CH_3)C$(halogen)$_3$, —$CH(C$(halogen)$_3)_2$, —$C(CH_3)(C$(halogen)$_3)_2$, or —$CH(OH)C$(halogen)$_3$, where each halogen is independently F or Cl.

In yet another aspect, the invention provides compounds of formula V-uu, i.e., compounds of formula V-tt, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula V-vv, i.e., compounds of formula V-tt, wherein $R_5$ is —$C(CH_3)(C$(halogen)$_3)_2$ preferably each halogen is F.

In still yet another aspect, the invention provides compounds of formula V-ww, i.e., compounds of formula V-tt, wherein $R_5$ is —$CH(OH)C$(halogen)$_3$. In one case, the stereogenic center in $R_5$ has the S-configuration. In another case, the stereogenic center in $R_5$ has the R-configuration.

In another aspect, the invention provides compounds of formula V-xx, i.e., compounds according to any one of formulas V-jj, V-kk, V-ll, V-mm, V-nn, V-oo, V-pp, V-qq, V-rr, V-ss, V-tt, V-uu, V-vv, or V-ww, wherein at least one of $R_{20}$ and $R_{40}$ is H; and $R_{80}$ is H, Cl, or $OCF_3$.

In still yet another aspect, the invention provides compounds of formula V-yy, i.e., compounds of formula V-xx, wherein one of $R_{20}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula V-zz, i.e., compounds of formula V-xx, wherein both $R_{20}$ and $R_{40}$ are H.

In yet another aspect, the invention provides compounds of formula V-zz1, i.e., compounds according to any one of formulas V-xx, V-yy, or V-zz wherein n is 1.

In yet still another aspect, the invention provides compounds of formula V-zz2, i.e., compounds of formula V-zz1, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-zz3, i.e., compounds of formula V-zz2, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-zz4, i.e., compounds of formula V-zz3, wherein $R_3$ is halogen.

In yet another aspect, the invention provides compounds of formula V-zz5, i.e., compounds of formula V-zz3, wherein $R_3$ is OH, $C_1$-$C_4$ alkyl, or $C_1$-$C_4$ alkoxy.

In yet still another aspect, the invention provides compounds of formula V-zz6, i.e., compounds of formula V-zz3, wherein $R_3$ is $CF_3$ or $OCF_3$.

In still another aspect, the invention provides compounds of formula V-zz7, i.e., compounds according to any one of formulas V-xx, V-yy, or V-zz wherein n is 0.

In another aspect, the invention provides compounds of formula V-zz8, i.e., compound according to formula V, wherein $R_1$ is H and $R_{30}$ is —($C_0$-$C_6$ alkyl)-O—$R_6$.

In yet still another aspect, the invention provides compounds of formula V-zz9, i.e., compounds of formula V-zz8, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula V-zz10, i.e., compound according to formula V-zz9, wherein $R_{30}$ is —($C_0$-$C_6$ alkyl)-O—$R_6$.

In still yet another aspect, the invention provides compounds of formula V-zz10, i.e., compound according to formula V-zz10, wherein $R_{30}$ is —($C_0$-$C_4$ alkyl)-O—$R_6$.

In another aspect, the invention provides compounds of formula V-zz12, i.e., compounds according to any one of formulas V-zz8, V-zz9, V-zz10, or V-zz11, wherein at least one of $R_{20}$ and $R_{40}$ is H; and $R_{80}$ is H, Cl, or $OCF_3$.

In still yet another aspect, the invention provides compounds of formula V-zz13, i.e., compounds of formula V-zz12, wherein one of $R_{20}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula V-zz14, i.e., compounds of formula V-zz12, wherein both $R_{20}$ and $R_{40}$ are H.

In yet another aspect, the invention provides compounds of formula V-zz15, i.e., compounds according to any one of formulas V-zz8, V-zz9, V-z10, V-zz11, V-zz12, V-zz13, or V-zz14 wherein n is 1.

In yet still another aspect, the invention provides compounds of formula V-zz16, i.e., compounds of formula V-zz15, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-zz17, i.e., compounds of formula V-zz16, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-zz18, i.e., compounds of formula V-zz17, wherein $R_3$ is halogen.

In yet another aspect, the invention provides compounds of formula V-zz19, i.e., compounds of formula V-zz17, wherein $R_3$ is OH, $C_1$-$C_4$ alkyl, or $C_1$-$C_4$ alkoxy.

In yet still another aspect, the invention provides compounds of formula V-zz20, i.e., compounds of formula V-zz17, wherein $R_3$ is $CF_3$ or $OCF_3$.

In still another aspect, the invention provides compounds of formula V-zz21, i.e., compounds according to any one of formulas V-zz8, V-zz9, V-zz10, V-zz11, V-zz12, V-zz13, or V-zz14 wherein n is 0.

In another aspect, the invention provides compounds of formula V-aaa, i.e., compounds of formula V, wherein $R_1$ is $CH_2COOH$ and $R_{30}$ is —($C_0$-$C_6$ alkyl)-$COR_5$.

In yet another aspect, the invention provides compounds of formula V-bbb, i.e., compounds of formula V-aaa, wherein $R_5$ is $C_1$-$C_6$ alkoxy optionally substituted with 1 or 2 groups that are independently OH, $C_1$-$C_4$ alkoxy, piperidinyl, pyrrolidinyl, morpholinyl, piperazinyl, $C_3$-$C_7$ cycloalkyl, —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still yet another aspect, the invention provides compounds of formula V-ccc, i.e., compounds of formula V-bbb, wherein $R_5$ is $C_1$-$C_6$ alkoxy optionally substituted with 1 group that is piperidinyl, pyrrolidinyl, morpholinyl, or piperazinyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In still another aspect, the invention provides compounds of formula V-ddd, i.e., compounds of formula V-bbb, wherein $R_5$ is $C_1$-$C_6$ alkoxy optionally substituted with 1 group that is —$SO_2$—($C_1$-$C_4$ alkyl), —$SO_2$—($C_1$-$C_4$ haloalkyl), or —$SO_2$-phenyl wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino.

In another aspect, the invention provides compounds of formula V-eee, i.e., compounds of formula V-bbb, wherein $R_5$ is $C_1$-$C_6$ alkoxy optionally substituted with $C_3$-$C_7$ cycloalkyl (preferably $C_3$-$C_6$ cycloalkyl, more preferably $C_3$-$C_5$ cycloalkyl, still more preferably, cyclopropyl) wherein the cyclic portions of the above are optionally substituted at a substitutable position with groups that are independently $C_1$-$C_4$ alkyl, $C_1$-$C_4$ alkoxy, halogen, OH, $C_1$-$C_4$ haloalkyl, $C_1$-$C_4$ haloalkoxy, amino, or mono or dialkylamino In still another aspect, the invention provides compounds of formula V-fff, i.e., compounds of formula V-aaa, wherein $R_5$ is OH, amino, mono or dialkylamino, or $C_1$-$C_6$ haloalkoxy.

In yet another aspect, the invention provides compounds of formula V-ggg, i.e., compounds of formula V-fff, wherein $R_5$ is amino, or mono or di($C_1$-$C_6$ alkyl)amino.

In yet still another aspect, the invention provides compounds of formula V-hhh, i.e., compounds of formula V-aaa, wherein $R_5$ is $C_1$-$C_6$ haloalkoxy optionally substituted with 1 OH.

In yet another aspect, the invention provides compounds of formula V-iii, i.e., compounds of formula V-hhh, wherein $R_5$ is —$CH_2C(halogen)_2C(halogen)_3$, —$CH_2CH_2C(halogen)_3$, where each halogen is independently F or Cl.

In still another aspect, the invention provides compounds of formula V-jjj, i.e., compounds of formula V-iii, wherein $R_5$ is —$CH_2CF_2CF_3$, —$CH_2CH_2CF_3$.

In another aspect, the invention provides compounds of formula V-kkk, i.e., compounds of formula V-hhh, wherein $R_5$ is —$CH(CH_3)C(halogen)_2C(halogen)_3$, —$CH(CH_2$ halogen$)_2$, —$CH(CH_3)C(halogen)_3$, —$CH(C(halogen)_3)_2$, —$C(CH_3)(C(halogen)_3)_2$, or —$CH(OH)C(halogen)_3$, where each halogen is independently F or Cl.

In yet another aspect, the invention provides compounds of formula V-lll, i.e., compounds of formula V-kk, wherein $R_5$ is —$CH(CH_3)CF_2CF_3$, —$CH(CH_2F)_2$, —$CH(CH_3)CF_3$, —$CH(CF_3)_2$, —$C(CH_3)(CF_3)_2$, or —$CH(OH)CF_3$.

In still another aspect, the invention provides compounds of formula V-mmm, i.e., compounds of formula V-kkk wherein $R_5$ is —$C(CH_3)(C(halogen)_3)_2$ preferably each halogen is F.

In still yet another aspect, the invention provides compounds of formula V-nnn, i.e., compounds of formula V-kkk, wherein $R_5$ is —$CH(OH)C(halogen)_3$. In one case, the stereogenic center in $R_5$ has the S-configuration. In another case, the stereogenic center in $R_5$ has the R-configuration.

In another aspect, the invention provides compounds of formula V-ooo, i.e., compounds according to any one of formulas V-aaa, V-bbb, V-ccc, V-ddd, V-eee, V-fff, V-ggg, V-hhh, V-iii, V-jjj, V-kkk, V-lll, V-mmm, or V-nnn, wherein at least one of $R_{20}$ and $R_{40}$ is H; and $R_{80}$ is H, Cl, or $OCF_3$.

In still yet another aspect, the invention provides compounds of formula V-ppp, i.e., compounds of formula V-ooo, wherein one of $R_{20}$ and $R_{40}$ is halogen (in one aspect, F or Cl), OH, amino, mono or di($C_1$-$C_4$)alkylamino, hydroxy($C_1$-$C_4$) alkyl, $CF_3$, or $OCF_3$.

In yet still another aspect, the invention provides compounds of formula V-qqq, i.e., compounds of formula V-ooo, wherein both $R_{20}$ and $R_{40}$ are H.

In yet another aspect, the invention provides compounds of formula V-rrr, i.e., compounds according to any one of formulas V-ooo, V-ppp, or V-qqq wherein n is 1.

In yet still another aspect, the invention provides compounds of formula V-sss, i.e., compounds of formula V-rrr, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-ttt, i.e., compounds of formula V-sss, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-uuu, i.e., compounds of formula V-ttt, wherein $R_3$ is halogen.

In yet another aspect, the invention provides compounds of formula V-vvv, i.e., compounds of formula V-ttt, wherein $R_3$ is OH, $C_1$-$C_4$ alkyl, or $C_1$-$C_4$ alkoxy.

In yet still another aspect, the invention provides compounds of formula V-www, i.e., compounds of formula V-ttt, wherein $R_3$ is $CF_3$ or $OCF_3$.

In still another aspect, the invention provides compounds of formula V-xxx, i.e., compounds according to any one of formulas V-ooo, V-ppp, or V-qqq wherein n is 0.

In another aspect, the invention provides compounds of formula V-xxx1, i.e., compound according to formula V, wherein $R_1$ is $CH_2CO_2H$ and $R_{30}$ is —($C_0$-$C_6$ alkyl)-O—$R_6$.

In yet still another aspect, the invention provides compounds of formula V-xxx2, i.e., compounds of formula V-xxx1, wherein $R_6$ is $C_1$-$C_6$ alkanoyl, wherein the alkyl portion of the alkanoyl group is substituted with one or more halogens (preferably F or Cl, more preferably, F.) Or $R_6$ can be —($C_1$-$C_4$ alkyl)-phenyl, —($C_1$-$C_4$ alkanoyl)-phenyl, or phenyl, wherein the phenyl groups are optionally substituted with 1, 2, 3, 4, or 5 groups that are independently $C_1$-$C_4$ alkyl, $C_1$-$C_4$ alkoxy, halogen, OH, $C_1$-$C_4$ haloalkyl (such as $CF_3$), $C_1$-$C_4$ haloalkoxy (such as $OCF_3$), amino, or mono or di $C_1$-$C_6$ alkylamino.

In still yet another aspect, the invention provides compounds of formula V-xxx3, i.e., compound according to formula V-xxx2, wherein $R_{30}$ is —($C_0$-$C_6$ alkyl)-O—$R_6$.

In still yet another aspect, the invention provides compounds of formula V-xxx4, i.e., compound according to formula V-xxx3, wherein $R_{30}$ is —($C_0$-$C_4$ alkyl)-O—$R_6$.

In another aspect, the invention provides compounds of formula V-xxx5, i.e., compounds according to any one of formulas V-xxx1, V-xxx2, V-xxx3, or V-xxx4, wherein at least one of $R_{20}$ and $R_{40}$ is H; and $R_{80}$ is H, Cl, or $OCF_3$.

In still yet another aspect, the invention provides compounds of formula V-xxx6, i.e., compounds of formula V-xxx5, wherein one of $R_{20}$ and $R_{40}$ is halogen (in one aspect, F or Cl), OH, amino, mono or di($C_1$-$C_4$)alkylamino, hydroxy ($C_1$-$C_4$)alkyl, $CF_3$, or $OCF_3$.

In yet still another aspect, the invention provides compounds of formula V-xxx7, i.e., compounds of formula V-xxx5, wherein both $R_{20}$ and $R_{40}$ are H.

In yet another aspect, the invention provides compounds of formula V-xxx8, i.e., compounds according to any one of formulas V-xxx1, V-xxx2, V-xxx3, V-xxx4, V-xxx5, V-xxx6, or V-xxx7, wherein n is 1.

In yet still another aspect, the invention provides compounds of formula V-xxx9, i.e., compounds of formula V-xxx8, wherein $R_3$ is halogen, OH, $C_1$-$C_4$ alkyl, $C_1$-$C_4$ alkoxy, $C_1$-$C_2$ haloalkyl, or $C_1$-$C_2$ haloalkoxy.

In still yet another aspect, the invention provides compounds of formula V-xxx10, i.e., compounds of formula V-xxx9, wherein $R_3$ is halogen, OH, $C_1$-$C_4$ alkyl, $C_1$-$C_4$ alkoxy, $CF_3$, or $OCF_3$.

In still another aspect, the invention provides compounds of formula V-xxx11, i.e., compounds of formula V-xxx10, wherein $R_3$ is halogen.

In yet another aspect, the invention provides compounds of formula V-xxx12, i.e., compounds of formula V-xxx10, wherein $R_3$ is OH, $C_1$-$C_4$ alkyl, or $C_1$-$C_4$ alkoxy.

In yet still another aspect, the invention provides compounds of formula V-xxx13, i.e., compounds of formula V-xxx10, wherein $R_3$ is $CF_3$ or $OCF_3$.

In still another aspect, the invention provides compounds of formula V-xxx10, i.e., compounds according to any one of formulas V-xxx1, V-xxx2, V-xxx3, V-xxx4, V-xxx5, V-xxx6, or V-xxx7 wherein n is 0.

In another aspect, the invention provides a compound according to any of the previously mentioned aspects of formulas I, II, III, IV, or V, wherein when $R_{20}$ is —($C_0$-$C_6$ alkyl)-$COR_5$, it is preferably —($C_0$-$C_4$ alkyl)-$COR_5$, more preferably —($C_0$-$C_2$ alkyl)-$COR_5$, and still more preferably —$COR_5$, where $R_5$ is as previously defined.

In another aspect, the invention provides a compound according to any of the previously mentioned aspects of formulas I, II, III, IV, or V, wherein when $R_{30}$ is —($C_0$-$C_6$ alkyl)-$COR_5$, it is preferably —($C_0$-$C_4$ alkyl)-$COR_5$, more preferably —(C₀-C₂ alkyl)-COR₅, and still more preferably —COR₅, where R₅ is as previously defined.

In another aspect, the invention provides compounds of formula VI, i.e, compounds of formula I, of the following structure.

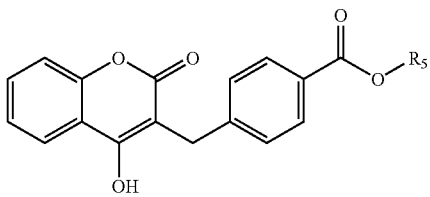

and pharmaceutically acceptable salts thereof, wherein R₅ is $C_1$-$C_8$ alkyl substituted with at least one halogen.

In still another aspect, the invention provides compounds of formula VI-a, i.e., compounds of formula VI, wherein R₅ is $C_2$-$C_8$ alkyl substituted with at least one halogen.

In still yet another aspect, the invention provides compounds of formula VI-b, i.e., compounds of formula VI-a, wherein R₅ is $C_3$-$C_7$ alkyl substituted with at least one halogen.

In yet still another aspect, the invention provides compounds of formula VI-c, i.e., compounds of formula VI-b, wherein R₅ is $C_3$-$C_6$ substituted with at least one halogen.

In still another aspect, the invention provides compounds of formula VI-d, i.e., compounds of formula VI-c, wherein R₅ is $C_3$-$C_6$ substituted with at least one fluoro group.

In yet another aspect, the invention provides compounds of formula VI-e, i.e., compounds of formula VI-d, wherein R₅ is R is $C_3$-$C_6$ substituted with at least two fluoro groups.

In still another aspect, the invention provides compounds of formula VI-f, i.e., compounds of formula VI-e, wherein R₅ is a tert-butyl group substituted with six fluoro groups.

In still another aspect, the invention provides compounds of formula VI-g, i.e., compounds of formula VI-f, wherein R₅ is

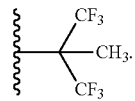

In still another aspect, the invention provides a compound of formula VI-h, i.e., a compound of formula VI, that is 1,1,1,3,3,3-hexafluoro-2-methylpropan-2-yl 4-((4-hydroxy-2-oxo-2H-chromen-3-yl)methyl)benzoate, or pharmaceutically acceptable salts thereof.

In still another aspect, the invention provides a compound of formula VI-i, i.e., a compound of formula VI, that is 1,1,1,3,3,3-hexafluoro-2-methylpropan-2-yl 4-((4-hydroxy-2-oxo-2H-chromen-3-yl)methyl)benzoate.

In still another aspect, the invention provides a compound of formula VI-j, i.e., a compound of formula VI-h, that is the sodium or potassium salt of 1,1,1,3,3,3-hexafluoro-2-methylpropan-2-yl 4-((4-hydroxy-2-oxo-2H-chromen-3-yl)methyl)benzoate.

In still another aspect, the invention provides a compound of formula VI-k, i.e., a compound of formula VI-j, that is the sodium salt.

Compounds where R₅ is H are the primary metabolites when compounds of Formulas I, II, III, IV, V, and/or VI are administered to a mammal, including humans. They are essentially devoid of activity at the VKER enzyme, but they are useful for monitoring drug levels in patients.

4-[(4-hydroxy-2-oxo-2H-chromen-3-yl)methyl]benzoic acid and the other acids (i.e., compounds where R₅ is H) disclosed herein are very useful for preparing the desired halogenated esters of the invention.

Specific embodiments of the present invention include the following compounds:

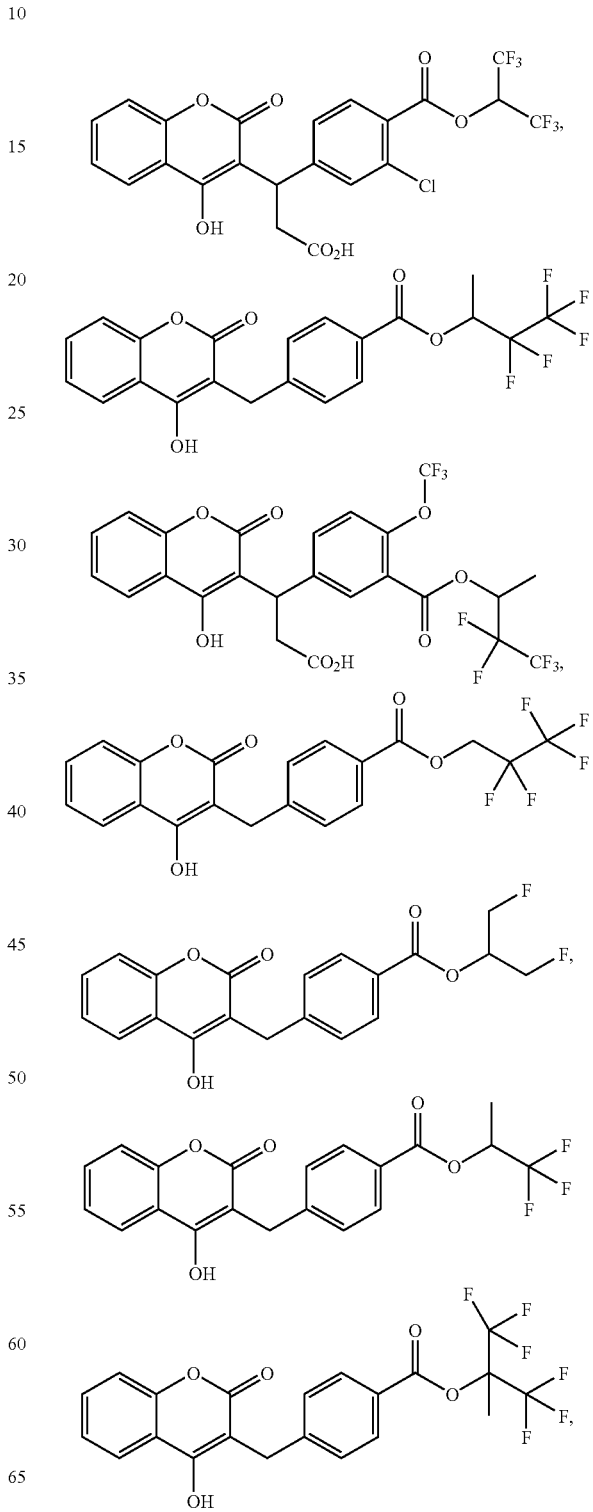

-continued

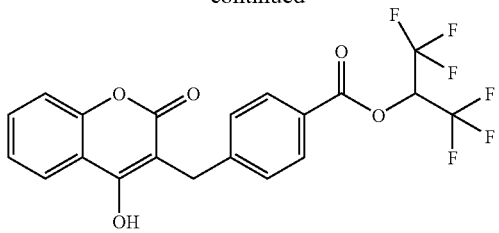

The term "alkoxy" represents an alkyl group attached to the parent molecular moiety through an oxygen bridge. Examples of alkoxy groups include, for example, methoxy, ethoxy, propoxy, isopropoxy, pentoxy, tert-butyloxy and hexyloxy.

By "alkyl" is meant a straight or branched, non-cyclic, hydrocarbon. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, heptyl and octyl. "$C_1$-$C_6$ alkyl" denotes straight or branched, non-cyclic, alkyl groups having 1-6 carbon atoms. Likewise, "$C_1$-$C_4$ alkyl" denotes straight or branched, non-cyclic, alkyl groups having 1-4 carbon atoms.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl.

The terms "halogen" or "halo" indicate fluorine, chlorine, bromine, and iodine.

The term "heterocycloalkyl" refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl. More preferred heterocycloalkyl groups include piperidinyl, pyrrolidinyl, morpholinyl and piperazinyl.

The subject invention provides materials and methods for anticoagulant treatment. Advantageously, the therapeutic compounds of the subject invention are stable in storage but have a shorter half-life in the physiological environment than other drugs that are available for anticoagulant treatment; therefore, the compounds of the subject invention can be used with a lower incidence of side effects and toxicity. In a preferred embodiment, the subject invention provides therapeutic anticoagulant compounds. The compounds of the subject invention can be used to treat at-risk populations thereby bringing relief of symptoms, improving the quality of life, preventing acute and long-term complications, reducing mortality and treating accompanying disorders.

Advantageously, the subject invention provides compounds that are readily metabolized by the physiological metabolic drug detoxification systems. Specifically, in a preferred embodiment, the therapeutic compounds of the subject invention contain a halogenated ester group, which does not detract from the ability of these compounds to provide a therapeutic benefit, but which makes these compounds more susceptible to degradation by hydrolases, particularly serum and/or cytosolic esterases. Advantageously, the compounds have been found to inhibit the vitamin K epoxide reductase (VKER) enzyme.

In addition to their activity at the VKER enzyme, the presence of at least one halogen atom in the ester moiety gives these compounds certain advantageous properties. Specifically, the addition of halogen to these compounds greatly reduces or eliminates their metabolism by CYP450, while at the same time greatly increasing esterase mediated hydrolysis. Thus, halogenation unexpectedly confers a predilection for esterase metabolism when in the absence of such halogenation there is a predilection for CYP450 metabolism. This property gives the halogenated ester compounds important therapeutic advantages over non-halogenated analogs.

Because the halogenated compounds of the subject invention do not depend on CYP450 enzymes for metabolism, they are not likely to interact with other drugs at the CYP450 site and therefore they are safe to use in patients who are already taking other medications, unlike their non-halogenated analogs. The subject invention further provides methods of treatment comprising the administration of these compounds to individuals in need of anticoagulant treatment.

In a further embodiment, the subject invention pertains to breakdown products that are formed when the therapeutic compounds of the subject invention are acted upon by esterases. These breakdown products can be used, for example, as described herein to monitor the clearance of the therapeutic compounds from a patient.

In yet a further embodiment, the subject invention provides methods for synthesizing the compounds of the subject invention.

The subject invention provides materials and methods for the treatment of coagulation disorders. Specifically, the subject invention provides compounds which are readily metabolized by the hydrolytic drug detoxification systems preferentially to the oxidative drug detoxification system. Specifically, this invention provides compounds that are susceptible to degradation by hydrolases, particularly serum and/or cytosolic esterases. This invention is also drawn to methods of treating coagulation disorders.

This invention is drawn to compounds which are more easily metabolized by the hydrolytic drug detoxification systems. This invention is also drawn to methods of treating coagulation disorders. Specifically, this invention provides analogs of drugs which have been designed to be more susceptible to degradation by hydrolases, particularly serum and/or cytosolic esterases and methods of treatment comprising the administration of these analogs to individuals.

Advantageously, use of the compounds of the subject invention can results in a reduction of clinically relevant metabolic interactions involving the CYP system (particularly the CYP3A4 fraction) and helps to avoid ADRs. These compounds do not rely on the CYP450 enzyme system, but instead, exploit widely distributed esterases for metabolism and generation of a metabolite that is substantially pharmacologically inactive. This approach makes anticoagulant agents safer while maintaining efficacy, and also significantly reduces the financial risk of drug development.

In a preferred embodiment of the subject invention, therapeutic compounds are provided which are useful in providing anticoagulant treatment and which contain a halogenated ester group that is acted upon by hydrolytic enzymes, thereby breaking down the compound to a substantially inactive and water soluble metabolite and facilitating its efficient removal from the treated individual. As referred to herein, a "substantially inactive" metabolite may exhibit, e.g., less than or equal to about 10% (and more preferably less than or equal to about 5%; even more preferably less than or equal to about 2%; and most preferably less than or equal to about 1%) of the parent compound's activity. In a preferred embodiment the therapeutic compounds are metabolized by plasma esterases, tissue esterases, and/or non-oxidative/hydrolytic microsomal esterases.

A further aspect of the subject invention pertains to the breakdown products that are produced when the therapeutic compounds of the subject invention are acted upon by esterases. The presence of these breakdown products in the urine or serum can be used to monitor the rate of clearance of the therapeutic compound from a patient.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site that is convenient in the manufacturing process for the target drug. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The subject invention further provides anticoagulant treatment comprising the administration of a therapeutically effective amount of halogenated ester compounds to an individual in need of treatment. Accordingly, the subject invention provides halogenated esters and pharmaceutical compositions of these ester compounds. In a preferred embodiment the patient is a human; however, non-human animals also can be treated.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent, metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is desirable and necessary in order to provide an escape metabolic route in case the primary route is blocked, in the case of VKER inhibitors such as the disclosed compounds of the subject invention, it is very important that the primary metabolism route be non-oxidative, because oxidative metabolism is especially sensitive to drug-drug interactions. The halogenated esters of this invention are primarily, if not only, metabolized by esterases, a non-oxidative enzymatic system, and therefore are especially useful to treat patients who are taking other medications.

Additional modifications of the compounds disclosed herein can readily be made by those skilled in the art. Thus, analogs and salts of the exemplified compounds are within the scope of the subject invention. With a knowledge of the compounds of the subject invention, skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acylation, halogenation and acidification reactions. For example, new salts within the scope of the invention can be made by adding mineral bases, e.g., NaOH, etc., or strong organic bases, e.g., triethanolamine, etc., in appropriate amounts to form the salt of the parent compound or its derivative. Also, synthesis type reactions may be used pursuant to known procedures to add or modify various groups in the exemplified compounds to produce other compounds within the scope of the invention.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The present invention also encompasses prodrugs of the compounds of Formula I.

In a preferred embodiment, the subject invention provides compounds having Formula II:

Advantageously, the halogenated compounds are less favorable substrates for cytochrome CYP450 than their non-halogenated analogs. They are therefore more likely to be metabolized by esterases, which is desirable for eliminating drug-drug interactions according to the subject invention.

The subject invention also provides processes for the manufacturing of the novel compounds. The synthesis of these compounds can be achieved as shown in schemes 1 and 2.

Scheme 1:

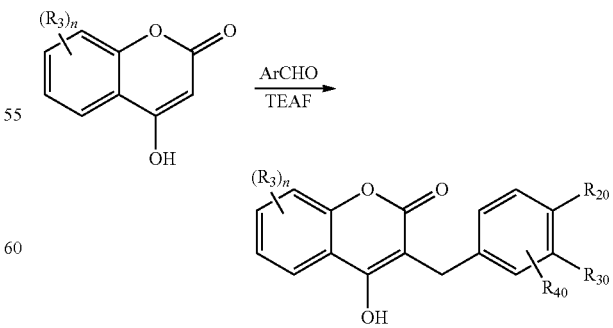

In scheme 1, optionally substituted 4-hydroxycoumarin and an optionally substituted aromatic aldehyde are heated in a mixture of triethylamine and formic acid (2:5 molar ratio) to give the correspondingly substituted 3-benzyl-4-hydroxy-coumarin wherein $R_1$ is hydrogen and n, $R_3$, $R_{20}$, $R_{30}$, and $R_{40}$ are defined as above.

Scheme 2:

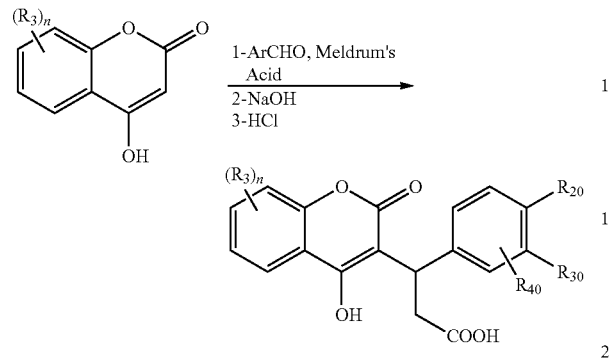

Scheme 2 describes a synthetic pathway for preparing compounds where $R_1$ is $CH_2COOH$. In scheme an optionally substituted 2,4-hydroxycoumarin, an optionally substituted aromatic aldehyde, and Meldrum's acid are heated in ethanol in the presence of ammonium acetate to give the correspondingly substituted chromen-3-yl-propionate, which in turn can be hydrolyzed using a base, such as NaOH, followed by acidification in order to provide the chromen-3-yl-propionic acid where n, $R_3$, $R_{20}$, $R_{30}$, and $R_{40}$ are defined as above.

Scheme 3

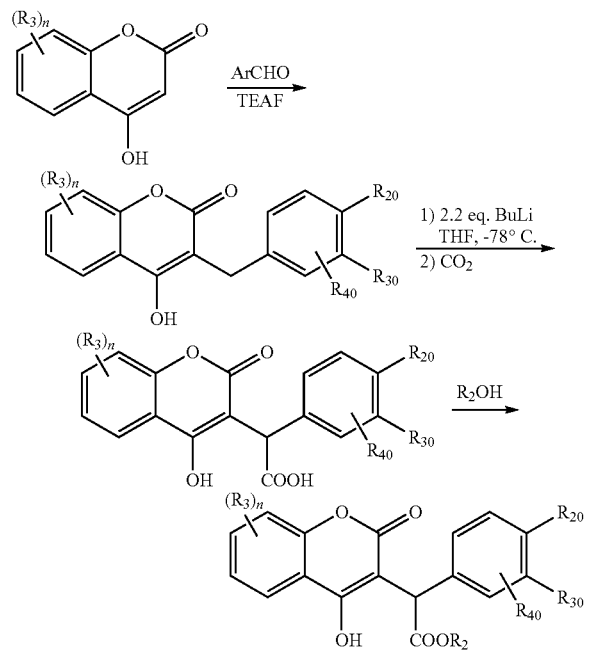

Scheme 3 provides an alternative synthesis of C-3 substituted 4-hydroxycoumarins. An optionally substituted 4-hydroxycoumarin and an aromatic aldehyde can be heated in a mixture of triethylamine and formic acid (2:5 molar ratio) to give an optionally substituted 3-benzyl-4-hydroxycoumarin, which was in turn treated with 2.2 eq. of a strong base, such as BuLi, and quenched with carbon dioxide to give an optionally substituted coumarin substituted phenyl-acetic acid. Corresponding esters can be obtained by treating the acid with various alcohols in the presence of an acid, such as concentrated sulfuric acid. n, $R_2$, $R_3$, $R_{20}$, $R_{30}$, and $R_{40}$ are defined as above.

Scheme 4

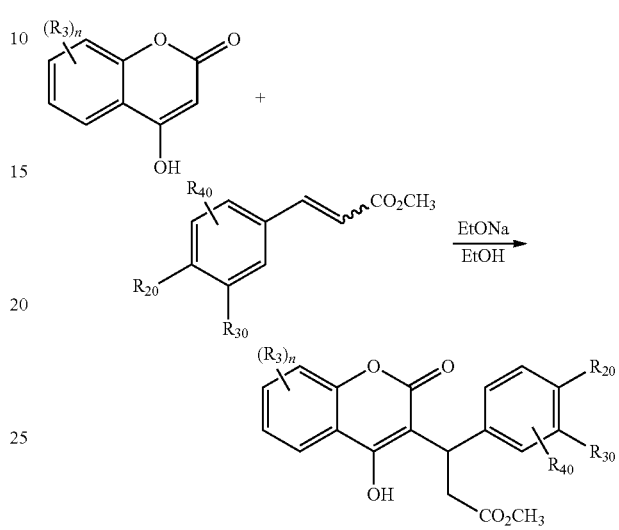

Scheme 4 illustrates an alternate method for preparing the compounds of the invention. An optionally substituted 4-hydroxycoumarin undergoes Michael addition with an optionally substituted methyl trans-cinnamate in an absolute alcohol, such as ethanol, in the presence of a base, such as sodium ethoxide, at reflux temperature for approximately 16 hours. One of ordinary skill in the art will appreciate that other cinnamate esters can be used and that n, $R_3$, $R_{20}$, $R_{30}$, and $R_{40}$ are as defined as above.

The subject invention further pertains to enantiomerically enriched compounds, and compositions comprising the compounds, for the treatment of coagulation disorders. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

The subject invention also provides methods for treating coagulation disorders comprising the administration of a therapeutically effective amount of the halogenated esters of this invention to an individual in need of treatment. The therapeutic compounds of this invention have applicability in both veterinary and human clinical contexts. Further, the compounds of this invention have therapeutic properties similar to those of the unmodified parent compound (COUMADIN). Accordingly, dosage rates and routes of administration of the disclosed compounds are similar to those already used in the art and known to the skilled artisan (see, for example, *Physicians' Desk Reference*, 54th Ed., Medical Economics Company, Montvale, N.J., 2000 or U.S. Pat. No. 5,856,525 hereby incorporated by reference in its entirety).

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with at least one suitable carrier, solvent, excipient, and/or adjuvant in order to facilitate effective administration of the composition.

In accordance with the invention, pharmaceutical compositions comprising, as an active ingredient, an effective amount of one or more of the compounds of the invention and one or more non-toxic, pharmaceutically acceptable carrier(s) and/or diluent(s). Examples of such carriers for use in the invention include ethanol, dimethylsulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The term "individual(s)" is defined as a single mammal to which is administered a compound of the present invention. The mammal may be a rodent, for example a mouse or a rat, or a non-rodent, for example a pig, a horse, a rabbit, a goat, a cow, a cat, a dog, or can be a human. In a preferred embodiment, the individual is a human.

Following are examples which illustrate procedures for practicing the invention. These examples should not be construed as limiting. All percentages are by weight and all solvent mixture proportions are by volume unless otherwise noted. Reactions were performed in dry solvents under an atmosphere of nitrogen unless otherwise specified, and were followed by thin-layer chromatography (TLC) on Analtech (0.25 mm) glass-packed precoated silica gel plates which were visualized by short wave UV light or in an iodine chamber. The term "standard work-up" refers to addition of water to the reaction mixture, extraction with EtOAc (3×), washing the combined organic layers successively with water and brine, drying over anhydrous $Na_2SO_4$, filtering and concentrating on a Buchi R-114 rotary evaporator. Chromatographic separations were performed on silica gel columns (Aldrich Silica Gel 70-230 mesh, 60 A) or on a Gilson liquid handler using a reverse phase Polaris C18 column (5μ, 100×212). $^1$H NMR spectra were recorded on a Nicolet/GE NT 300 spectrometer.

Example 1

Preparation of 4-(4-Hydroxy-2-oxo-2H-chromen-3-ylmethyl)-benzoic acid 2,2,2-trifluoro-1-methyl-1-trifluoromethyl-ethyl ester

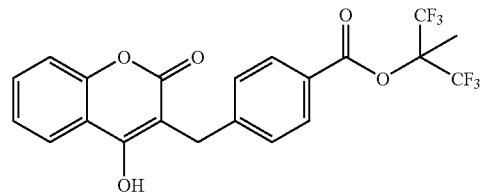

Triethylammonium formate (TEAF) is prepared by adding TEA (20.0 mL) to formic acid (16.5 mL) with ice cooling. To TEAF is added 4-(2,2,2-trifluoro-1-methyl-1-trifluoromethyl-ethoxycarbonyl)benzaldehyde (3.78 mL) and 4-hydroxy-chromen-2-one (6.0 g) and the resulting mixture heated to 130-140° C. for 3 hours, cooled to room temperature, diluted with water, and extracted with EtOAc.

The organic layer is washed with brine, dried over MgSO4 and conc. in vacuo to give a light yellow solid. The crude solid is recrystallized from EtOH to give 4-(4-Hydroxy-2-oxo-2H-chromen-3-ylmethyl)-benzoic acid 2,2,2-trifluoro-1-methyl-1-trifluoromethyl-ethyl ester (1.95 g).

Example 2

Preparation of 4-Hydroxy-3-(3-oxo-1,3-dihydro-isobenzofuran-1-yl)-chromen-2-one

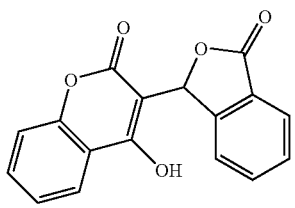

A solution of 4-hydroxy-chromen-2-one (650 mg) and 2-carboxybenzyladehyde (300 mg) in EtOH is heated to reflux for 4 hours, cooled to room temperature then concentrated in vacuo to give a crude oil, which is diluted with water.

The precipitated 4-hydroxy-chromen-2-one is collected by filtration (490 mg). A second crop of solid is collected from the mother liquor and triturated with hot EtOAc and filtered to provide 4-Hydroxy-3-(3-oxo-1,3-dihydro-isobenzofuran-1-yl)-chromen-2-one as white solid.

Example 3

Preparation of 2-(4-Hydroxy-2-oxo-2H-chromen-3-ylmethyl)-benzoic acid chloromethyl ester

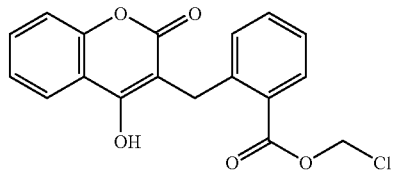

To a solution 4-Hydroxy-3-(3-oxo-1,3-dihydro-isobenzofuran-1-yl)-chromen-2-one (60 mg) in ethanol is added 10% Pd/C (10 mg) then stirred under a hydrogen balloon for 12 hours. The reaction mixture is filtered through a pad of celite and the filtrate concentrated in vacuo to give 2-(4-Hydroxy-2-oxo-2H-chromen-3-ylmethyl)-benzoic acid as white solid (50 mg). MS: 295 [M-H].

A solution of 2-(4-Hydroxy-2-oxo-2H-chromen-3-ylmethyl)-benzoic acid in a 5% sodium bicarbonate solution is added to a solution of 1.5 equivalent of chloromethylchlorosulfate in methylene chloride. Tetrabutylammonium hydrogensulfate (catalytic amount) is added, and the mixture stirred vigorously for 5 hours. The organic layer is dried over MgSO4 and conc. in vacuo to give 2-(4-Hydroxy-2-oxo-2H-chromen-3-ylmethyl)-benzoic acid chloromethyl ester as white solid.

Example 4

Preparation of 1,1,1,3,3,3-hexafluoro-2-methylpropan-2-yl 4-((4-hydroxy-2-oxo-2H-chromen-3-yl)methyl)benzoate Step 1 The preparation of 1,1,1,3,3,3-hexafluoro-2-methylpropan-2-yl 4-formylbenzoate

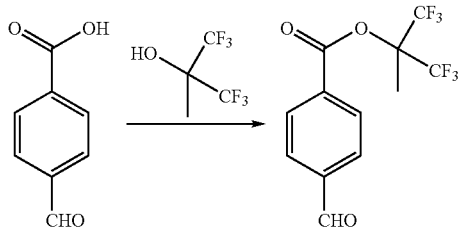

A mixture of 41.1 g (274 mmol) 4-carboxybenzaldehyde, 50 g (274 mmol) 1,1,1,3,3,3-hexafluoro-2-methyl-2-propanol, and 33.4 g (274 mmol) DMAP in 700 mL DCM was stirred until homogeneous (approximately 0.5 hr). The solution was cooled over an ice bath, under Ar, and 52.3 g (274 mmol) EDCI was added portion-wise. The reaction was stirred at RT for 48 hr. and concentrated to an oil on the rotovap. The oil was taken up with EA and washed with water, 2× with dil. Citric acid, 2× with dil. Sodium bicarbonate, and brine. The organic layer was dried over sodium sulfate and concentrated to 25.5 g pale yellow solid.

Step 2: Preparation of the Title Compound

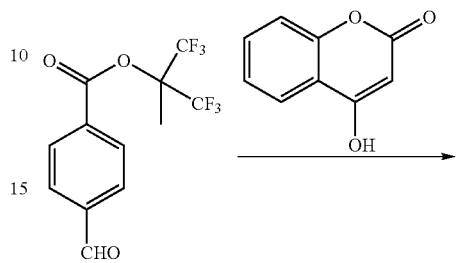

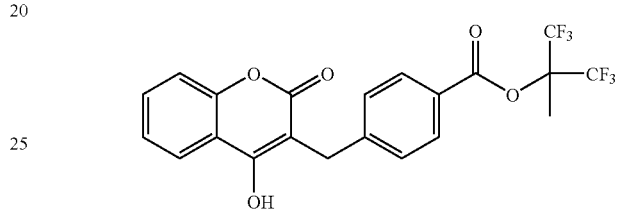

A mixture of 22 g (70 mmol) of the benzaldehyde, 11.3 g (70 mmol) of 4-hydroxycoumarin, and 70 mL of 1.2:1 (v/v) TEA/formic acid was heated to 140 C under nitrogen for 2 hrs. (3 hrs would have been better). Reaction progress was monitored by TLC using 1:1 (1% HOAc/EA)/Hexane. Mixture was allowed to cool briefly and treated with 50 mL THF (to inhibit crystallization) and poured into 500 mL of EA. The EA layer was washed 3× with water, once with brine and then dried over sodium sulfate. Filtration and concentration provided a white solid which can be recrystallized from EA or acetone.

If desired, the title compound can be converted into a pharmaceutically acceptable salt, such as the sodium salt.

Example 5

Preparation of 3,3,4,4,4-pentafluorobutan-2-yl 4-((4-hydroxy-2-oxo-2H-chromen-3-yl)methyl)benzoate Step 1: Preparation of 3,3,4,4,4-pentafluorobutan-2-yl 4-formylbenzoate (3)

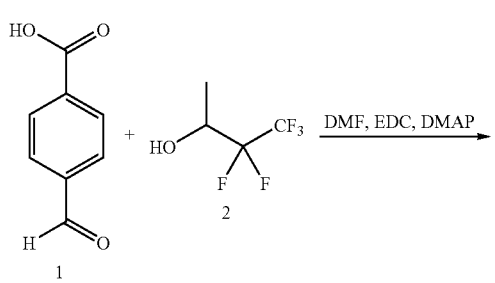

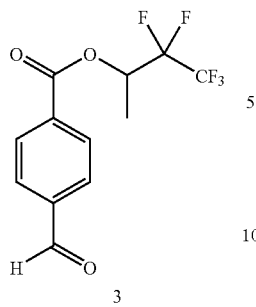

A mixture of 4-carboxybenzaldehyde (21.9 g, 145.9 mmol), 3,3,4,4,4-pentafluoro-2-butanol (24.1 g, 146.9 mmol), EDC (33.5 g, 174.8 mmol) and DMAP (18.1 g, 148.1 mmol) was dissolved in DMF (60 ml) at rt. It was stirred for 36 h at rt. Hexane was added, it was washed with 1 N HCl, sat NaHCO$_3$ and brine. The aqueous layers were extracted three times with hexane. It was dried over Na$_2$SO$_4$, filtered, concentrated, and the residue was purified by silica gel chromatography (ethyl acetate:hexane 1:10) to yield the desired aldehyde as a yellow oil (67%).

Step 2: Preparation of the Title Compound

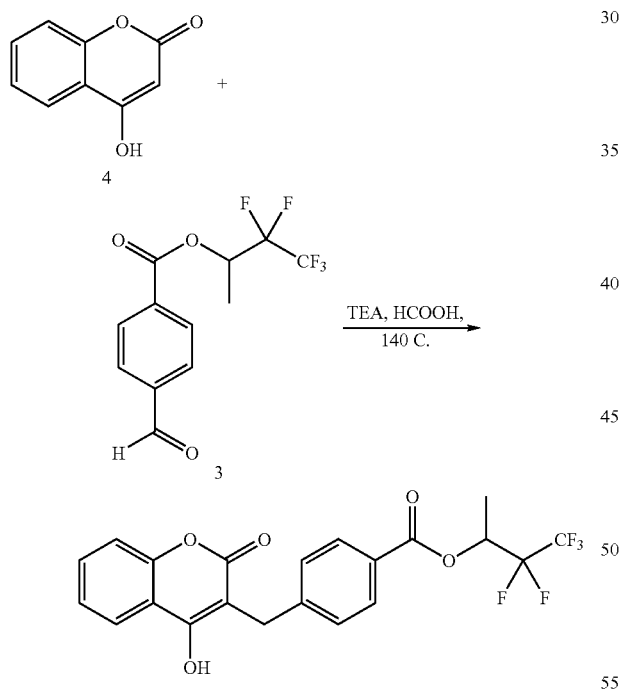

Formic acid (35.8 ml) was added to 4-Hydroxycoumarin (15.8 g, 97.5 mmol) and aldehyde 3 (28.9 g, 97.6 mmol). Triethylamine (43 ml) was added (exothermic) at 0° C. It was warmed to 140° C. and stirred for 4 h at this temperature. The yellow solution was cooled to rt, ethyl acetate was added, it was washed with 1 N HCl and brine, it was dried over Na$_2$SO$_4$ and the solvent was removed. The slightly yellow solid was recrystallized from ethylacetate to yield the title compound as a white solid in 98% purity (60% yield).

The sodium salt was made as follows: the free acid (21.39 g, 48.35 mmol) and NaHCO$_3$ (4.06 g, 48.30 mmol) were dissolved in acetonitrile (400 ml) and water (100 ml) and lyophilized to yield the Na-salt, as a white solid.

Example 6

Preparation of (S)—((R)-3,3,4,4,4-pentafluorobutan-2-yl) 2-(6-methoxynaphthalen-2-yl)propanoate Step 1: Preparation of (2S)-3,3,4,4,4-pentafluorobutan-2-yl 2-(6-methoxynaphthalen-2-yl)propanoate (mix of diastereomers) (6)

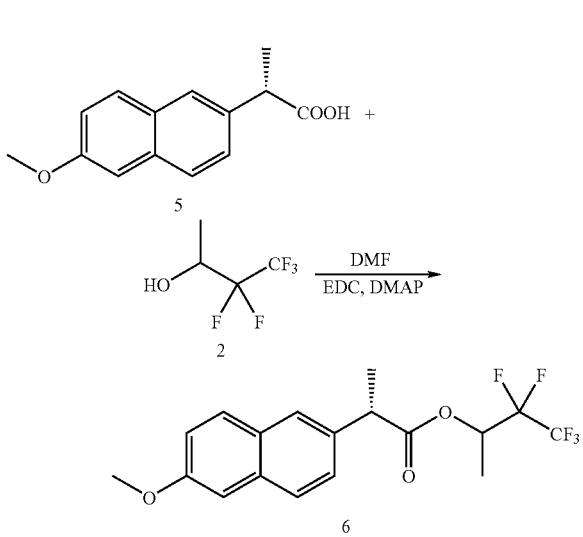

A mixture of (S)-naproxen (9.23 g, 40.1 mmol), racemic 3,3,4,4,4-pentafluoro-2-butanol (6.58 g, 40.1 mmol), EDC (9.20 g, 48.0 mmol) and DMAP (4.89 g, 40.0 mmol) was dissolved in CH$_2$Cl$_2$ (40 mL) at room temperature. After stirring for 8 h at room temperature, the mixture was diluted with CH$_2$Cl$_2$, then washed successively with 1 N HCl, sat. NaHCO$_3$, and brine. After drying over Na$_2$SO$_4$ and concentrating, a mixture of diastereomeric naproxen esters was obtained as a white solid.

Step 2: Small amounts of the diastereomers were separated via reverse phase HPLC (C$_{18}$-column, with 50% to 70% CH$_3$CN/water.)

(S,S)-Naproxen ester (single diastereomer) $^1$H NMR (CDCl$_3$, 400 MHz) δ 7.70 (d, J=8.8 Hz, 2H), 7.65 (d, J=1.2 Hz, 1H), 7.37 (dd J=1.8, 8.6 Hz, 1H), 7.15 (dd, J=2.8, 8.8 Hz, 1H), 7.12 (d, J=2.4 Hz, 1H), 5.35-5.42 (m, 1H), 3.92 (s, 3H), 3.90 (q, J=7.2 Hz, 1H), 1.60 (d, J=7.2 Hz, 3H), 1.39 (d, J=6.0 Hz, 3H); $^{19}$F NMR (CDCl$_3$, 376 MHz) δ −82.0 (s, 3F), −122.7 (dd, J=7.0, 278.2 Hz, 1F), −128.6 (dd, J=16.0, 278.9 Hz, 1F).

(S,R)-Naproxen ester (single diastereomer) $^1$H NMR (CDCl$_3$, 400 MHz) δ 7.71 (d, J=8.4 Hz, 2H), 7.66 (d, J=1.2 Hz, 1H), 7.38 (dd, J=1.8, 8.6 Hz, 1H), 7.15 (dd, J=2.4, 8.8 Hz, 1H), 7.12 (d, J=2.4 Hz, 1H), 5.39-5.47 (m, 1H), 3.92 (s, 3H), 3.90 (q, J=7.2 Hz, 1H), 1.59 (d, J=7.2 Hz, 3H), 1.27 (d, J=6.4 Hz, 3H); $^{19}$F NMR (CDCl$_3$, 376 MHz) δ −82.0 (s, 3F), −122.7 (dd, J=7.0, 278.2 Hz, 1F), −128.6 (dd, J=16.0, 279.1 Hz, 1F).

Step 3: The Naproxen resolving agent was hydrolytically removed

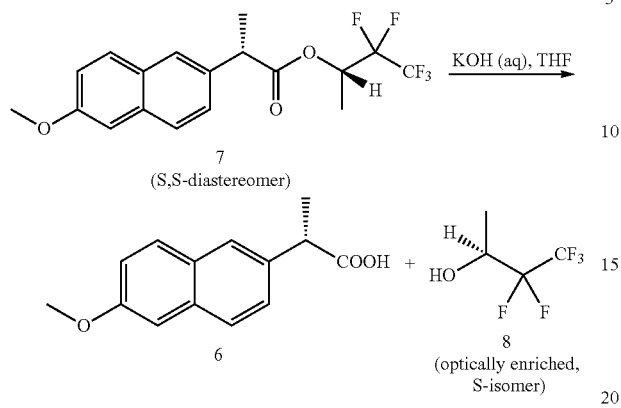

The (S,S)—Naproxen ester (3.83 g, 10.18 mmol) from step 2 was treated with 1 N KOH (19 ml) and THF (19.5 mL) at room temperature. The emulsion was stirred at room temperature and became a clear solution after 3 h. After stirring for one additional hour, CH$_2$Cl$_2$ (50 mL) was added and the solution was washed with sat. NaHCO$_3$ (four times) and dried over Na$_2$SO$_4$ and filtered to afford a solution of the S isomer of the alcohol. The solution was used directly in the next step, without purification.

Step 4: The ester is formed

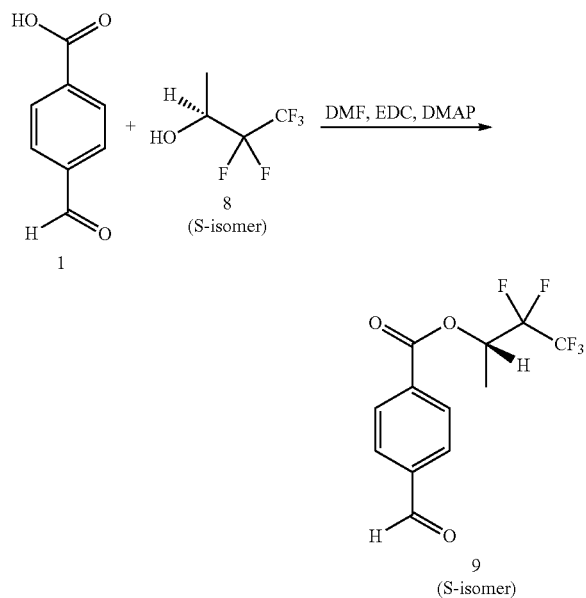

To a solution of the S isomer of the alcohol from step 3) was added 4-carboxybenzaldehyde (3.35 g, 22.3 mmol), EDC (5.14 g, 26.8 mmol) and DMAP (2.70 g, 22.1 mmol). The reaction mixture was stirred for 16 h at room temperature. Ethyl acetate was added and the organic layer was washed successively with sat. NaHCO$_3$(aq) and brine. After drying over Na$_2$SO$_4$, filtering, and concentrating, the residue was purified by silica gel chromatography (ethyl acetate:hexane 1:10) to yield (S)-4-formyl-benzoic acid 2,2,3,3,3-pentafluoro-1-methyl-propyl ester as a yellow oil (82%).

Step 5: The final coupling—preparation of (S)-3,3,4,4,4-pentafluorobutan-2-yl 4-((4-hydroxy-2-oxo-2H-chromen-3-yl)methyl)benzoate

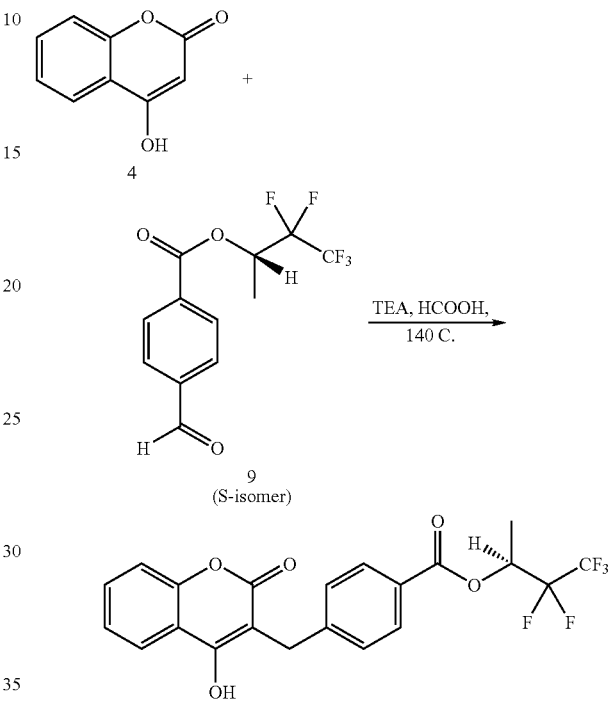

4-Hydroxycoumarin (1.367 g, 8.44 mmol) and (S)-4-formyl-benzoic acid 2,2,3,3,3-pentafluoro-1-methyl-propyl ester (2.505 g, 8.46 mmol) were dissolved in formic acid (3.0 mL) and Et$_3$N (3.6 mL) at 0° C. After stirring at 140° C. for 4 h, the yellow solution was cooled to rt, EtOAc was added, and the organic layer was washed successively with 1 N HCl and brine. After drying over Na$_2$SO$_4$ and concentrating, the pale yellow solid was purified twice by silica gel chromatography (DCM:MeOH 100:6 and DCM:MeOH 100:5) to yield the title compound in 92.5% ee as determined by chiral HPLC.

The sodium salt was made as follows: The free acid (1.60 g, 3.62 mmol) and NaHCO$_3$ (303 mg, 3.62 mmol) were dissolved in acetonitrile (25 mL) and water (5 mL), and then lyophilized to yield the desired Na-salt, as a white solid. MS m/e 465 (MNa$^+$), 441 (M-H); $^1$H NMR (DMSO-d$_6$) δ 7.76-7.80 (m, 3H), 7.43 (d, J=8.3 Hz, 2H), 7.31 (dt, 1H), 7.02-7.08 (m, 2H), 5.71-5.79 (m, 1H), 3.70 (s, 2H), 1.48 (d, J=6.9 Hz, 3H); $^{19}$F NMR (DMSO-d$_6$) δ −81.3 (s, 3F), −121.2 (dd, J=7.0, 276.7 Hz, 1F), −128.2 (d, J=17.1, 276.7 Hz, 1F).

Example 7

Preparation of (R)-3,3,4,4,4-pentafluorobutan-2-yl 4-((4-hydroxy-2-oxo-2H-chromen-3-yl)methyl)benzoate Using methods and procedures essentially analogous to those in Example 6, the (S,R) diastereomer from Example 6, step 2 was hydrolyzed to afford the desired (R)-isomer of the alcohol, which was then coupled with 4-carboxybenzaldehyde to afford (R)-3,3,4,4,4-pentafluorobutan-2-yl 4-formyl-benzoate, which was then coupled with 4-hydroxycoumarin to afford the title compound.

The sodium salt was made as follows: the free acid (1.605 g, 3.63 mmol) and NaHCO$_3$ (303 mg, 3.62 mmol) were dissolved in acetonitrile (20 mL), water (5 mL), and then lyophilized to yield the Na-salt, as a white solid. MS m/e 465 (MNa$^+$), 441 (M-H); $^1$H NMR (DMSO-d$_6$) δ 7.81 (dd, J=1.1, 7.9 Hz, 1H), 7.77-7.80 (m, 2H), 7.43 (d, J=8.3 Hz, 2H), 7.32-7.36 (m, 1H), 7.05-7.11 (m, 2H), 5.71-5.80 (m, 1H), 3.72 (s, 2H), 1.49 (d, J=6.1 Hz, 3H); $^{19}$F NMR (DMSO-d$_6$) δ −81.3 (s, 3F), −121.2 (dd, J=6.0, 265.6 Hz, 1F), −128.2 (dd, J=16.2, 265.8 Hz, 1F).

Example 8

The following compounds were prepared essentially according to the methods and schemes described herein.

| Name |
| --- |
| 3-(4-hydroxy-2-oxo-2H-chromen-3-yl)-3-phenylpropanoic acid |
| methyl 3-(4-hydroxy-2-oxo-2H-chromen-3-yl)-3-phenylpropanoate |
| ethyl 3-(4-hydroxy-2-oxo-2H-chromen-3-yl)-3-phenylpropanoate |
| 3-(4-hydroxy-2-oxo-2H-chromen-3-yl)-3-phenylpropanamide |
| 2-hydroxyethyl 3-(4-hydroxy-2-oxo-2H-chromen-3-yl)-3-phenylpropanoate |
| 2,2,3,3,3-pentafluoropropyl 3-(4-hydroxy-2-oxo-2H-chromen-3-yl)-3-phenylpropanoate |
| 3,3,3-trifluoropropyl 3-(4-hydroxy-2-oxo-2H-chromen-3-yl)-3-phenylpropanoate |
| 2-(phenylsulfonyl)ethyl 3-(4-hydroxy-2-oxo-2H-chromen-3-yl)-3-phenylpropanoate |
| 2-(methylsulfonyl)ethyl 3-(4-hydroxy-2-oxo-2H-chromen-3-yl)-3-phenylpropanoate |
| 2-(4-fluorophenyl)ethyl 3-(4-hydroxy-2-oxo-2H-chromen-3-yl)-3-phenylpropanoate |
| 2,2,2-trifluoro-1,1-dimethylethyl 3-(4-hydroxy-2-oxo-2H-chromen-3-yl)-3-phenylpropanoate |
| 2,2,2-trifluoro-1-phenylethyl 3-(4-hydroxy-2-oxo-2H-chromen-3-yl)-3-phenylpropanoate |
| 2-[(4-hydroxy-2-oxo-2H-chromen-3-yl)methyl]benzoic acid |
| {4-[(4-hydroxy-2-oxo-2H-chromen-3-yl)methyl]phenyl}acetic acid |
| {4-[(4-hydroxy-2-oxo-2H-chromen-3-yl)methyl]phenyl}acetic acid |
| methyl 2-[(4-hydroxy-2-oxo-2H-chromen-3-yl)methyl]benzoate |
| 3-{2-[(4-hydroxy-2-oxo-2H-chromen-3-yl)methyl]phenyl}propanoic acid |
| ethyl 3-{2-[(4-hydroxy-2-oxo-2H-chromen-3-yl)methyl]phenyl}propanoate |
| 3-(4-hydroxy-2-oxo-2H-chromen-3-yl)-3-(4-methoxyphenyl)propanoic acid |
| sodium 3-[3-ethoxy-1-(4-methoxyphenyl)-3-oxopropyl]-2-oxo-2H-chromen-4-olate |
| 3-(4-hydroxy-2-oxo-2H-chromen-3-yl)butanoic acid |
| ethyl 3-(4-hydroxy-2-oxo-2H-chromen-3-yl)butanoate |
| 4-[3-ethoxy-1-(4-hydroxy-2-oxo-2H-chromen-3-yl)-3-oxopropyl]benzoic acid |
| ethyl 4-[3-ethoxy-1-(4-hydroxy-2-oxo-2H-chromen-3-yl)-3-oxopropyl]benzoate |
| 3-(4-hydroxy-2-oxo-2H-chromen-3-yl)hexanoic acid |
| ethyl 3-(4-hydroxy-2-oxo-2H-chromen-3-yl)hexanoate |
| 3-(4-hydroxy-2-oxo-2H-chromen-3-yl)-5-methylhexanoic acid |
| ethyl 3-(4-hydroxy-2-oxo-2H-chromen-3-yl)-5-methylhexanoate |
| 3-(4-chlorophenyl)-3-(4-hydroxy-2-oxo-2H-chromen-3-yl)propanoic acid |
| 3-(3,4-dichlorophenyl)-3-(4-hydroxy-2-oxo-2H-chromen-3-yl)propanoic acid |
| 3-(2,3-dihydro-1,4-benzodioxin-6-yl)-3-(4-hydroxy-2-oxo-2H-chromen-3-yl)propanoic acid |
| ethyl 3-(2,3-dihydro-1,4-benzodioxin-6-yl)-3-(4-hydroxy-2-oxo-2H-chromen-3-yl)propanoate |
| 4-[bis(4-hydroxy-2-oxo-2H-chromen-3-yl)methyl]benzoic acid |
| 3-(4-hydroxy-2-oxo-2H-chromen-3-yl)propanoic acid |
| ethyl 3-(4-hydroxy-2-oxo-2H-chromen-3-yl)propanoate |
| cyclohexyl 3-(4-hydroxy-2-oxo-2H-chromen-3-yl)propanoate |
| methyl 4-[bis(4-hydroxy-2-oxo-2H-chromen-3-yl)methyl]benzoate |
| 5-[(4-hydroxy-2-oxo-2H-chromen-3-yl)methyl]-2-methoxybenzoic acid |
| methyl 5-[(4-hydroxy-2-oxo-2H-chromen-3-yl)methyl]-2-methoxybenzoate |
| 5-[(4-hydroxy-2-oxo-2H-chromen-3-yl)methyl]-2-isopropoxybenzoic acid |
| methyl 5-[(4-hydroxy-2-oxo-2H-chromen-3-yl)methyl]-2-isopropoxybenzoate |
| isopropyl 5-[(4-hydroxy-2-oxo-2H-chromen-3-yl)methyl]-2-isopropoxybenzoate |
| ethyl 2-{4-[(4-hydroxy-2-oxo-2H-chromen-3-yl)methyl]phenoxy}-2-methylpropanoate |
| methyl N-{4-[(4-hydroxy-2-oxo-2H-chromen-3-yl)methyl]benzoyl}-L-valine |
| methyl N-{4-[(4-hydroxy-2-oxo-2H-chromen-3-yl)methyl]benzoyl} glycinate |
| methyl N-{4-[(4-hydroxy-2-oxo-2H-chromen-3-yl)methyl]benbzoyl}-N-methylglycinate |
| 3-(4-hydroxy-2-oxo-2H-chromen-3-yl)-3-[4-(trifluoromethoxy)phenyl]propanoic acid |
| ethyl 3-(6-fluoro-4-hydroxy-2-oxo-2H-chromen-3-yl)-3-phenylpropanoate |
| methyl N-[3-(4-hydroxy-2-oxo-2H-chromen-3-yl)-3-(4-methoxyphenyl)propanoyl]glycinate |
| {4-[(4-hydroxy-2-oxo-2H-chromen-3-yl)methyl]phenoxy}acetic acid |
| methyl {4-[(4-hydroxy-2-oxo-2H-chromen-3-yl)methyl]phenoxy}acetate |
| ethyl 2-[bis(4-hydroxy-2-oxo-2H-chromen-3-yl)methyl]benzoate |
| ethyl 4-[(6-fluoro-4-hydrpoxy-2-oxo-2H-chromen-3-yl)methyl]benzoate |
| 3-(4-hydroxy-2-oxo-2H-chromen-3-yl)-3-(1-naphthyl)propanoic acid |
| methyl 3-(4-hydroxy-2-oxo-2H-chromen-3-yl)-3-(1-naphthyl)propanoate |
| 3-(4-hydroxy-2-oxo-2H-chromen-3-yl)-3-(2-naphthyl)propanoic acid |
| methyl 3-(4-hydroxy-2-oxo-2H-chromen-3-yl)-3-(2-naphthyl)propanoate |
| 3-{4-[(4-hydroxy-2-oxo-2H-chromen-3-yl)methyl]phenyl}propanoic acid |
| methyl 3-{4-[(4-hydroxy-2-oxo-2H-chromen-3-yl)methyl]phenyl}propanoate |
| 4-hydroxy-3-(4-hydroxybenzyl)-2H-chromen-2-one |
| 4-[(4-hydroxy-2-oxo-2H-chromen-3-yl)methyl]phenyl propionate |
| 4-[(4-hydroxy-2-oxo-2H-chromen-3-yl)methyl]phenyl pivalate |
| 4-[(4-hydroxy-2-oxo-2H-chromen-3-yl)methyl]phenyl benzoate |
| 4-[(4-hydroxy-2-oxo-2H-chromen-3-yl)methyl]phenyl 2,6-dimethylbenzoate |
| 4-[(4-hydroxy-2-oxo-2H-chromen-3-yl)methyl]phenyl 2-methylbenzoate |
| 6-[(4-hydroxy-2-oxo-2H-chromen-3-yl)methyl]-2-naphthoic acid |
| ethyl 6-[(4-hydroxy-2-oxo-2H-chromen-3-yl)methyl]-2-naphthoate |
| 3-(benzylamino)-4-hydroxy-2H-chromen-2-one |
| 3-(4-hydroxy-2-oxo-2H-chromen-3-yl)-3-[4-(trifluoromethoxy)phenyl]propanoic acid |
| 4-hydroxy-3-(3-oxo-1,3-dihydro-2-benzofuran-1-yl)-2H-chromen-2-one |
| 3-benzyl-4-hydroxy-2H-chromen-2-one |
| 4-hydroxy-3-(3-hydroxy-1-phenylpropyl)-2H-chromen-2-one |
| 3-(4-hydroxy-2-oxo-2H-chromen-3-yl)-3-[4-(trifluoromethoxy)phenyl]propanoic acid |
| (3S)-3-(3,4-dichlorophenyl)-3-(4-hydroxy-2-oxo-2H-chromen-3-yl)propanoic acid |
| (3R)-3-(3,4-dichlorophenyl)-3-(4-hydroxy-2-oxo-2H-chromen-3-yl)propanoic acid |
| 2-benzyl-3-(4-hydroxy-2-oxo-2H-chromen-3-yl)propanoic acid |
| ethyl 2-benzyl-3-(4-hydroxy-2-oxo-2H-chromen-3-yl)propanoate |
| 3-cyclohexyl-3-(4-hydroxy-2-oxo-2H-chromen-3-yl)propanoic acid |
| ethyl 3-cyclohexyl-3-(4-hydroxy-2-oxo-2H-chromen-3-yl)propanoate |

-continued

Name ethyl 2-(4-hydroxy-2-oxo-2H-chromen-3-yl)butanoate
(4-hydroxy-2-oxo-2H-chromen-2-yl)(phenyl)acetic acid
ethyl (4-hydroxy-2-oxo-2H-chromen-3-yl)(phenyl)acetate
4-[(4-hydroxy-2-oxo-2H-chromen-3-yl)methyl]benzoic acid
methyl 4-[(4-hydroxy-2-oxo-2H-chromen-3-yl)methyl]benzoate
ethyl 4-[(4-hydroxy-2-oxo-2H-chromen-3-yl)methyl]benzoate
butyl 4-[(4-hydroxy-2-oxo-2H-chromen-3-yl)methyl]benzoate
sodium 3-{4-[(2-hydroxyethoxy)carbonyl]benzyl}-2-oxo-2H-chromen-4-olate
isopropyl 4-[(4-hydroxy-2-oxo-2H-chromen-3-yl)methyl]benzoate
2,2-dimethylpropyl 4-[(4-hydroxy-2-oxo-2H-chromen-3-yl)methyl]benzoate
2-methoxyethyl 4-[(4-hydroxy-2-oxo-2H-chromen-3-yl)methyl]benzoate
2-pyrrolidin-1-ylethyl 4-[(4-hydroxy-2-oxo-2H-chromen-3-yl)methyl]benzoate
2,2,3,3,3-pentafluoropropyl 4-[(4-hydroxy-2-oxo-2H-chromen-3-yl)methyl]benzoate
2-(methylsulfonyl)ethyl 4-[(4-hydroxy-2-oxo-2H-chromen-3-yl)methyl]benzoate
3,3,3-trifluoropropyl 4-[(4-hydroxy-2-oxo-2H-chromen-3-yl)methyl]benzoate
2,2,3,3,3-pentafluoro-1-methylpropyl 4-[(4-hydroxy-2-oxo-2H-chromen-3-yl)methyl]benzoate
4-fluorobenzyl 4-[(4-hydroxy-2-oxo-2H-chromen-3-yl)methyl]benzoate
2-(4-fluorophenoxy)ethyl 4-[(4-hydroxy-2-oxo-2H-chromen-3-yl)methyl]benzoate
2-(phenylsulfonyl)ethyl 4-[(4-hydroxy-2-oxo-2H-chromen-3-yl)methyl]benzoate
cyclopropylmethyl 4-[(4-hydroxy-2-oxo-2H-chromen-3-yl)methyl]benzoate
2-fluoro-1-(fluoromethyl)ethyl 4-[(4-hydroxy-2-oxo-2H-chromen-3-yl)methyl]benzoate
2,2,2-trifluoro-1-methylethyl 4-[(4-hydroxy-2-oxo-2H-chromen-3-yl)methyl]benzoate
2,2,2-trifluoro-1-(trifluoromethyl)ethyl 4-[(4-hydroxy-2-oxo-2H-chromen-3-yl)methyl]benzoate
phenyl 4-[(4-hydroxy-2-oxo-2H-chromen-3-yl)methyl]benzoate
2,3-dimethylphenyl 4-[(4-hydroxy-2-oxo-2H-chromen-3-yl)methyl]benzoate
2-methylphenyl 4-[(4-hydroxy-2-oxo-2H-chromen-3-yl)methyl]benzoate
2,2,2-trifluoro-1-methyl-1-(trifluoromethyl)ethyl 4-[(4-hydroxy-2-oxo-2H-chromen-3-yl)methyl]benzoate
2,6-dimethylphenyl 4-[(4-hydroxy-2-oxo-2H-chromen-3-yl)methyl]benzoate
2-(phenylsulfinyl)ethyl 4-[(4-hydroxy-2-oxo-2H-chromen-3-yl)methyl]benzoate
4-fluoro-2-methylphenyl 4-[(4-hydroxy-2-oxo-2H-chromen-3-yl)methyl]benzoate
2,2,3,3,3-pentafluoro-1-methylpropyl 4-[(4-hydroxy-2-oxo-2H-chromen-3-yl)methyl]benzoate
2,2,3,3,3-pentalfuoro-1-methylpropyl 4-[(4-hydroxy-2-oxo-2H-chromen-3-yl)methyl]benzoate
(1S)-2,2,2-trifluoro-1-hydroxyethyl 4-[(4-hydroxy-2-oxo-2H-chromen-3-yl)methyl]benzoate
(1R)-2,2,2-trifluoro-1-hydroxyethyl 4-[(4-hydroxy-2-oxo-2H-chromen-3-yl)methyl]benzoate
4-hydroxy-3-(3-oxo-1-phenylbutyl)-2H-chromen-2-one Example 9

Effects of Compounds on Vitamin K Epoxide Reductase Activity

Compounds of the subject invention were tested against vitamin K epoxide reductase.

Briefly: increasing concentrations of compounds were incubated in the presence of vitamin K epoxide and in the presence of a bovine microsomal preparation containing vitamin K epoxide reductase. The amount of residual vitamin K epoxide at the end of the incubation period was directly proportional to the inhibitory activity of the test compounds on the enzyme.

The tests were performed as follows:

Microsomes were prepared from fresh cow liver according to the method described in: "Purification of gamma-glutamyl carboxylase from bovine liver. Wu S M, Mutucumarana V P, and Stafford D W. Methods in Enzymology (1997) 282:346-57."

Serial dilutions of test compounds were prepared as follows: Dissolve the test compounds to a final dilution of 10 mM either in water or in DMSO (if not soluble in water). From this mother solution, prepare 2 further dilutions by diluting it with water: one 200 µM solution and one 5 mM solution. Prepare a series of tubes as follows:

TABLE 1

| Tube# | Substrate | Water (µL) |
|---|---|---|
| 1 | 30 µL of 200 µM solution | 0 |
| 2 | 20 µL of 200 µM solution | 10 |
| 3 | 10 µL of 200 µM solution | 20 |
| 4 | 45 µL of 5 µM solution | — |
| 5 | | 30 |
| 6 | | 30 |
| 7 | | 30 |
| 8 | | 30 |
| 9 | | 30 |

Remove 15 µL from tube 4 and add to tube 5, vortex, then remove 15 µL from tube 5 and add to tube 6, vortex, etc. . . . until 15 µL is added to tube 9. Vortex and then remove 15 µL from tube 9.

Prepare another set of 4 tubes and add 30 µL of water.

A reaction mixture consisting of 600 µL buffer (2.5M NaCl, 0.125M MOPS, pH7.5), 520 µL water, and 150 µL of 10% CHAPS was prepared. The tubes were kept on ice for 5 minutes and then 500 µL of microsomal preparation was added. The mixture was mixed by vortex and kept on ice for 10 min for sufficient solubilization. To this was added 150 µL of vitamin K epoxide solution (1.5 mg/ml in isopropanol), then again vortexed and kept on ice for 5 minutes. An aliquot (70 µL) of this reaction mix was added to each one of the series of tubes prepared as above and containing serial dilutions of test compounds in 30 µL of water. The tubes were then vortexed and then kept on ice for 5 min. To 2 of the water-containing tubes was added 500 µL of a stop reagent consisting of 5 volumes of 50 mM AgNO$_3$ and 5 volumes of isopropanol. These 2 tubes were used to measure a zero value.

The tubes were placed in a 30 C mixer for 3 min and 5 µL of 100 mM DTT solution in water was added. The tubes were then vortexed and kept in the dark without shaking for another 20 min, at the end of which 500 µL of the stop reagent was added.

To each tube was then added 600 µL of a 100 µg/ml solution of vitamin E in hexane, the tubes were capped and then vortexed for 1 minute. The tubes were then centrifuged for 5 min at 5,000 g, and the upper layer (the hexane layer) was transferred to a series of fresh tubes. The hexane was evaporated at room temperature in the dark using a speedvac, and the resulting pellet was resuspended in 100 µL of methanol.

The amount of vitamin K epoxide in each sample was then measured using a HPLC determination method. Residual vitamin K epoxide was then plotted against test compound concentration. The results are shown in FIGS. 1-9

Example 10

Metabolism in Pooled Human Microsomes

Pooled human liver microsomes were used as an in vitro model of drug metabolism. These microsomes contain both esterase and CYP450 drug metabolizing enzymes. Pooled human microsomes were suspended in Tris buffer (50 mM, pH 7.4) at a final concentration of 1 mg/mL of microsomal protein. Test compounds dissolved in acetonitrile:DMSO (1:99) were added to a final concentration of 2 μM. Incubations were performed at 37° C. and samples (50 μL) were collected after 5, 15, 30, 60 and 90 minutes and then were precipitated by the addition of 100 μL of acetonitrile containing Internal Standard and centrifuged at 14,000 rpm for 15 min at 4° C. Samples were analyzed by LC/MS/MS for the content of parent drug.

To determine the role of CYP450 in the metabolism, incubations were run either with or without an NADPH regenerating system–NADPH is an obligate cofactor for CYP450 enzymes. Incubations that included NADPH cofactor represent the total metabolism by CYP450+ esterase. Incubations that do not contain any NADPH represent esterase metabolism alone. Thus, when the relative decline of parent drug observed is greater in the presence of NADPH, the metabolism is CYP450-mediated. When the relative decline is equivalent in the presence and absence of cofactor the metabolism is esterase mediated.

An additional set of incubations was run as a control: these incubations did not contain microsomes and established the stability of the compound in the test system. All of the compounds were stable.

The test compounds had the general formula:

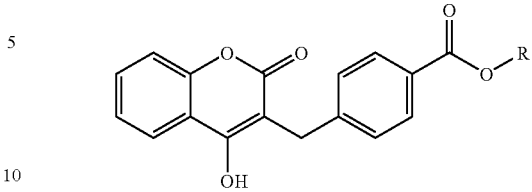

wherein R represents a group capable of forming an ester moiety. Similar structures were tested such that the only difference was the presence or the absence of a halogen atom in the ester group. Results are shown in FIGS. 12-14.

Similarly, compounds were tested in which R is $CH_3$, $CH_2$—$CH_3$, $(CH_2)_3CH_3$, $CH_2$—$CH_2$—OH, $CH_2$—$C(CH_3)_3$, $CH_2$—$CH_2$—O—$CH_3$, 1-pyrrolidinylethyl, $CH_2$—$CH_2$—$SO_2$—$CH_3$, benzyl, $CH_2$—$CH_2$—O-Phenyl, $CH_2$—$CH_2$—$SO_2$-Phenyl, $CH_2$-Cyclopropyl, phenyl, substituted phenyl. In all cases CYP450 was either the only metabolic agent, or if esterases were present, CYP450 was the major pathway. Other halogenated esters were tested such as compounds in which R is $CH(CH_2F)_2$, $C(CH_3)(CF_3)_2$, polyfluorinated cyclohexyl. In every case the metabolism was mainly by esterase.

In a separate set of incubations the effects of paraoxon, a known esterase inhibitor, were tested in order to confirm that the metabolism observed was due to esterase. Paraoxon, at a final concentration of 320 μg/mL, effectively inhibited the metabolism of the halogenated esters, as is shown in FIG. 15, confirming that esterase was the primary enzyme involved in the metabolism of halogenated compounds.

Further data generated essentially using the assay protocol described above appears below.

| Structure | VKER $IC_{50}$ (μM) | CYP + Esterase % Stability at 90 min (Est $T^{1/2}$) | Esterase % Stability at 90 min (Est $T^{1/2}$) | Buffer % Stability at 90 min (Est $T^{1/2}$) |
|---|---|---|---|---|
| Stability of Several Compounds (at 2 μM final concentration) in Pooled Human Microsomes | | | | |
| [coumarin-benzyl-CO2H structure] | >30.00 | 101% (>90 min) | ND | 99% (>90 min) |
| [coumarin-benzyl-ester-CF3 structure, Racemic] | 3.38 | 69%** (>90 min) | 70%** (>90 min) | 108%** (>90 min) |
| [coumarin-benzyl-ester-perfluoro structure] | 5.07 | 90%** (>90 min) | 96%** (>90 min) | 92%** (>90 min) |

-continued

Stability of Several Compounds (at 2 μM final concentration) in Pooled Human Microsomes

| Structure | VKER IC$_{50}$ (μM) | CYP + Esterase % Stability at 90 min (Est T$^{1/2}$) | Esterase % Stability at 90 min (Est T$^{1/2}$) | Buffer % Stability at 90 min (Est T$^{1/2}$) |
|---|---|---|---|---|
| S-isomer | 4.02 | 70% (>90 min) | 86% (>90 min) | 123% (>90 min) |
| R-isomer | 4.15 | 24% (~30 min) | 27% (~30 min) | 113% (>90 min) |
| Warfarin | 3.0 ± 0.8* | | | |

*is the average of 3 experiments conducted on 3 separate days.
The results indicate that incorporation of an ester bond makes it possible to shift metabolism from CYP-mediated degradation to carboxylesterase-mediated pathways.

Example 11

HEK-293 Cell Study

Electrophysiological recordings of I$_{Kr}$ in stably transfected HEK-293 cells were made in the whole cell configuration of the patch-clamp technique (Hamill et al, 1981) using an Axopatch 200B amplifier (Axon Instruments, Foster City, Calif.). Patch microelectrodes were pulled from 1.5-mm borosilicate glass tubing using a two-stage vertical pipette puller (Narishige, East Meadow, N.Y.). When filled with recording solution, patch microelectrodes had a resistance of 3-5 MΩ. HEK-293 cells were plated in 35 mm plastic cell and tissue culture dishes for 2-3 days. For application of drug-containing solutions to cells, the SF-77B system (Warner Instrument Corp, Hamden, Conn.) was used. Solution exchanges were completed within 20 ms. Current data were digitized online using a DigiData 1200A analog-to-digital board (Axon Instruments) and stored on the hard disc of an IBM compatible Pentium computer (GP7-600 MHz, Gateway Computer, Sioux City, N. Dak.). Voltage-clamp experimental protocols and off-line data analysis were performed using the software program pCLAMP7 (Axon Instruments). The experiments were performed at room temperature (22-23° C.).

The composition of the extracellular control solution is described in the table below. Its pH was adjusted to 7.4 using NaOH.

The solution for filling the patch electrodes is described in the table below and its pH was adjusted to 7.4 using KOH.

| | Electrophysiological recordings of I$_{Kr}$ |
|---|---|
| Source | mammalian HEK-293 cells expressing the hERG gene |
| Potential | −80 mV |
| Depolarization | +10 mV for 20 s |
| Repolarization | −50 mM for 5 s |
| Incubation Temperature | 22-23° C. |
| Extracellular solution | NaCl 140 mM, KCl 4 mM, CaCl$_2$ 2 mM, MgCl$_2$ 1 mM, 4-(2-hydroxyethyl)-1-piperazineethanesulfonic acid (HEPES) 10 mM, and glucose 11 mM |
| Electrode Buffer | Potassium gluconate 135 mM, MgCl$_2$ 1 mM, ethyleneglycoltetraacetic acid (EGTA) 5 mM, HEPES 10 mM, MgATP 5 mM |

The effect of warfarin, 2,2,2-trifluoro-1-methyl-1-(trifluoromethyl)ethyl 4-[(4-hydroxy-2-oxo-2H-chromen-3-yl)methyl]benzoate and its corresponding acid metabolite, 4-[(4-hydroxy-2-oxo-2H-chromen-3-yl)methyl]benzoic acid on I$_{Kr}$ was studied in a stably transfected HEK-293 cell line using a two-pulse protocol. Cells were clamped at a holding potential of −80 mV and depolarized to +10 mV for a 20 s period to activate I$_{Kr}$ and then a repolarizing step to −50 mV was applied for 5 sec to elicit an outward deactivating tail current (tail I$_{Kr}$). The two-pulse protocol was applied every 45 s. Tail I$_{Kr}$ amplitude was measured as the difference between the peak current and baseline current at −50 mV in control and in the presence of ATI-compounds when steady-state block was obtained.

The study showed that 2,2,2-trifluoro-1-methyl-1-(trifluoromethyl)ethyl 4-[(4-hydroxy-2-oxo-2H-chromen-3-yl)methyl]benzoate and its corresponding acid metabolite, 4-[(4-hydroxy-2-oxo-2H-chromen-3-yl)methyl]benzoic acid, had no inhibitory effect on human $I_{Kr}$. ($IC_{50}$>100 and >1000 µM, respectively.) Nor did either compound exhibit significant activity in a broad cellular and biochemical receptor screening assay, at concentrations up to 10 µM.

Modifications of the compounds disclosed herein can readily be made by those skilled in the art. Thus, analogs, derivatives, enantiomers and salts of the exemplified compounds are within the scope of the subject invention. With knowledge of the compounds of the subject invention, and their structures, skilled chemists can use known procedures to synthesize these compounds from available substrates.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound that is
2,2,3,3,3-pentafluoropropyl 4-[(4-hydroxy-2-oxo-2H-chromen-3-yl)methyl]benzoate;
3,3,3-trifluoropropyl 4-[(4-hydroxy-2-oxo-2H-chromen-3-yl)methyl]benzoate;
2,2,3,3,3-pentafluoro-1-methylpropyl 4-[(4-hydroxy-2-oxo-2H-chromen-3-yl)methyl]benzoate;
4-fluorobenzyl 4-[(4-hydroxy-2-oxo-2H-chromen-3-yl)methyl]benzoate;
2-(4-fluorophenoxy)ethyl 4-[(4-hydroxy-2-oxo-2H-chromen-3-yl)methyl]benzoate;
2-fluoro-1-(fluoromethyl)ethyl 4-[(4-hydroxy-2-oxo-2H-chromen-3-yl)methyl]benzoate;
2,2,2-trifluoro-1-methylethyl 4-[(4-hydroxy-2-oxo-2H-chromen-3-yl)methyl]benzoate;
2,2,2-trifluoro-1-(trifluoromethyl)ethyl 4-[(4-hydroxy-2-oxo-2H-chromen-3-yl)methyl]benzoate;
2,2,3,3,3-pentafluoro-1-methylpropyl 4-[(4-hydroxy-2-oxo-2H-chromen-3-yl)methyl]benzoate;
2,2,3,3,3-pentafluoro-1-methylpropyl 4-[(4-hydroxy-2-oxo-2H-chromen-3-yl)methyl]benzoate;
(1S)-2,2,2-trifluoro-1-hydroxyethyl 4-[(4-hydroxy-2-oxo-2H-chromen-3-yl)methyl]benzoate;
(1R)-2,2,2-trifluoro-1-hydroxyethyl 4-[(4-hydroxy-2-oxo-2H-chromen-3-yl)methyl]benzoate; or pharmaceutically acceptable salts thereof.

2. A compound according to claim 1, that is
2,2,3,3,3-pentafluoropropyl 4-[(4-hydroxy-2-oxo-2H-chromen-3-yl)methyl]benzoate
3,3,3-trifluoropropyl 4-[(4-hydroxy-2-oxo-2H-chromen-3-yl)methyl]benzoate;
2,2,3,3,3-pentafluoro-1-methylpropyl 4-[(4-hydroxy-2-oxo-2H-chromen-3-yl)methyl]benzoate;
4-fluorobenzyl 4-[(4-hydroxy-2-oxo-2H-chromen-3-yl)methyl]benzoate;
2-(4-fluorophenoxy)ethyl 4-[(4-hydroxy-2-oxo-2H-chromen-3-yl)methyl]benzoate;
2-fluoro-1-(fluoromethyl)ethyl 4-[(4-hydroxy-2-oxo-2H-chromen-3-yl)methyl]benzoate;
2,2,2-trifluoro-1-methylethyl 4-[(4-hydroxy-2-oxo-2H-chromen-3-yl)methyl]benzoate;
2,2,2-trifluoro-1-(trifluoromethyl)ethyl 4-[(4-hydroxy-2-oxo-2H-chromen-3-yl)methyl]benzoate;
2,2,3,3,3-pentafluoro-1-methylpropyl 4-[(4-hydroxy-2-oxo-2H-chromen-3-yl)methyl]benzoate;
2,2,3,3,3-pentafluoro-1-methylpropyl 4-[(4-hydroxy-2-oxo-2H-chromen-3-yl)methyl]benzoate;
(1S)-2,2,2-trifluoro-1-hydroxyethyl 4-[(4-hydroxy-2-oxo-2H-chromen-3-yl)methyl]benzoate;
(1R)-2,2,2-trifluoro-1-hydroxyethyl 4-[(4-hydroxy-2-oxo-2H-chromen-3-yl)methyl]benzoate; or pharmaceutically acceptable salts thereof.

3. A compound according to claim 1, that is
2,2,3,3,3-pentafluoro-1-methylpropyl 4-[(4-hydroxy-2-oxo-2H-chromen-3-yl)methyl]benzoate, or pharmaceutically acceptable salts thereof.

4. A compound or salt according to claim 1, that is
(1S)-2,2,2-trifluoro-1-hydroxyethyl 4-[(4-hydroxy-2-oxo-2H-chromen-3yl)methyl]benzoate, or pharmaceutically acceptable salts thereof.

5. A pharmaceutical composition comprising a compound according to claim 1 or pharmaceutically acceptable salt thereof and at least one carrier, solvent, excipient, and/or adjuvant.

* * * * *

UNITED STATES PATENT AND TRADEMARK OFFICE
CERTIFICATE OF CORRECTION

PATENT NO. : 7,932,405 B2
APPLICATION NO. : 12/268109
DATED : April 26, 2011
INVENTOR(S) : Pascal Druzgala et al.

It is certified that error appears in the above-identified patent and that said Letters Patent is hereby corrected as shown below:

On the Title page, item [63] under Related U.S. Application Data, section (63), please replace:

"Continuation of application No. 11/778,482, filed on Jul. 16, 2007, now Pat. No. 7,666,902." with --Continuation of application No. 11/778,482, filed on Jul. 16, 2007, now Pat. No. 7,666,902, which is a continuation of application No. 11/467,813, filed on Aug. 28, 2006, now Pat. No. 7,285,671, which is a continuation of application No. 11/101,714, filed on Apr. 8, 2005, now Pat. No. 7,253,208, which claims the benefit of provisional application No. 60/561,121, filed on Apr. 8, 2004, and is a continuation-in-part of application No. 10/822,129, filed on Apr. 8, 2004, now Pat. No. 7,145,020.--

Signed and Sealed this
Ninth Day of July, 2013

Teresa Stanek Rea
*Acting Director of the United States Patent and Trademark Office*